US008609335B2

(12) United States Patent
Drmanac et al.

(10) Patent No.: US 8,609,335 B2
(45) Date of Patent: *Dec. 17, 2013

(54) SELF-ASSEMBLED SINGLE MOLECULE ARRAYS AND USES THEREOF

(75) Inventors: Radoje Drmanac, Los Altos Hills, CA (US); Matthew J. Callow, Redwood City, CA (US); Brian K. Hauser, Campbell, CA (US); George Yeung, Mountain View, CA (US)

(73) Assignee: Callida Genomics, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/098,965

(22) Filed: May 2, 2011

(65) Prior Publication Data
US 2011/0281738 A1    Nov. 17, 2011

Related U.S. Application Data

(63) Continuation of application No. 11/541,225, filed on Sep. 29, 2006, now Pat. No. 7,960,104, which is a continuation-in-part of application No. 11/451,691, filed on Jun. 13, 2006.

(60) Provisional application No. 60/821,960, filed on Aug. 10, 2006, provisional application No. 60/776,415, filed on Feb. 24, 2006, provisional application No. 60/725,116, filed on Oct. 7, 2005.

(51) Int. Cl.
*C12Q 1/68*    (2006.01)

(52) U.S. Cl.
USPC ............................................................. 435/6.1

(58) Field of Classification Search
None
See application file for complete search history.

(56) References Cited

U.S. PATENT DOCUMENTS

| 4,719,179 A | 1/1988 | Barany | 435/172.1 |
| 4,883,750 A | 11/1989 | Whiteley | 435/6 |
| 5,091,302 A | 2/1992 | Newman | 435/6 |

(Continued)

FOREIGN PATENT DOCUMENTS

| JP | 4-262799 | 9/1992 |
| JP | 4-304900 | 10/1992 |

(Continued)

OTHER PUBLICATIONS

Callow et al. (2004) Nucleic Acids Research, 32(2):e21, pp. 1-6, published online Jan. 28, 2004.*

(Continued)

*Primary Examiner* — Juliet Switzer
*Assistant Examiner* — Neil P Hammell
(74) *Attorney, Agent, or Firm* — Kilpatrick Townsend & Stockton LLP

(57) ABSTRACT

The present invention provides methods of making and using self-assembled arrays of single polynucleotide molecules for carrying out a variety of large-scale genetic measurements, such as gene expression analysis, gene copy number assessment, and the like. Random arrays used in the invention are "self-assembled" in the sense that they are formed by deposition of polynucleotide molecules onto a surface where they become fixed at random locations. The polynucleotide molecules fixed on the surface are then identified by direct sequence determination of component nucleic acids, such as incorporated probe sequences, or by other decoding schemes. Such identification converts a random array of determinable polynucleotides, and their respective probes into an addressable array of probe sequences.

15 Claims, 29 Drawing Sheets

(56) References Cited

U.S. PATENT DOCUMENTS

| | | | |
|---|---|---|---|
| 5,124,246 A | 6/1992 | Urdea | 435/6 |
| 5,143,854 A | 9/1992 | Pirrung | 436/518 |
| 5,202,231 A | 4/1993 | Drmanac | 435/6 |
| 5,354,668 A | 10/1994 | Auerbach | 435/91.1 |
| 5,403,708 A | 4/1995 | Brennan | 435/6 |
| 5,426,180 A | 6/1995 | Kool | 536/25.3 |
| 5,427,930 A | 6/1995 | Birkenmeyer | 435/91.52 |
| 5,474,796 A | 12/1995 | Brennan | 427/2.13 |
| 5,508,169 A | 4/1996 | Deugau | 435/6 |
| 5,525,464 A | 6/1996 | Drmanac | 435/6 |
| 5,571,677 A | 11/1996 | Gryaznov | 435/6 |
| 5,632,957 A | 5/1997 | Heller | 422/68.1 |
| 5,641,658 A | 6/1997 | Adams | 435/91.2 |
| 5,648,245 A | 7/1997 | Fire | 435/91.1 |
| 5,710,000 A | 1/1998 | Sapolsky | 435/6 |
| 5,714,320 A | 2/1998 | Kool | 435/6 |
| 5,728,524 A | 3/1998 | Sibson | 435/6 |
| 5,744,305 A | 4/1998 | Fodor | 435/6 |
| 5,750,341 A * | 5/1998 | Macevicz | 435/6.19 |
| 5,800,992 A | 9/1998 | Fodor | 435/6 |
| 5,854,033 A | 12/1998 | Lizardi | 435/91.2 |
| 5,866,337 A | 2/1999 | Schon | 435/6 |
| 5,869,245 A | 2/1999 | Yeung | 435/6 |
| 5,871,921 A | 2/1999 | Landegren | 435/66 |
| 5,888,737 A | 3/1999 | DuBridge | 435/6 |
| 5,916,750 A | 6/1999 | Iyer | 435/6 |
| 5,994,068 A | 11/1999 | Guilfoyle | 435/6 |
| 6,004,755 A | 12/1999 | Wang | 435/6 |
| 6,013,445 A | 1/2000 | Albrecht | 435/6 |
| 6,045,994 A | 4/2000 | Zabeau | 435/6 |
| 6,077,668 A | 6/2000 | Kool | 435/6 |
| 6,096,880 A | 8/2000 | Kool | 536/25.3 |
| 6,124,120 A | 9/2000 | Lizardi | 435/91.2 |
| 6,136,537 A | 10/2000 | Macevicz | 435/6 |
| 6,143,495 A | 11/2000 | Lizardi | 435/6 |
| 6,210,891 B1 | 4/2001 | Nyren | 435/6 |
| 6,210,894 B1 | 4/2001 | Brennan | 435/6 |
| 6,218,152 B1 | 4/2001 | Auerbach | 435/91.2 |
| 6,221,603 B1 | 4/2001 | Mahtani | 435/6 |
| 6,255,469 B1 | 7/2001 | Seeman | 536/23.1 |
| 6,258,539 B1 | 7/2001 | Hunkapiller | 435/6 |
| 6,261,808 B1 | 7/2001 | Auerbach | 435/91.1 |
| 6,270,961 B1 | 8/2001 | Drmanac | 435/6 |
| 6,274,320 B1 * | 8/2001 | Rothberg et al. | 435/6.12 |
| 6,274,351 B1 | 8/2001 | Peponnet | 435/91.1 |
| 6,284,497 B1 | 9/2001 | Sabanayagam | 435/91.2 |
| 6,287,824 B1 | 9/2001 | Lizardi | 435/91.2 |
| 6,289,144 B1 | 9/2001 | Neuschafer | 385/12 |
| 6,291,183 B1 | 9/2001 | Pirrung | 435/6 |
| 6,297,006 B1 | 10/2001 | Drmanac | 435/6 |
| 6,297,016 B1 | 10/2001 | Egholm | 435/6 |
| 6,306,597 B1 | 10/2001 | Macevicz | 435/6 |
| 6,309,824 B1 | 10/2001 | Drmanac | 435/6 |
| 6,316,229 B1 | 11/2001 | Lizardi | 435/91.1 |
| 6,329,150 B1 | 12/2001 | Lizardi | 435/6 |
| 6,344,329 B1 | 2/2002 | Lizardi | 435/6 |
| 6,346,413 B1 | 2/2002 | Fodor | 435/287.2 |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,432,360 B1 | 8/2002 | Church | 422/68.1 |
| 6,472,156 B1 | 10/2002 | Wittwer | 435/6 |
| 6,491,871 B1 | 12/2002 | Fodor | 422/63 |
| 6,500,620 B2 | 12/2002 | Yu | 435/6 |
| 6,514,768 B1 | 2/2003 | Guire | 436/518 |
| 6,534,293 B1 | 3/2003 | Baranay | 435/91.2 |
| 6,558,928 B1 | 5/2003 | Landegren | 435/91.1 |
| 6,573,369 B2 | 6/2003 | Henderson | 536/23.1 |
| 6,576,448 B2 | 6/2003 | Weissman | 435/91.2 |
| 6,589,726 B1 | 7/2003 | Butler | 435/4 |
| 6,610,481 B2 | 8/2003 | Koch | 435/6 |
| 6,620,584 B1 | 9/2003 | Chee | 435/6 |
| 6,632,609 B2 | 10/2003 | Lizardi | 435/6 |
| 6,653,077 B1 | 11/2003 | Brenner | 435/6 |
| 6,654,505 B2 | 11/2003 | Bridgham | 382/278 |
| 6,783,943 B2 | 8/2004 | Christian | 435/6 |
| 6,787,308 B2 | 9/2004 | Balasubramanian | 435/6 |
| 6,812,005 B2 | 11/2004 | Fan | 435/91.2 |
| 6,864,052 B1 | 3/2005 | Drmanac | 435/6 |
| 6,890,741 B2 | 5/2005 | Fan | 435/91.2 |
| 6,913,884 B2 | 7/2005 | Stuelpnagel | 435/6 |
| 6,977,153 B2 | 12/2005 | Kumar | 435/6 |
| 6,998,228 B2 | 2/2006 | Henderson | 435/4 |
| 7,011,945 B2 | 3/2006 | Qiao | 435/6 |
| 7,064,197 B1 | 6/2006 | Rabbani | 536/24.3 |
| 7,244,559 B2 | 7/2007 | Rothberg | 435/6 |
| 7,264,929 B2 | 9/2007 | Rothberg | 435/6 |
| 7,276,720 B2 | 10/2007 | Ulmer | 356/246 |
| 7,384,737 B2 | 6/2008 | Barnes | 435/6 |
| 7,544,473 B2 | 6/2009 | Brenner | 435/6 |
| 2002/0004204 A1 | 1/2002 | O'Keefe | 435/6 |
| 2002/0055100 A1 | 5/2002 | Kawashima | 435/6 |
| 2002/0076716 A1 | 6/2002 | Sabanayagam | 435/6 |
| 2002/0197621 A1 | 12/2002 | Drmanac | 435/6 |
| 2003/0068629 A1 | 4/2003 | Rothberg | 435/6 |
| 2003/0143542 A1 | 7/2003 | Qiao | 435/6 |
| 2003/0170914 A1 | 9/2003 | Guire | 435/518 |
| 2004/0002090 A1 | 1/2004 | Mayer | 435/6 |
| 2004/0086892 A1 | 5/2004 | Crothers | 435/6 |
| 2004/0224325 A1 | 11/2004 | Knapp | 435/6 |
| 2004/0229221 A1 | 11/2004 | Schon | 435/6 |
| 2004/0248144 A1 * | 12/2004 | Mir | 435/6 |
| 2004/0248161 A1 | 12/2004 | Rothberg | 435/6 |
| 2005/0019776 A1 | 1/2005 | Callow et al. | |
| 2005/0037356 A1 | 2/2005 | Gullberg | 435/6 |
| 2005/0042649 A1 | 2/2005 | Balasubramanian | 435/6 |
| 2005/0059022 A1 | 3/2005 | Ruan et al. | |
| 2005/0100939 A1 | 5/2005 | Namsaraev | 435/6 |
| 2005/0191656 A1 | 9/2005 | Drmanac | 435/6 |
| 2005/0214840 A1 | 9/2005 | Chen | 435/6 |
| 2005/0244863 A1 | 11/2005 | Mir | 435/6 |
| 2006/0012784 A1 | 1/2006 | Ulmer | 356/246 |
| 2006/0012793 A1 | 1/2006 | Harris | 356/436 |
| 2006/0024681 A1 | 2/2006 | Smith | 435/6 |
| 2006/0024711 A1 | 2/2006 | Lapidus | 435/6 |
| 2006/0223097 A1 | 10/2006 | Sapolsky et al. | |
| 2007/0015182 A1 | 1/2007 | Abarzua | 435/6 |
| 2007/0072208 A1 | 3/2007 | Drmanac | 435/6 |
| 2007/0099208 A1 | 5/2007 | Drmanac. | 435/6 |
| 2008/0318796 A1 | 12/2008 | Drmanac | 506/3 |
| 2009/0005252 A1 | 1/2009 | Drmanac | 506/3 |
| 2009/0011943 A1 | 1/2009 | Drmanac | 506/4 |
| 2009/0075343 A1 | 3/2009 | Sparks et al. | |
| 2009/0099041 A1 | 4/2009 | Church et al. | |
| 2009/0137414 A1 | 5/2009 | Drmanac | 506/9 |
| 2009/0143235 A1 | 6/2009 | Drmanac | 506/5 |
| 2009/0155781 A1 | 6/2009 | Drmanac | 435/6 |
| 2009/0176652 A1 | 7/2009 | Dahl et al. | |
| 2009/0203551 A1 | 8/2009 | Dahl et al. | |
| 2009/0264299 A1 | 10/2009 | Drmanac | 506/3 |

FOREIGN PATENT DOCUMENTS

| | | |
|---|---|---|
| WO | WO 92/01813 | 2/1992 |
| WO | WO 95/09248 | 4/1995 |
| WO | WO 01/62982 | 8/2001 |
| WO | WO 02/074988 | 9/2002 |
| WO | 03/102231 A1 | 12/2003 |
| WO | WO 2004/072294 | 8/2004 |
| WO | WO 2004/076683 | 9/2004 |
| WO | WO 2005/047523 | 5/2005 |
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2005/040425 | 5/2006 |
| WO | WO 2006/055521 | 5/2006 |
| WO | WO 2006/073504 | 7/2006 |
| WO | WO 2006/084132 | 8/2006 |
| WO | WO 2007/014397 | 2/2007 |

(56) References Cited

FOREIGN PATENT DOCUMENTS

| WO | WO 2007/025124 | 3/2007 |
|---|---|---|
| WO | WO 2007/061425 | 5/2007 |
| WO | WO 2007/062160 | 5/2007 |
| WO | WO 03/012119 | 2/2013 |

OTHER PUBLICATIONS

Amersham Biosciences product brochure, "Passport kits for EMD assays: a novel tool for high-throughput SNP analysis and mutation scanning," Life Science News 2 (1999).

Babon et al, "Mutation detection using fluorescent enzyme mismatch cleavage with T4 endonuclease VII," Electrophoresis, 20: 1162-1170 (1999).

Beaucage, "Strategies in the preparation of DNA oligonucleotide arrays for diagnostic applications," Curr. Med. Chem., 8: 1213-1244 (2001).

Blanco et al., "Highly efficient DNA synthesis by the phage phi 29 DNA polymerase," J. Biol. Chem., v. 264, issue 15, p. 8935-8940 (1989).

Callow, Matthew J., et al. "Selective DNA amplification from complex genomes using universal double-sided adapters," Nucleic Acids Research, vol. 32, No. 2, e21, p. 1-6, (Jan. 2004).

Chen et al., "A Homogeneous, Ligase-Mediated DNA Diagnostic Test", Genome Research, vol. 8, No. 5, May 1998, pp. 549-556.

Collins et al, "Directional cloning of DNA fragments at a large distance from an initial probe: A circularization method," Proc. Natl. Acad. Sci., 81: 6812-6816 (1984).

Cowie et al, "Identification of APC gene mutations in colorectal cancer using universal microarray-based combinatorial sequencing-by-hybridization," Human Mutation, 24:261-271 (2004).

Dahl et al, "Multiplex amplification enabled by selective circularization of large sets of genomic DNA fragments," Nucleic Acids Research, 33(8): e71 (2005).

Drmanac et al, "Sequencing by hybridization (SBH): advantages, achievements, and opportunities," Adv. Biochem. Engineering/Biotechnology, 77: 76-101 (2002).

Epicentre Biotechnologies product brochure No. 222, "CircLigase ssDNA Ligase," (Aug. 2005).

Gerry et al, "Universal DNA microarray method for multiplex detection of low abundance point mutations," J. Mol. Biol., 292: 251-262 (1999).

Gunderson et al, "Mutation detection by ligation to complete n-mer DNA arrays," Genome Research, 8: 1142-1153 (1998).

Inganas et al, "Enzymatic mutation detection in the P53 gene," Clin. Chem., 46: 1562-1573 (2000).

Kandpal et al, "Selective enlargement of a large size genomic DNA fragment by affinity capture: an approach for genome mapping," Nucleic Acids Research, 18: 1789 (1990).

Kool, "Circular oligonucleotides: New concepts in oligonucleotide design," Annu. Rev. Biophys. Biomol. Struct., 25: 1-28 (1996).

Kuhn et al., "A novel, high-performace random array platform for quantitative gene expression profiling," Genome Research, 14: 2347-2356 (2004).

Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).

Lehr et al, "Real-time detection of nucleic acid interactions by total internal reflection fluorescence," Anal. Chem., 75: 2414-2420 (2003).

Lizardi et al, "Mutation detection and single-molecule counting using isothermal rolling-circle amplification," Nature Genetics, 19: 225-232 (1998).

Lockhart et al, "Expression monitoring by hybridization to high-density oligonucleotide arrays," Nature Biotechnology, 14: 1675-1680 (1996).

Mashal et al, "Detection of mutations by cleavage of DNA heteroduplexes with bacteriophage resolvases," Nature Genetics, 9: 177-183 (1995).

McGall et al, "High-density GeneChip oligonucleotide probe arrays," Adv. Biochem. Engineering/Biotechnology, 77: 22 (2002).

Mitra et al, "In situ localized amplification and contact replication of many individual DNA molecules," Nucleic Acids Research, 27(24): e34 (1999).

Nallur et al, "Signal amplification by rolling circle amplification on DNA microarrays," Nucleic Acids Research, 29(23): e118 (2001).

Neuschafer et al, "Evanescent resonator chips: a universal platform with superior sensitivity for fluorescence-based microarrays," Biosensors and Bioelectronics, 18: 489-497 (2003).

Nie et al, "Scoring single-nucleotide polymorphisms at the single molecule level by counting individual DNA cleavage events on a surface," Anal. Chem., 77: 6594-6600 (2005).

Parsons et al, "Genotypic selection methods for the direct analysis of point mutations," Mutation Research, 387: 97-121 (1997).

Parsons et al, "Evaluation of MutS as a tool for direct measurement of point mutations in genomic DNA," Mutation Research, 374: 277-285 (1997).

Pohl et al, "Construction of a Not I linking library and isolation of new markers close to Huntington's disease gene," Nucleic Acids Research, 16: 9185-9198 (1988).

Predki et al, "Rolling circle amplification for sequencing templates," Methods Mol. Biol., 255: 189-196 (2004).

Roth et al., "Expression profiling using a hexamer-bsed universal microarray," Nature Biotechnolgoy, 22: 418-426 (2004).

Sasuga et al, "Development of a microscopic platform for real-time monitoring of biomolecular interactions," Genome Research, 16: 132-139 (2006).

Shendure et al, "Advanced Sequencing Technologies: Methods and Goals," Nature Reviews Genetics, vol. 5, pp. 335-344 (2004).

Smirnov et al, "Method of manufacturing whole-genome microarrays by rolling circle amplification," Genes, Chromosomes & Cancer, 40: 72-77 (2004).

Taylor, "Enzymatic and chemical cleavage methods," Electrophoresis, 20: 1125-1130 (1999).

Tringe et al, "Metagenomics: DNA Sequencing of Environmental Samples," Nature Reviews Genetics, vol. 6, pp. 805-814 (2005).

Vingron et al., "Sequence Alignment and Penalty Choice Review of Concepts, Case Studies and Implications," J. Mol. Biol, vol. 235, issue 1, pp. 1-12 (1994).

Wazawa et al, "Total internal reflection fluorescence microscopy in single molecule nanobioscience," Adv. Biochem. Engineering/Biotechnology, 95: 77-106 (2005).

Weiss, "Fluorescence spectroscopy of single biomolecules," Science, 283: 1676 (1999).

Yamakawa et al., "A simple and robust method of preparation of cDNA nylon microarrays," DNA Research, 11: 353-360 (2004).

Zhang et al, "Amplification of target-specific, ligation-dependent circular probe," Gene, 211: 277-285 (1998).

Supplementary Search Report for EP Application No. 06815722.1, mailed on Dec. 22, 2009, 9 pages.

* cited by examiner

SEQUENCE LISTING

```
<160> NUMBER OF SEQ ID NOS: 17

<210> SEQ ID NO 1
<211> LENGTH: 80
<212> TYPE: DNA
<213> ORGANISM: Unknown
<220> FEATURE:
<223> OTHER INFORMATION: probe
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
```

```
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(80)
<223> OTHER INFORMATION: n is a, c, g, or t

<400> SEQUENCE: 1
nnnnnnnngc atancacgan gtcatnatcg tncaaacgtc agtccangaa tcnagatcca      60
cttagantgn cgnnnnnnnn                                                 80

<210> SEQ ID NO 2
<211> LENGTH: 50
<212> TYPE: DNA
<213> ORGANISM: Unknown
<220> FEATURE:
<223> OTHER INFORMATION: adaptor

<400> SEQUENCE: 2
tatcatctgg atgttaggaa gacaaaagga agctgaggac attaacggac                50

<210> SEQ ID NO 3
<211> LENGTH: 15
<212> TYPE: DNA
<213> ORGANISM: Unknown
<220> FEATURE:
<223> OTHER INFORMATION: adaptor

<400> SEQUENCE: 3
accttcagac cagat                                                     15

<210> SEQ ID NO 4
<211> LENGTH: 20
<212> TYPE: DNA
<213> ORGANISM: Unknown
<220> FEATURE:
<223> OTHER INFORMATION: adaptor
<220> FEATURE:
<221> NAME/KEY: misc_feature
<222> LOCATION: (1)..(7)
<223> OTHER INFORMATION: n is a, c, g, or t

<400> SEQUENCE: 4
nnnnnnngtc cgttaatgtc                                                20

<210> SEQ ID NO 5
```

```
<211> LENGTH: 22
<212> TYPE: DNA
<213> ORGANISM: Unknown
<220> FEATURE:
<223> OTHER INFORMATION: adaptor
<220> FEATURE:
<221> NAME/KEY: misc_feature
<222> LOCATION: (1)..(1)
<223> OTHER INFORMATION: biotinylated base
<220> FEATURE:
<221> NAME/KEY: misc_feature
<222> LOCATION: (16)..(22)
<223> OTHER INFORMATION: n is a, c, g, or t

<400> SEQUENCE: 5
atctggtctg aaggtnnnnn nn                                              22

<210> SEQ ID NO 6
<211> LENGTH: 20
<212> TYPE: DNA
<213> ORGANISM: Unknown
<220> FEATURE:
<223> OTHER INFORMATION: adaptor
<220> FEATURE:
<221> NAME/KEY: misc_feature
<222> LOCATION: (1)..(1)
<223> OTHER INFORMATION: biotinylated base

<400> SEQUENCE: 6
cttttgtctt cctaacatcc                                                 20

<210> SEQ ID NO 7
<211> LENGTH: 16
<212> TYPE: DNA
<213> ORGANISM: Unknown
<220> FEATURE:
<223> OTHER INFORMATION: adaptor

<400> SEQUENCE: 7
agatgataat ctggtc                                                     16

<210> SEQ ID NO 8
<211> LENGTH: 65
<212> TYPE: DNA
<213> ORGANISM: Unknown
<220> FEATURE:
<223> OTHER INFORMATION: adaptor

<400> SEQUENCE: 8
tatcatctac tgcactgacc ggatgttagg aagacaaaag gaagctgagg gtcacattaa     60
cggac                                                                 65

<210> SEQ ID NO 9
<211> LENGTH: 23
<212> TYPE: DNA
<213> ORGANISM: Unknown
<220> FEATURE:
<223> OTHER INFORMATION: adaptor
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (23)..(23)
<223> OTHER INFORMATION: dideoxynucleotide

<400> SEQUENCE: 9
nnnnnnngtc cgttaatgtg acc                                             23
```

```
<210> SEQ ID NO 10
<211> LENGTH: 17
<212> TYPE: DNA
<213> ORGANISM: Unknown
<220> FEATURE:
<223> OTHER INFORMATION: adaptor
<220> FEATURE:
<221> NAME/KEY: misc_feature
<222> LOCATION: (17)..(17)
<223> OTHER INFORMATION: dideoxynucleotide

<400> SEQUENCE: 10
agatgatatt tttttc                                                       17

<210> SEQ ID NO 11
<211> LENGTH: 24
<212> TYPE: DNA
<213> ORGANISM: Unknown
<220> FEATURE:
<223> OTHER INFORMATION: primer

<400> SEQUENCE: 11
tcagcttcct tttgtcttcc taac                                              24

<210> SEQ ID NO 12
<211> LENGTH: 30
<212> TYPE: DNA
<213> ORGANISM: Unknown
<220> FEATURE:
<223> OTHER INFORMATION: probe

<400> SEQUENCE: 12
ggatgttagg aagacaaaag gaagctgagg                                        30

<210> SEQ ID NO 13
<211> LENGTH: 80
<212> TYPE: DNA
<213> ORGANISM: Unknown
<220> FEATURE:
<223> OTHER INFORMATION: probe
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
```

```
<400> SEQUENCE: 13
nnnnnnnngc atancacgan gtcatnatcg tncaaacgtc agtccangaa tcnagatcca    60
cttagantaa aaaaaaaaaa                                                80

<210> SEQ ID NO 14
<211> LENGTH: 30
<212> TYPE: DNA
<213> ORGANISM: Unknown
<220> FEATURE:
<223> OTHER INFORMATION: probe

<400> SEQUENCE: 14
ggatgttagg aagacaaaag gaagctgagg                                     30

<210> SEQ ID NO 15
<211> LENGTH: 11
<212> TYPE: DNA
<213> ORGANISM: Unknown
<220> FEATURE:
<223> OTHER INFORMATION: probe

<400> SEQUENCE: 15
cattaacgga c                                                         11

<210> SEQ ID NO 16
<211> LENGTH: 11
<212> TYPE: DNA
<213> ORGANISM: Unknown
<220> FEATURE:
<223> OTHER INFORMATION: probe

<400> SEQUENCE: 16
tgagcgattc g                                                         11

<210> SEQ ID NO 17
<211> LENGTH: 12
<212> TYPE: DNA
<213> ORGANISM: Unknown
<220> FEATURE:
<223> OTHER INFORMATION: adaptor

<400> SEQUENCE: 17
acattaacgg ac                                                        12
```

SELF-ASSEMBLED SINGLE MOLECULE ARRAYS AND USES THEREOF

This application is a continuation of U.S. patent application Ser. No. 11/541,225 filed Sep. 29, 2006 which is a continuation-in-part of U.S. patent application Ser. No. 11/451,691 filed 13 Jun. 2006, and claims priority from U.S. provisional applications Ser. No. 60/821,960 filed 10 Aug. 2006, Ser. No. 60/776,415 filed 24 Feb. 2006, and Ser. No. 60/725,116 filed 7 Oct. 2005, each of which is hereby incorporated by reference in its entirety.

GOVERNMENT INTERESTS

This invention was made with government support under grant No. 1 U01 AI057315-01 awarded by the National Institutes of Health. The government has certain rights in the invention.

FIELD OF THE INVENTION

The present invention relates to methods and compositions for large-scale genetic analysis, and more particularly, to methods and compositions for genome-wide analysis of gene expression, genetic variation, genomic copy number variation, and like phenomena.

BACKGROUND

Living systems, particularly higher animals, such as mammals, comprise many complex networks of interacting genes and gene products. In order to understand the functions of such networks in both health and disease, several large-scale analytical technologies have been developed for making genome-wide measurements, including measurements of genetic variation, gene expression, gene copy number variation, and like phenomena, e.g. Lochhart et al, Nature Biotechnology, 14: 1675-1680 (1996); DeRisi et al, Science, 278: 680-686 (1997); Golub et al, Science, 286: 531-537 (1999); Kennedy et al (2003), Nature Biotechnology, 21: 1233-1237; Gunderson et al (2005), Nature Genetics, 37: 549-554; Pinkel and Albertson (2005), Nature Genetics Supplement, 37: S11-S17; Cobb et al, Proc. Natl. Acad. Sci., 102: 4801-4806 (2005). Such technologies commonly provide highly parallel readouts by the use of large arrays of hybridization probes whose positions are known or determinable; thus, signals at each particular probe site can be related to a genetic measurement, and the collection of array signals can be related to genome-wide response or state. Miniaturization has proved to be extremely important for increasing the scale and reducing the costs of such approaches. However, further increases in scale and reductions in cost would be highly desirable, particularly for measurements of genetic phenomena in complex organisms, such as humans.

In view of the above, it would be advantageous for the medical, life science, and other applied biological fields if there were available molecular arrays and arraying techniques that permitted efficient and convenient analysis of large numbers of target molecules, such as substantially all expressed genes in a mammalian-sized genome, in parallel in a single analytical operation.

SUMMARY OF THE INVENTION

In one aspect, the invention provides methods of making large-scale genetic measurements using high density single molecule arrays, methods of making such arrays, and kits for implementing such methods. The invention employs random arrays of a plurality of different polynucleotide molecules disposed on a surface, where the polynucleotide molecules each comprise replicate copies at least one probe sequence and where the polynucleotide molecules each comprise a plurality of attachment functionalities that are capable of forming bonds with one or more functionalities on the surface. After polynucleotide molecules are fixed on the surface, their probe sequences are identified so that complementary target sequences that hybridize to them can be identified and quantitated by location and signal strength.

In one aspect, random arrays employed by the invention comprise single polynucleotide molecules disposed on a surface, where the single polynucleotide molecules each comprise a concatemer of at least one probe sequence and at least one adaptor oligonucleotide and each is attached to such surface by the formation of duplexes between capture oligonucleotides on the surface and the attachment oligonucleotides in the concatemer.

In still another form, random arrays employed by the invention comprise single polynucleotide molecules disposed on a surface, where each single polynucleotide molecule comprises a plurality of complementary functionalities and is attached to the surface by linkages between one or more functionalities on the surface and such complementary functionalities.

In regard to the above arrays, in another aspect, such single polynucleotide molecules are disposed in a planar array randomly distributed onto discrete spaced apart regions having defined positions. Preferably, in this aspect, the discrete spaced apart regions each have an area that permits the capture of no more than a single polynucleotide molecule and each is surrounded by an inter-regional space that is substantially free of other polynucleotide molecules.

In one aspect, the invention provides a method of making a probe array comprising the following steps: (a) providing a plurality of polynucleotide molecules attached to a surface of a support, wherein each polynucleotide molecule has a random coil state and comprises a concatemer of multiple copies of a probe sequence such that the polynucleotide molecule is attached to the surface within a region substantially equivalent to a projection of the random coil on the surface and randomly disposed at a density such that at least thirty percent of the polynucleotide molecules have a nearest neighbor distance of at least fifty nm; and (b) identifying the probe sequence of each polynucleotide molecule on the surface to form the probe array.

In another aspect, the invention provides a method of making a probe array comprising the following steps: (a) providing a support having a surface with capture oligonucleotides attached thereto; providing a plurality of polynucleotide molecules attached to the surface, wherein each polynucleotide molecule comprises a concatemer of multiple copies of a probe sequence and an adaptor oligonucleotide such that the polynucleotide molecule is attached to the surface by one or more complexes formed between capture oligonucleotides and adaptor oligonucleotides, the polynucleotide molecules being randomly disposed on the surface at a density such that at least a majority of the polynucleotide molecules have a nearest neighbor distance of at least fifty nm; and (b) identifying the probe sequence of each polynucleotide molecule on the surface to form the probe array.

In another aspect, the invention provides a method of making a probe array comprising the steps of (a) generating a plurality of polynucleotide molecules each comprising a concatemer of a probe sequence and an adaptor oligonucleotide; (b) disposing the plurality of polynucleotide molecules onto a support having a surface with capture oligonucleotides attached thereto so that the polynucleotide molecules are fixed to the surface by one or more complexes formed between capture oligonucleotides and adaptor oligonucleotides and so that the polynucleotide molecules are randomly distributed on the surface at a density such that a majority of the polynucleotide molecules have a nearest neighbor distance of at least fifty nm, thereby forming the array of polynucleotide molecules; and (c) identifying the probe sequence of each polynucleotide molecule on the surface to form the probe array.

In still another aspect, the invention provides a method of making a probe array comprising the following steps: (a) generating a plurality of polynucleotide molecules each comprising a concatemer of a probe sequence from a source nucleic acid; (b) disposing the plurality of polynucleotide molecules onto a support having a surface having reactive functionalities attached thereto so that the polynucleotide molecules are fixed to the surface by one or more linkages formed between the reactive functionalities and complementary functionalities on the polynucleotide molecules and so that the polynucleotide molecules are randomly disposed on the surface at a density such that at least a majority of the polynucleotide molecules have a nearest neighbor distance of at least fifty nm, thereby forming the array of polynucleotide molecules; and (c) identifying the probe sequence of each polynucleotide molecule on the surface to form the probe array.

In one aspect, the invention includes various array products, with over 1, 2, 3, 5, 10, 50, 100, 1000 millions of concatemer based probes with determined or inferred sequence longer than 10, 20, 30, 40, 50, 60, 80, 100, 150, 200 bases, and spot size smaller than 8, 4, 2, 1, 0.5, 0.25, 0.1 micron.

In another aspect, the invention includes kits for making random arrays of the invention and for implementing applications of the random arrays of the invention, particularly high-throughput analysis of samples containing mixtures of target polynucleotides.

The present invention provides a significant advance in the field of genetic analysis by providing assays that employ high density arrays of single polynucleotide molecules comprising replicate copies of probes having determinable sequences. In one form, such single molecules are concatemers of probe sequences arrayed at densities that permit efficient high resolution analysis of mammalian-sized genomes, including genome-wide gene expression analysis and genome-wide assessments of copy number patterns, methylation patterns, chromosomal stability, and the like.

DETAILED DESCRIPTION OF THE INVENTION

Figure 1A:
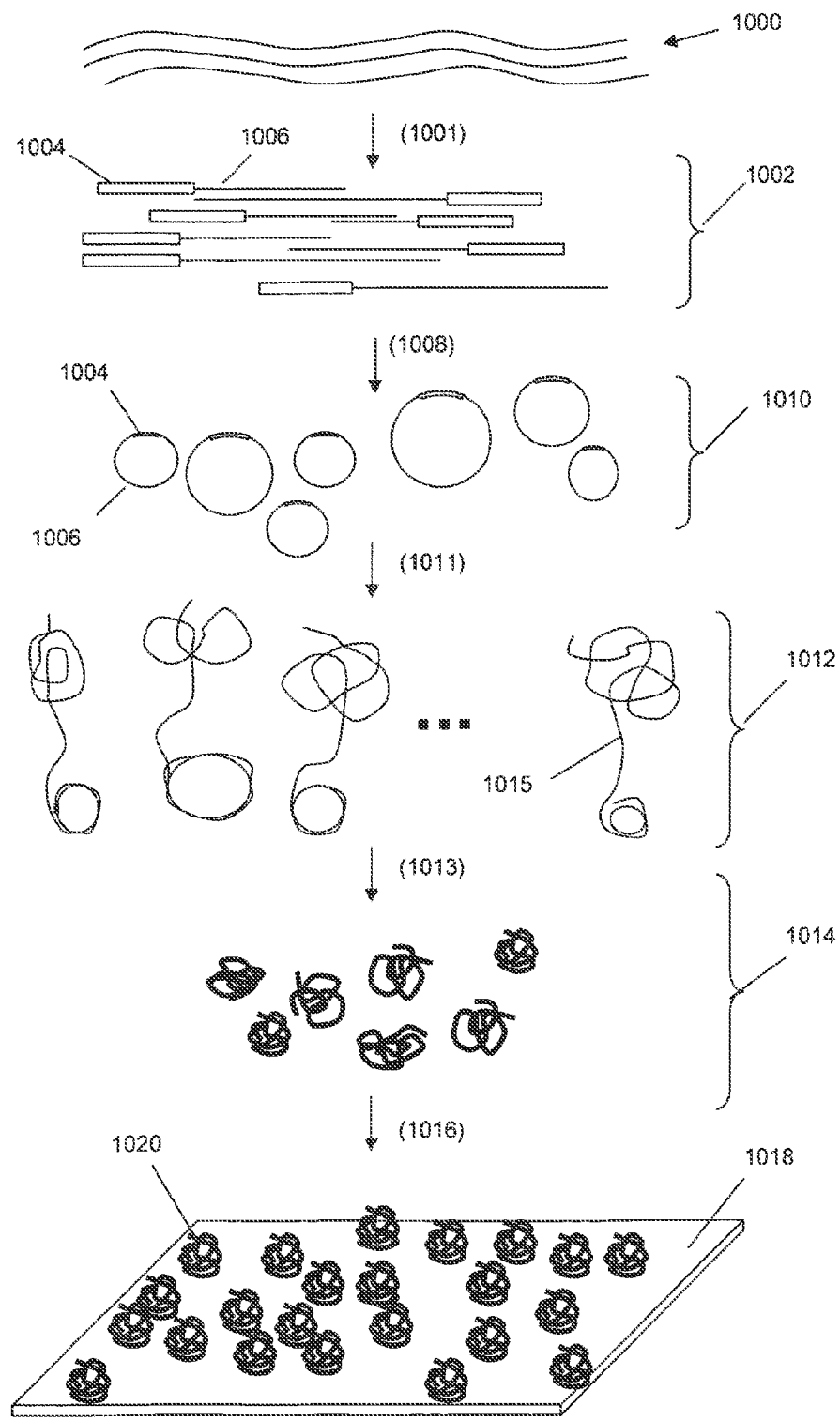
FIGS. 1A-1K illustrate various embodiments of the methods and compositions of the invention.

The practice of the present invention may employ, unless otherwise indicated, conventional techniques and descriptions of organic chemistry, molecular biology (including recombinant techniques), cell biology, biochemistry, and immunology, which are within the skill of the art. Such conventional techniques include, but are not limited to, vector construction, microbial host transformation, selection and application of genetic markers, manipulation of large polynucleotide fragments, preparation of synthetic polynucleotides, application of recombination systems, nucleic acid sequencing and analysis, polymer array synthesis, hybridization, ligation, detection of hybridization using labels, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed W. H. Freeman Pub., New York, N.Y., all of which are herein incorporated in their entirety by reference for all purposes.

The present invention provides methods of making and using self-assembled arrays of single polynucleotide molecules for making a variety of large-scale measurements. Random arrays used in the invention are "self-assembled" in the sense that they are formed by deposition of polynucleotide molecules onto a surface, usually from a solution, where they become fixed at random locations. The polynucleotide molecules fixed on the surface are then identified by direct sequence determination of component nucleic acids, such as respective probe sequences, or by other decoding schemes. Such identification converts a random array of determinable polynucleotides, and their respective probes, into an addressable array of probe sequences.

An important feature of such self-assembled arrays is that the polynucleotide molecules on the surface are a sample of the total population of polynucleotides in the solution used for its manufacture. Thus, the probability that a particular array contains every species of polynucleotide (and hence, every species of probe sequence) depends on the sample size (i.e. the number of polynucleotides fixed to the surface) and the total number of different species of polynucleotide in the population, e.g. Brenner, U.S. Pat. No. 5,846,719; and Brenner et al, Proc. Natl. Acad. Sci., 97: 1665-1670 (2000). There is a great deal of guidance in the literature for making appropriate design choices to achieve adequate representation of probe sequences under such circumstances, e.g. Maniatis et al, Molecular Cloning: A Laboratory Manual (Cold Spring Harbor Laboratory, New York, 1982). For example, to ensure a 99% probability of having at least one copy of each probe sequence, Maniatis et al recommend a sample size of at least five times the total number of different species of probe sequence (i.e. 5-fold coverage). In one aspect, random arrays used with the invention have a density of one polynucleotide per 100 nm$^2$; thus, a 1 cm$^2$ array can accommodate a sample up to $10^{10}$ polynucleotides, which is adequate to provide full representation (with over 99% probability) of most conventional cDNA and genomic libraries. In certain aspects, random arrays are employed that provide at least 2-fold coverage of probe sequences, or at least 3-fold coverage of probe sequences, or at least 4-fold coverage of probe sequences, or at least 5-fold coverage of probe sequences. Where probe sequences are cDNAs (or portions thereof) from a cDNA library, in one aspect, random arrays based thereon contain at least 2-fold coverage of probe sequences, or at least 3-fold coverage of probe sequences, or at least 4-fold coverage of probe sequences, or at least 5-fold coverage of probe sequences. An advantage of higher fold coverage is that a single kind of probe sequence, on average, is present in many separate polynucleotides, so that a measurement is based on an average of many separate signals.

Once formed, random arrays are employed in the invention similarly to conventional high density hybridization arrays. Preparation, labeling, and application of target sequences to such probes is well known is the art, as exemplified by the following references that are incorporated by reference: Hames et al, editors, Nucleic Acid Hybridization a Practical Approach (IRL Press, Oxford, 1985); Tijssen, Hybridization with Nucleic Acid Probes, Parts I & II (Elsevier Publishing Company, 1993); Hardiman, Microarray Methods and Applications (DNA Press, 2003); Schena, editor, DNA Microarrays a Practical Approach (IRL Press, Oxford, 1999); Wetmur, Crit. Rev. Biochem. Mol. Biol., 26: 227-259 (1991); DeRisi et al, Science, 278: 680-686 (1997); Chee et al, Science, 274: 610-614 (1996); Duggan et al, Nature Genetics, 21: 10-14 (1999); Freeman et al, Biotechniques, 29: 1042-1055 (2000); and U.S. Pat. Nos. 6,410,229; 6,040,138; 6,576,424; and the like.

Random Arrays of Polynucleotides

As mentioned, the invention employs random arrays of single polynucleotide molecules for large-scale parallel analysis of populations of molecules, particularly nucleic acid fragments, such as genomic DNA, cDNA, or cRNA fragments. Polynucleotides used in random arrays may comprise branched polymers as well as linear polymers, such as concatemers of DNA fragments. Branched DNA structures are synthesized using known techniques, e.g. Gryaznov, U.S. Pat. No. 5,571,677; Urdea et al, U.S. Pat. No. 5,124,246; Seeman et al, U.S. Pat. No. 6,255,469; Iyer et al, U.S. Pat. No. 5,916,750; and the like, which are incorporated herein by reference. Preferably, polynucleotide molecules used in random arrays are linear and, in further preference, are produced by RCR from a circular template.

Generally, single polynucleotide molecules of the random arrays comprise one or more attachments portions and a plurality of probe sequence portions. In one aspect, such portions are different and are present as alternating segments in a polynucleotide molecule. The attachment portions provide for multivalent attachment to a surface, particularly within a compact or restricted area on a surface so that signals generated from the polynucleotide molecule, e.g. by multiple bound target sequences, are concentrated. That is, preferably, each polynucleotide molecule occupies a compact and limited region of the surface. Polynucleotide molecules may be bound to a surface in a variety of ways. Multi-valent bonds may be covalent or non-covalent. Non-covalent bonds include formation of duplexes between capture oligonucleotides on the surface and complementary sequences in the polynucleotide molecule, and adsorption to a surface by attractive noncovalent interactions, such as Van der Waal forces, hydrogen bonding, ionic and hydrophobic interactions, and the like. Multi-valent covalent bonding may be accomplished, as described more fully below, by providing reactive functionalities on the surface that can reactive with a plurality of complementary functionalities in the polynucleotide molecules.

Polynucleotide molecules are disposed randomly on a surface of a support material, usually from a solution; thus, in one aspect, polynucleotide molecules are uniformly distributed on a surface in close approximation to a Poisson distribution. In another aspect, polynucleotide molecules are disposed on a surface that contains discrete spaced apart regions in which polynucleotide molecules are attached.

In one aspect, single polynucleotide molecules are roughly in a random coil configuration on a surface and are confined to the area of a discrete spaced apart region. Preferably, design choices are made so that there is one polynucleotide molecule per discrete spaced apart region. Factors related to such design choices include polynucleotide size, the nature of components nucleic acids making up the polynucleotide (e.g. whether nucleotide analogs or derivatized nucleotides are included), how the polynucleotides are prepared (e.g. RCR, ligation of synthetic segments, etc), the areas of the discrete spaced apart regions, functionalities on the discrete spaced apart regions, and the like.

In one aspect, the discrete spaced apart regions have defined locations in a regular array, which may correspond to a rectilinear pattern, hexagonal pattern, or the like. A regular array of such regions is advantageous for detection and data analysis of signals collected from the arrays during an analysis. Also, single molecules confined to the restricted area of a discrete spaced apart region provide a more concentrated or intense signal, particularly when fluorescent probes are used in analytical operations, thereby providing higher signal-to-noise values. Single polynucleotide molecules of the invention are randomly distributed on the discrete spaced apart regions so that a given region usually is equally likely to receive any of the different single polynucleotide molecules. In other words, the resulting arrays are not spatially addressable immediately upon fabrication, but may be made so by carrying out an identification or decoding operation. That is, the identities of the probe sequences of the single polynucleotide molecules are determinable.

In one aspect, polynucleotides of random arrays are sufficiently large that their size, e.g. a linear dimension (such as a diameter) of a volume occupied in a conventional physiological saline solution, is approximately equivalent to that a discrete spaced apart region. For linear polynucleotides, in one aspect, sizes may range from a few thousand nucleotides, e.g. 10,000, to several hundred thousand nucleotides, e.g. 100-200 thousand. As explained more fully below, in several embodiments, such polynucleotides are made by generating circular DNAs and then replicating them in a rolling circle replication reaction to form concatemers of complements of the circular DNAs. Binding of DNA concatemers may proceed at specific temperatures with or without mixing until about 80%-99% of spots are occupied. More than 50, 60, 70, 80, 90 or 95% of spots in the grid may have single informative DNA species, excluding errors produced by amplification.

The above concepts are illustrated more fully in the embodiments shown schematically in FIGS. 1A-1D. After describing these figures, elements of the invention are disclosed in additional detail and examples are given. As mentioned above, in one aspect, macromolecular structures of the invention are single stranded polynucleotides comprising concatemers of a probe sequence or fragment. In particular, such polynucleotides may be concatemers of a probe sequence and an adaptor oligonucleotide. For example, source nucleic acid (1000) is treated (1001) to form single stranded fragments (1006), preferably in the range of from 50 to 600 nucleotides, and more preferably in the range of from 300 to 600 nucleotides, which are then ligated to adaptor oligonucleotides (1004) to form a population of adaptor-fragment conjugates (1002). Source nucleic acid (1000) may be genomic DNA extracted from a sample using conventional techniques, or a cDNA or genomic library produced by conventional techniques, or synthetic DNA, or the like. Treatment (1001) usually entails fragmentation by a conventional technique, such as chemical fragmentation, enzymatic fragmentation, or mechanical fragmentation, followed by denaturation to produce single stranded DNA fragments. Adaptor oligonucleotides (1004), in this example, are used to form (1008) a population (1010) of DNA circles by a method, such as that illustrated in FIG. 2A. In one aspect, each member of population (1010) has an adaptor with an identical primer binding site and a DNA fragment from source nucleic acid (1000). The adapter also may have other functional elements including, but not limited to, tagging sequences, attachment sequences, palindromic sequences, restriction sites, functionalization sequences, and the like. In other embodiments, classes of DNA circles may be created by providing adaptors having different primer binding sites. After DNA circles (1010) are formed, a primer and rolling circle replication (RCR) reagents may be added to generate (1011) in a conventional RCR reaction a population (1012) of concatemers (1015) of the complements of the adaptor oligonucleotide and DNA fragments, which population can then be isolated using conventional separation techniques. Alternatively, RCR may be implemented by successive ligation of short oligonucleotides, e.g. 6-mers, from a mixture containing all possible sequences, or if circles are synthetic, a limited mixture of oligonucleotides having selected sequences for circle replication. Concatemers may also be generated by ligation of probe sequences in the presence of a bridging template DNA complementary to both beginning and end of the probe molecule. A population of different probe DNA may be converted in concatemers by a mixture of corresponding bridging templates. Isolated concatemers (1014) are then disposed (1016) onto support surface (1018) to form a random array of single molecules. Attachment may also include wash steps of varying stringencies to remove incompletely attached single molecules or other reagents present from earlier preparation steps whose presence is undesirable or that are nonspecifically bound to surface (1018). Concatemers (1020) can be fixed to surface (1018) by a variety of techniques, including covalent attachment and non-covalent attachment. In one embodiment, surface (1018) may have attached capture oligonucleotides that form complexes, e.g. double stranded duplexes, with a segment of the adaptor oligonucleotide, such as the primer binding site or other elements. In other embodiments, capture oligonucleotides may comprise oligonucleotide clamps, or like structures, that form triplexes with adaptor oligonucleotides, e.g. Gryaznov et al, U.S. Pat. No. 5,473,060. In another embodiment, surface (1018) may have reactive functionalities that react with complementary functionalities on the concatemers to form a covalent linkage, e.g. by way of the same techniques used to attach cDNAs to microarrays, e.g. Smirnov et al (2004), Genes, Chromosomes & Cancer, 40: 72-77; Beaucage (2001), Current Medicinal Chemistry, 8: 1213-1244, which are incorporated herein by reference. Long DNA molecules, e.g. several hundred nucleotides or larger, may also be efficiently attached to hydrophobic surfaces, such as a clean glass surface that has a low concentration of various reactive functionalities, such as —OH groups. Concatemers of DNA fragments may be further amplified in situ after disposition of a surface. For example after disposition, concatemer may be cleaved by reconstituting a restriction site in adaptor sequences by hybridization of an oligonucleotide, after which the fragments are circularized as described below and amplified in situ by a RCR reaction.

Figure 1B:
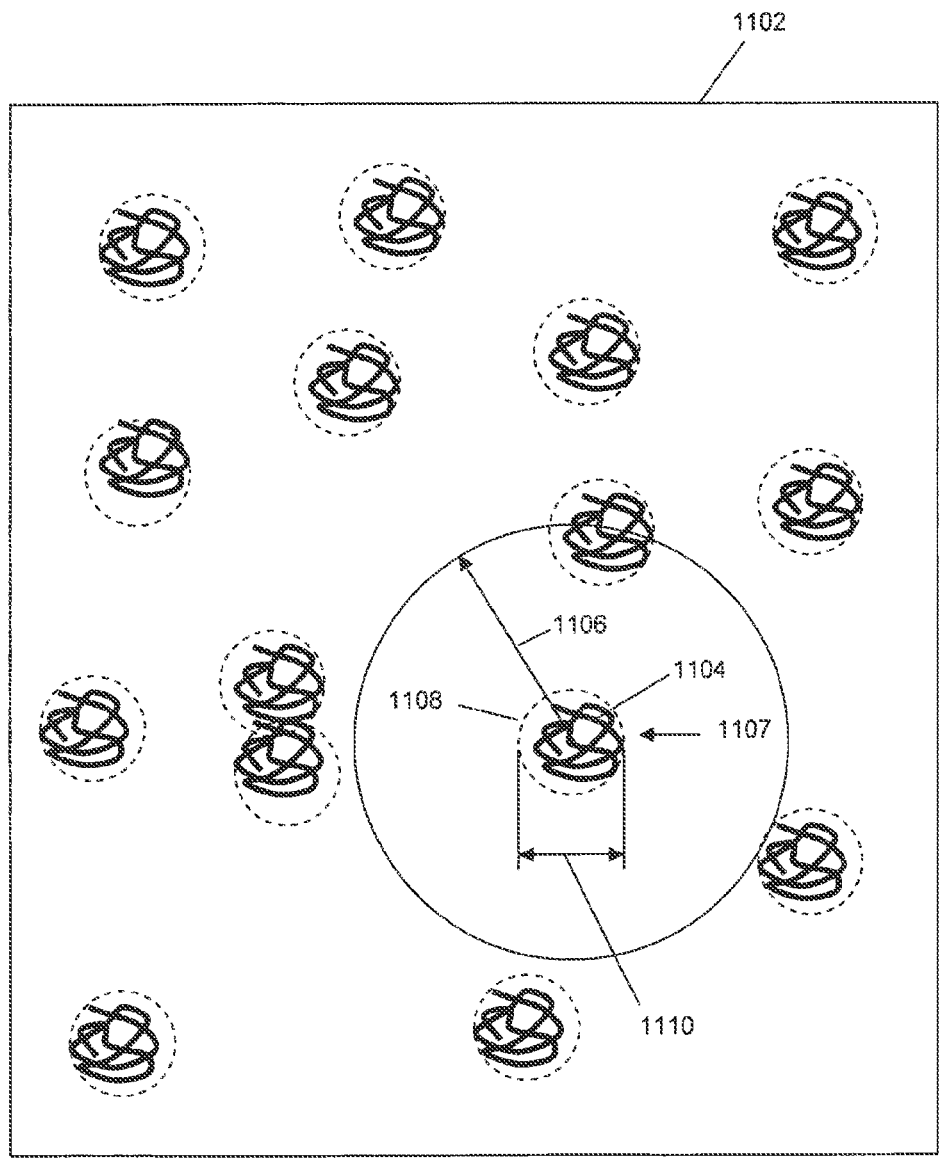
Figure 2A:
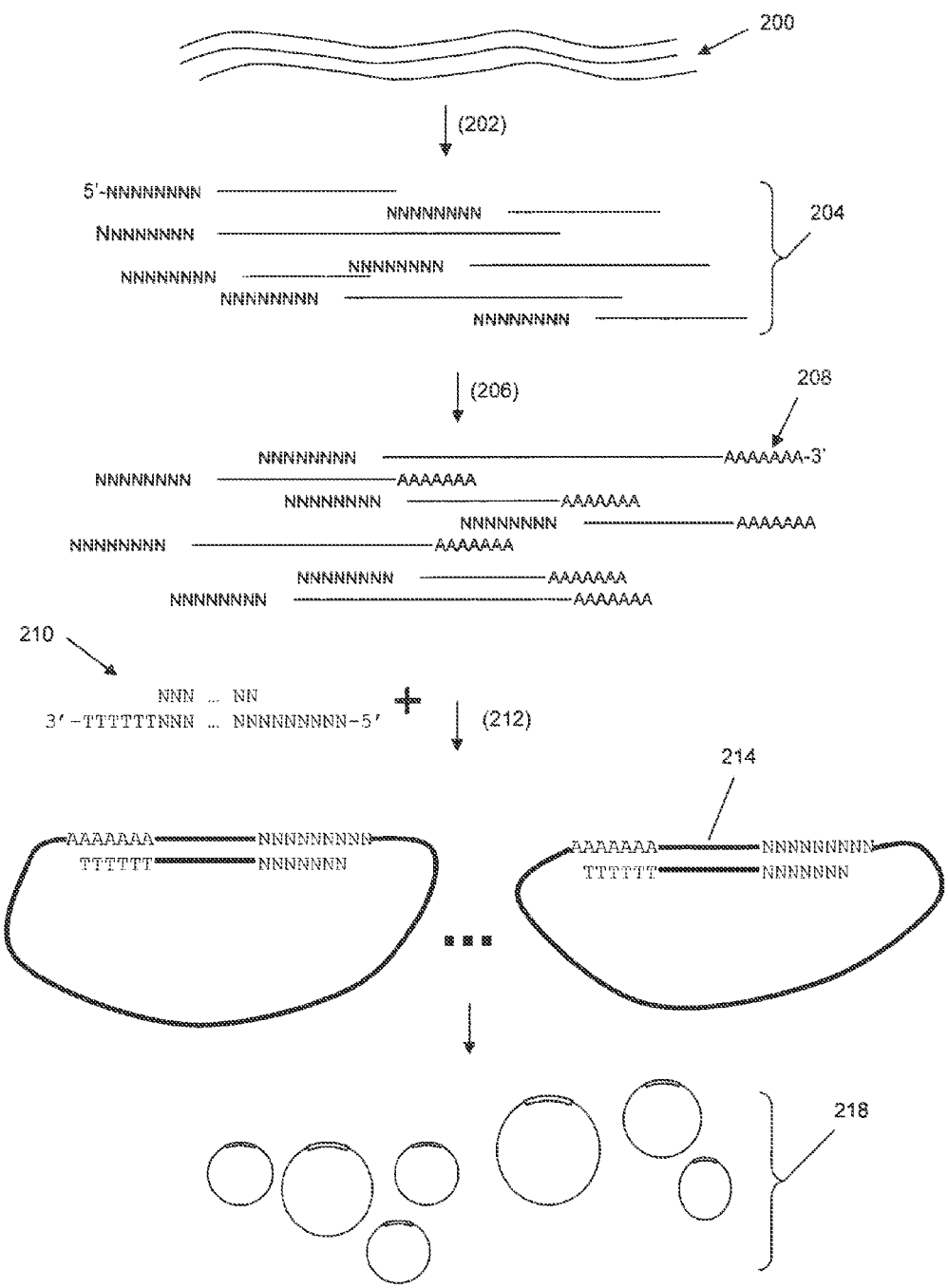
FIGS. 2A-2H illustrate methods of circularizing genomic DNA fragments for generating concatemers of polynucleotide analytes.

FIG. 1B illustrates a section (1102) of a surface of a random array of single molecules, such as single stranded polynucleotides. Such molecules under conventional conditions (a conventional DNA buffer, e.g. TE, SSC, SSPE, or the like, at room temperature) form random coils that roughly fill a spherical volume in solution having a diameter of from about 100 to 300 nm, which depends on the size of the DNA and buffer conditions, in a manner well known in the art, e.g. Edvinsson, "On the size and shape of polymers and polymer complexes," Dissertation 696 (University of Uppsala, 2002). One measure of the size of a random coil polymer, such as single stranded DNA, is a root mean square of the end-to-end distance, which is roughly a measure of the diameter of the randomly coiled structure. Such diameter, referred to herein as a "random coil diameter," can be measured by light scatter, using instruments, such as a Zetasizer Nano System (Malvern Instruments, UK), or like instrument. Additional size measures include molecular weight, e.g. in Daltons, and total polymer length, which in the case of a branched polymer is the sum of the lengths of all its branches. Upon attachment to a surface, depending on the attachment chemistry, density of linkages, the nature of the surface, and the like, single stranded polynucleotides fill a flattened spheroidal volume that on average is bounded by a region (1107) defined by dashed circles (1108) having a diameter (1110), which is approximately equivalent to the diameter of a concatemer in random coil configuration. Stated another way, in one aspect, polynucleotides, e.g. concatemers, and the like, are attached to surface (1102) within a region that is substantially equivalent to a projection of its random coil state onto surface (1102), for example, as illustrated by dashed circles (1108). An area occupied by a macromolecular structure can vary, so that in some embodiments, an expected area may be within the range of from 2-3 times the area of projection (1108) to some fraction of such area, e.g. 25-50 percent. As mentioned else where, preserving the compact form of the macromolecular structure on the surface allows a more intense signal to be produced by probes, e.g. fluorescently labeled oligonucleotides, specifically directed to components of a macromolecular structure or concatemer. The size of diameter (1110) of regions (1107) and distance (1106) to the nearest neighbor region containing a single molecule are two quantities of interest in the fabrication of arrays. A variety of distance metrics may be employed for measuring the closeness of single molecules on a surface, including center-to-center distance of regions (1107), edge-to-edge distance of regions (1007), and the like. Usually, center-to-center distances are employed herein. The selection of these parameters in fabricating arrays used in the invention depends in part on the signal generation and detection systems used in subsequent analytical processes. Generally, densities of single molecules are selected that permit at least twenty percent, or at least thirty percent, or at least forty percent, or at least a majority of the molecules to be resolved individually by the signal generation and detection systems used. In one aspect, a density is selected that permits at least seventy percent of the single molecules to be individually resolved. In one aspect, whenever scanning electron microscopy is employed, for example, with molecule-specific probes having gold nanoparticle labels, e.g. Nie et al (2006), Anal. Chem., 78: 1528-1534, which is incorporated by reference, a density is selected such that at least a majority of single molecules have a nearest neighbor distance of 50 nm or greater; and in another aspect, such density is selected to ensure that at least seventy percent of single molecules have a nearest neighbor distance of 100 nm or greater. In another aspect, whenever optical microscopy is employed, for example with molecule-specific probes having fluorescent labels, a density is selected such that at least a majority of single molecules have a nearest neighbor distance of 200 nm or greater; and in another aspect, such density is selected to ensure that at least seventy percent of single molecules have a nearest neighbor distance of 200 nm or greater. In still another aspect, whenever optical microscopy is employed, for example with molecule-specific probes having fluorescent labels, a density is selected such that at least a majority of single molecules have a nearest neighbor distance of 300 nm or greater; and in another aspect, such density is selected to ensure that at least seventy percent of single molecules have a nearest neighbor distance of 300 nm or greater, or 400 nm or greater, or 500 nm or greater, or 600 nm or greater, or 700 nm or greater, or 800 nm or greater. In still another embodiment, whenever optical microscopy is used, a density is selected such that at least a majority of single molecules have a nearest neighbor distance of at least twice the minimal feature resolution power of the microscope.

In another aspect, polymer molecules of the invention are disposed on a surface so that the density of separately detectable polymer molecules is at least 1000 per $\mu m^2$, or at least 10,000 per $\mu m^2$, or at least 100,000 per $\mu m^2$.

Figure 1C:
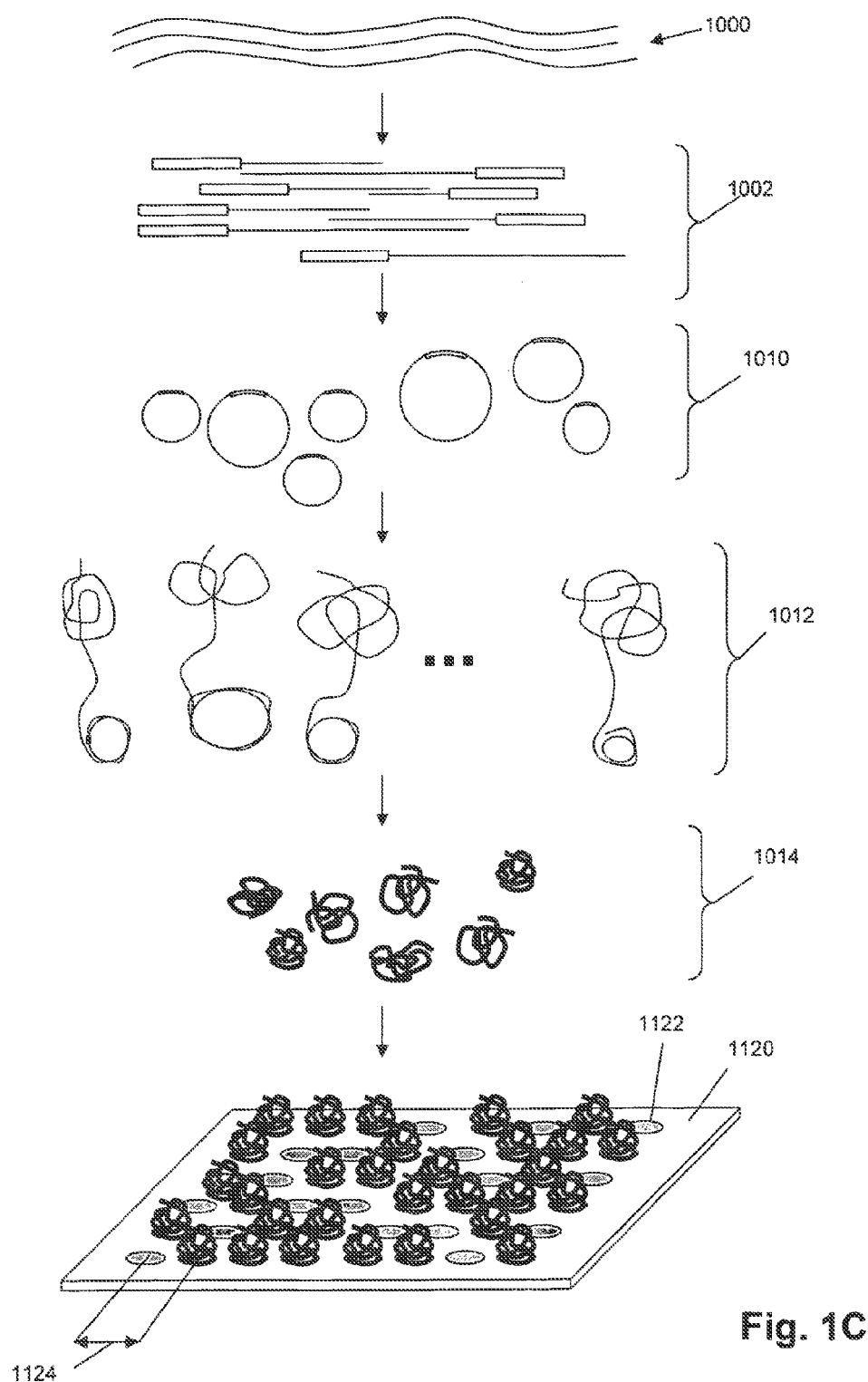

In another aspect of the invention, illustrated for a particular embodiment in FIG. 1C, the requirement of selecting densities of randomly disposed single molecules to ensure desired nearest neighbor distances is obviated by providing on a surface discrete spaced apart regions that are substantially the sole sites for attaching single molecules. That is, in such embodiments the regions on the surface between the discrete spaced apart regions, referred to herein as "inter-regional areas," are inert in the sense that concatemers, or other macromolecular structures, do not bind to such regions. In some embodiments, such inter-regional areas may be treated with blocking agents, e.g. DNAs unrelated to concatemer DNA, other polymers, and the like As in FIGS. 1A and 1C, source nucleic acids (1000) are fragmented and adaptored (1002) for circularization (1010), after which concatemers are formed by RCR (1012). Isolated concatemers (1014) are then applied to surface (1120) that has a regular array of discrete spaced apart regions (1122 in FIG. 1C) that each have a nearest neighbor distance (1124) that is determined by the design and fabrication of surface (1120). As described more fully below, arrays of discrete spaced apart regions (1122) having micron and submicron dimensions for derivatizing with capture oligonucleotides or reactive functionalities can be fabricated using conventional semiconductor fabrication techniques, including electron beam lithography, nano imprint technology, photolithography, and the like. Generally, the area of discrete spaced apart regions (1122) is selected, along with attachment chemistries, macromolecular structures employed, and the like, to correspond to the size of single molecules of the invention so that when single molecules are applied to surface (1120) substantially every region (1122) is occupied by no more than one single molecule. The likelihood of having only one single molecule per discrete spaced apart region may be increased by selecting a density of reactive functionalities or capture oligonucleotides that results in fewer such moieties than their respective complements on single molecules. Thus, a single molecule will "occupy" all linkages to the surface at a particular discrete spaced apart region, thereby reducing the chance that a second single molecule will also bind to the same region. In particular, in one embodiment, substantially all the capture oligonucleotides in a discrete spaced apart region hybridize to adaptor oligonucleotides a single macromolecular structure. In one aspect, a discrete spaced apart region contains a number of reactive functionalities or capture oligonucleotides that is from about ten percent to about fifty percent of the number of complementary functionalities or adaptor oligonucleotides of a single molecule. The length and sequence(s) of capture oligonucleotides may vary widely, and may be selected in accordance with well known principles, e.g. Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985). In one aspect, the lengths of capture oligonucleotides are in a range of from 6 to 30 nucleotides, and in another aspect, within a range of from 8 to 30 nucleotides, or from 10 to 24 nucleotides. Lengths and sequences of capture oligonucleotides are selected (i) to provide effective binding of polynucleotides to a surface, so that losses of polynucleotides are minimized during steps of subsequent analytical operations, such as washing, etc., and (ii) to avoid interference with analytical operations. In regard to (i), in one aspect, sequences and lengths are selected to provide duplexes between capture oligonucleotides and their complements that are sufficiently stable so that they do not dissociate in a stringent wash, e.g. as implemented in a conventional hybridization assay. In regard to (ii), if DNA fragments are from a particular species of organism, then databases, when available, may be used to exclude potential capture sequences that may form spurious or undesired hybrids with probe sequences. Other factors in selecting sequences for capture oligonucleotides are similar to those considered in selecting primers, hybridization probes, oligonucleotide tags, and the like, for which there is ample guidance, as evidenced by the references cited below in the Definitions section. In some embodiments, a discrete spaced apart region may contain more than one kind of capture oligonucleotide, and each different capture oligonucleotide may have a different length and sequence. In one aspect of embodiments employing regular arrays of discrete spaced apart regions, sequences of capture oligonucleotides are selected so that sequences of capture oligonucleotide at nearest neighbor regions have different sequences. In a rectilinear array, such configurations are achieved by rows of alternating sequence types. In other embodiments, a surface may have a plurality of subarrays of discrete spaced apart regions wherein each different subarray has capture oligonucleotides with distinct nucleotide sequences different from those of the other subarrays. A plurality of subarrays may include 2 subarrays, or 4 or fewer subarrays, or 8 or fewer subarrays, or 16 or fewer subarrays, or 32 or fewer subarrays, or 64 of fewer subarrays. In still other embodiments, a surface may include 5000 or fewer subarrays. In one aspect, capture oligonucleotides are attached to the surface of an array by a spacer molecule, e.g.

polyethylene glycol, or like inert chain, as is done with microarrays, in order to minimize undesired affects of surface groups or interactions with the capture oligonucleotides or other reagents.

In one aspect, the area of discrete spaced apart regions (1122) is less than 1 µm$^2$; and in another aspect, the area of discrete spaced apart regions (1122) is in the range of from 0.04 µm$^2$ to 1 µm$^2$; and in still another aspect, the area of discrete spaced apart regions (1122) is in the range of from 0.2 µm$^2$ to 1 µm$^2$. In another aspect, when discrete spaced apart regions are approximately circular or square in shape so that their sizes can be indicated by a single linear dimension, the size of such regions are in the range of from 125 nm to 250 nm, or in the range of from 200 nm to 500 nm. In one aspect, center-to-center distances of nearest neighbors of regions (1122) are in the range of from 0.25 µm to 20 µm; and in another aspect, such distances are in the range of from 1 µm to 10 µm, or in the range from 50 to 1000 nm. In one aspect, regions (1120) may be arranged on surface (1018) in virtually any pattern in which regions (1122) have defined locations, i.e. in any regular array, which makes signal collection and data analysis functions more efficient. Such patterns include, but are not limited to, concentric circles of regions (1122), spiral patterns, rectilinear patterns, hexagonal patterns, and the like. Preferably, regions (1122) are arranged in a rectilinear or hexagonal pattern.

Figure 1D:
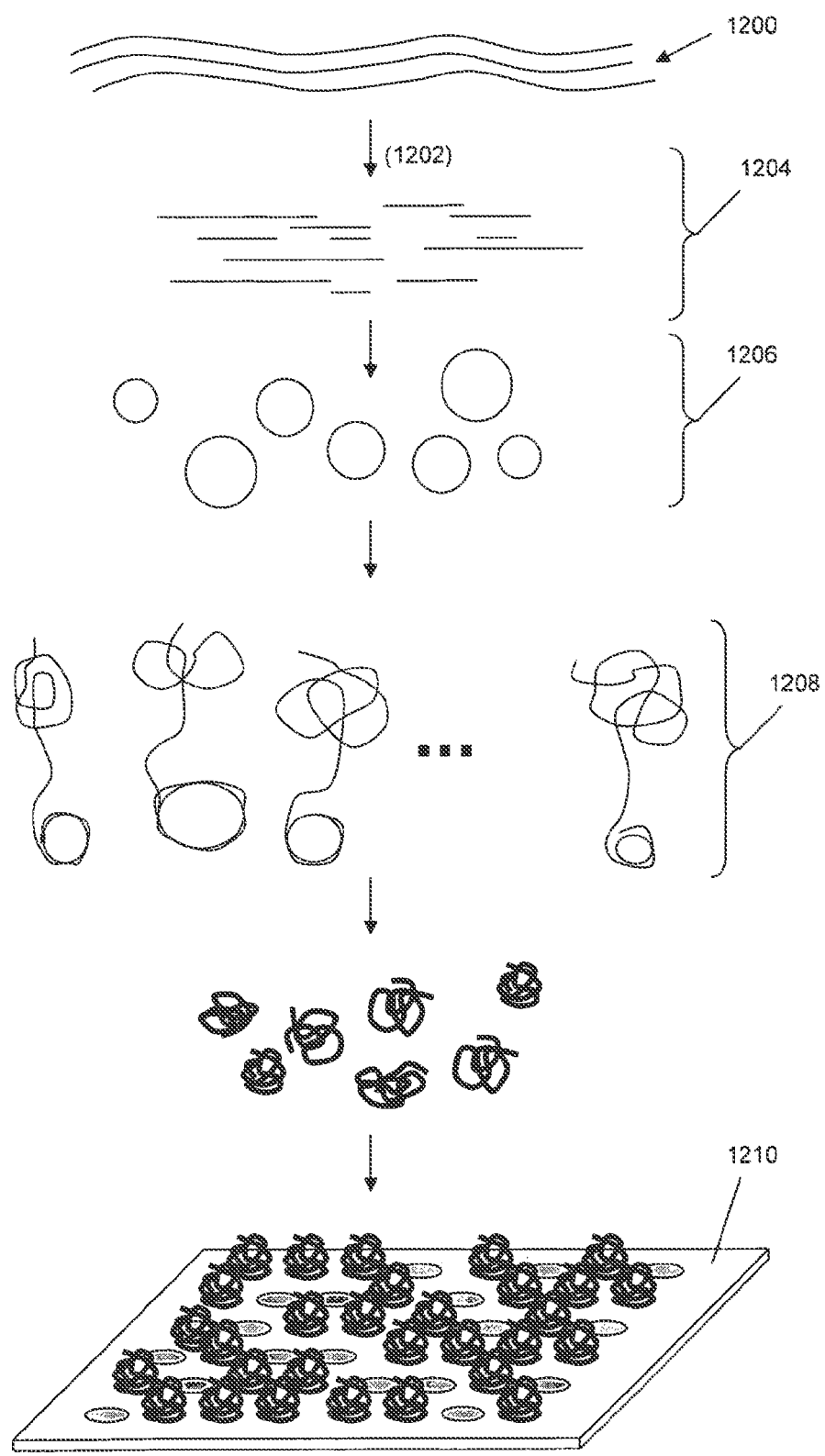

As illustrated in FIG. 1D, in certain embodiments, DNA circles prepared from source nucleic acid (1200) need not include an adaptor oligonucleotide. As before, source nucleic acid (1200) is fragmented and denatured (1202) to form a population of single strand fragments (1204), preferably in the size range of from about 50 to 600 nucleotides, and more preferably in the size range of from about 300 to 600 nucleotides, after which they are circularized in a non-template driven reaction with circularizing ligase, such as CircLigase (Epicentre Biotechnologies, Madison, Wis.), or the like. After formation of DNA circles (1206), concatemers are generated by providing a mixture of primers that bind to selected sequences. The mixture of primers may be selected so that only a subset of the total number of DNA circles (1206) generate concatemers. After concatemers are generated (1208), they are isolated and applied to surface (1210) to form a random array of the invention.

As noted above, there is abundant guidance in the literature for selecting appropriate functionalities for fixing polynucleotides to a support surface to form a random array. In one aspect, polynucleotides may be linked or fixed to a surface by homo- or heterobifunctional reagents, which are available commercially (e.g. Pierce) and are disclosed in references such as Hermanson, Bioconjugate Techniques (Academic Press, New York, 1996), which is incorporated by reference. Exemplary bifunction reagents for linking an amino group to a sufhydryl group include N-succinimidyl 3-(2-pyridyldithio)propionate (SPDP), succinimidyloxycarbonyl-α-methyl-α-(2-pyridyldithio)toluene (SMPT), succinimidyl-4-(N-maleimidomethyl)cyclohexane-1-carboxylate (SMCC), m-maleimidobenzoyl-N-hydroxysuccinimide ester (MBS), N-succinimidyl(4-iodoacetyl)aminobenzoate (SIAB), succinimidyl 6-((iodoacetyl)amino)hexanoate (SIAX), and like reagents. Polynucleotides may also be fixed to support surfaces by way of non-covalent linkages, such as biotin-streptavidin linkages, and the like.

Source Nucleic Acids and Circularization of Probe Sequences

Probe sequences of random arrays may be derived from virtually any population of nucleic acid fragments that can produce useful information in a hybridization assay. In one aspect, probe sequences of random arrays are extracted or derived from nucleic acids in a sample. Exemplary samples include, but are not limited to, samples from a population of individuals or organisms, a single patient, a single tissue from multiple patients, multiple tissues from one or more patients, an organism of economic interest, a community of microorganisms, a collection of synthetic nucleic acids (e.g. the set of all nucleic acid sequences having a length selected from the range of from 10-20), or the like. In another aspect, probe sequences may be derived from a genomic DNA library, cDNA library, cRNA library, siRNA library, or other classes of natural nucleic acids. In another aspect, the invention provides random arrays for comparing gene expression or copy number abundances among different biological samples; in such embodiment, probe sequences may be derived from a consensus or reference library of DNA fragments. Typically, the nucleotide sequences from a reference library are known and the sequences typically are listed in sequence databases, such as Genbank, Embl, or the like. In one aspect, a reference library of DNA may comprise a cDNA library or genomic library from a known cell type or tissue source. For example, a reference library of DNA may comprise a cDNA library or a genomic library derived from the tissue of a healthy individual and a test library of DNA (from which target sequences are derived) may comprise a cDNA library or genomic library derived from the same tissue of a diseased individual. Reference libraries of DNA may also comprise an assembled collection of individual polynucleotides, cDNAs, genes, or exons thereof, e.g. genes or exons encoding all or a subset of known p53 variants, genes of a signal transduction pathway, or the like. The DNA use for making probes may be enriched through various procedures. For example, variable regions between 2 and 20 or between 20 and 2000 individuals may be collected using mismatch cutting enzymes or other procedures to make arrays enriched for polymorphisms.

In one aspect, probe sequences are synthetic polynucleotides having predetermined sequences. In one embodiment, synthetic probe sequences are selected for detecting protein-DNA binding, e.g. Gronostajski, Nucleic Acids Research, 15: 5545-5559 (1987); Oliphant et al, Gene, 44: 177-183 (1986); Oliphant et al, Meth. Enzymol., 155: 568-582 (1987); which references are incorporated by reference. In one aspect, probe sequences for such use may have the following form: "oligo1-NNN . . . NNN-oligo2", where "oligo1" and "oligo2" are oligonucleotides of known sequence, e.g. primer binding sites, which sandwich a random sequence region "NNN . . . NNN", which may vary in length and composition. In one form, the random sequence region has a length in the range of from 6 to 20, or in the range of from 8 to 16. In another form, "N" is any of the four natural nucleotides. In another aspect, preparation of selected synthetic probes (for example, between about 20 to 100 bases in length) may be produced individually or in various pools. One pool example is 10-10,000 probes of different sequences mixed and extended with the same 5-15 base sequence in the same synthesis. These probes may be tagged for decoding or decoded directly by sequencing a portion of, or the entire, probe. 4-15 bases is sufficient for identifying thousands to millions of sequences.

Genomic DNA is obtained using conventional techniques, for example, as disclosed in Sambrook et al., supra, 1999; Current Protocols in Molecular Biology, Ausubel et al., eds. (John Wiley and Sons, Inc., NY, 1999), or the like, Important factors for isolating genomic DNA include the following: 1) the DNA is free of DNA processing enzymes and contaminating salts; 2) the entire genome is equally represented; and 3) the DNA fragments are between about 5,000 and 100,000 bp in length. In many cases, no digestion of the extracted DNA is required because shear forces created during lysis and extraction will generate fragments in the desired range. In another embodiment, shorter fragments (1-5 kb) can be generated by enzymatic fragmentation using restriction endonucleases. In one embodiment, 10-100 genome-equivalents of DNA ensure that the population of fragments covers the entire genome. In some cases, it is advantageous to provide carrier DNA, e.g. unrelated circular synthetic double-stranded DNA, to be mixed and used with the sample DNA whenever only small amounts of sample DNA are available and there is danger of losses through nonspecific binding, e.g. to container walls and the like.

In generating fragments in either stage, fragments may be derived from either an entire genome or it may be derived from a selected subset of a genome. Many techniques are available for isolating or enriching fragments from a subset of a genome, as exemplified by the following references that are incorporated by reference: Kandpal et al (1990), Nucleic Acids Research, 18: 1789-1795; Callow et al, U.S. patent publication 2005/0019776; Zabeau et al, U.S. Pat. No. 6,045,994; Deugau et al, U.S. Pat. No. 5,508,169; Sibson, U.S. Pat. No. 5,728,524; Guilfoyle et al, U.S. Pat. No. 5,994,068; Jones et al, U.S. patent publication 2005/0142577; Gullberg et al, U.S. patent publication 2005/0037356; Matsuzaki et al, U.S. patent publication 2004/0067493; and the like.

Figure 2B:
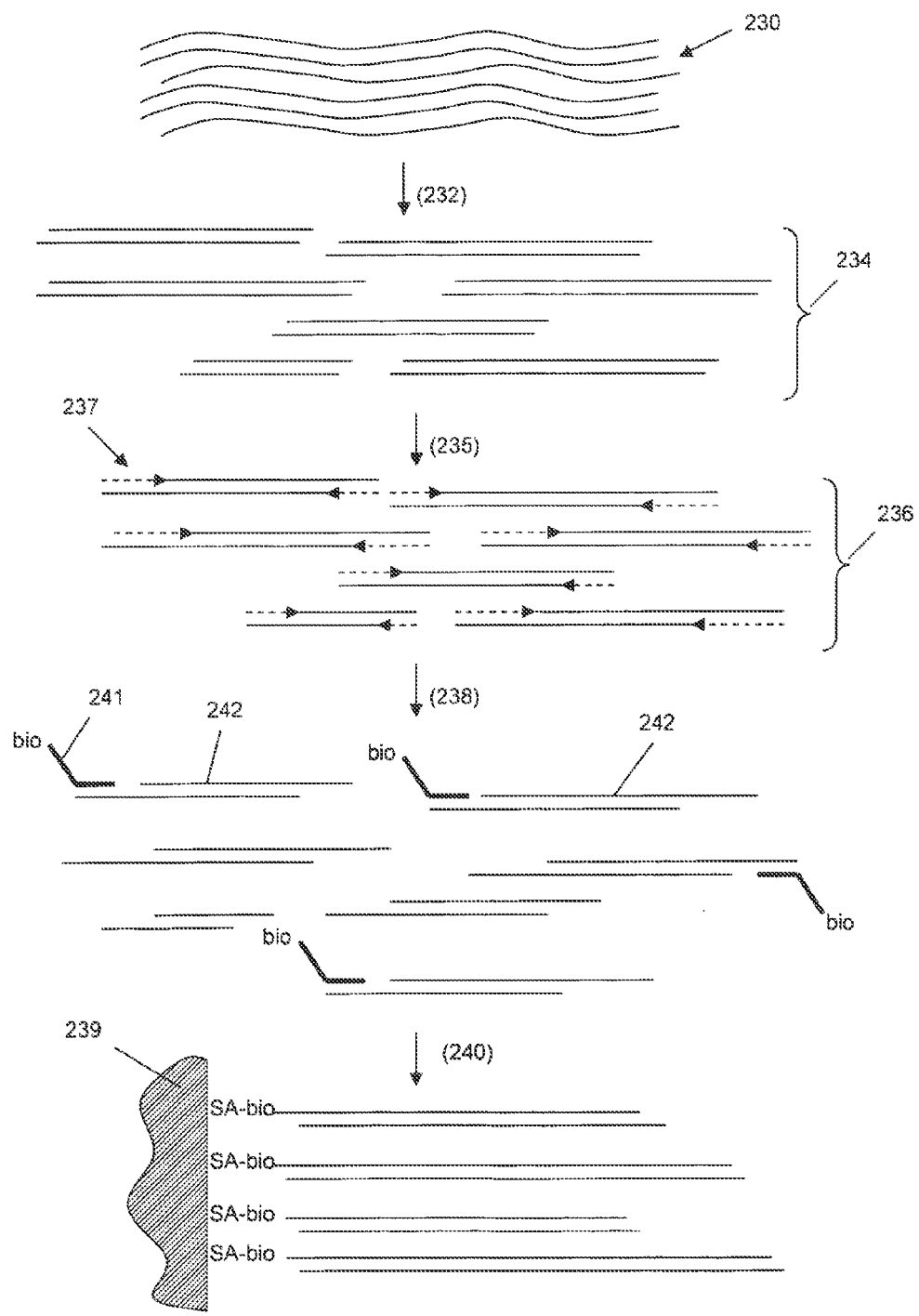
Figure 2C:
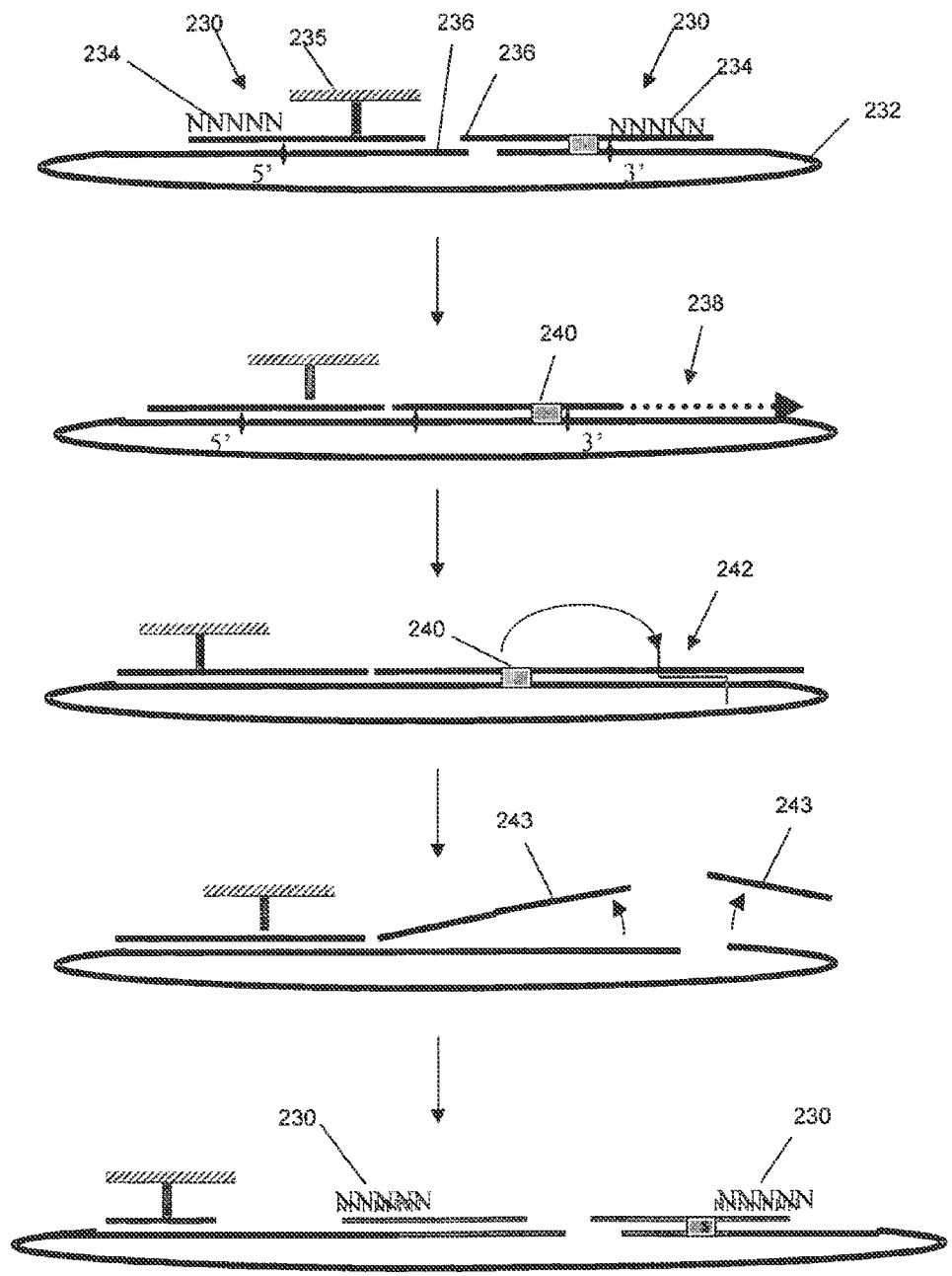

For mammalian-sized genomes, an initial fragmentation of genomic DNA can be achieved by digestion with one or more "rare" cutting restriction endonucleases, such as Not I, Asc I, Bae I, CspC I, Pac I, Fse I, Sap I, Sfi I, Psr I, or the like. The resulting fragments can be used directly, or for genomes that have been sequenced, specific fragments may be isolated from such digested DNA for subsequent processing as illustrated in FIG. 2B. Genomic DNA (230) is digested (232) with a rare cutting restriction endonuclease to generate fragments (234), after which the fragments (234) are further digested for a short period (i.e. the reaction is not allowed to run to completion) with a 5' single stranded exonuclease, such as 2 exonuclease, to expose sequences (237) adjacent to restriction site sequences at the end of the fragments. Such exposed sequences will be unique for each fragment. Accordingly, biotinylated primers (241) specific for the ends of desired fragments can be annealed to a capture oligonucleotide for isolation; or alternatively, such fragments can be annealed to a primer having a capture moiety, such as biotin, and extended with a DNA polymerase that does not have strand displacement activity, such as Taq polymerase Stoffel fragment. After such extension, the 3' end of primers (241) abut the top strand of fragments (242) such that they can be ligated to form a continuous strand. The latter approach may also be implemented with a DNA polymerase that does have strand displacement activity and replaces the top strand (242) by synthesis. In either approach, the biotinylated fragments may then be isolated (240) using a solid support (239) derivatized with streptavidin.

In another aspect, primer extension from a genomic DNA template is used to generate a linear amplification of selected sequences greater than 10 kilobases surrounding genomic regions of interest. For example, to create a population of defined-sized targets, 20 cycles of linear amplification is performed with a forward primer followed by 20 cycles with a reverse primer. Before applying the second primer, the first primer is removed with a standard column for long DNA purification or degraded if a few uracil bases are incorporated. A greater number of reverse strands are generated relative to forward strands resulting in a population of double stranded molecules and single stranded reverse strands. The reverse primer may be biotinylated for capture to streptavidin beads which can be heated to melt any double stranded homoduplexes from being captured. All attached molecules will be single stranded and representing one strand of the original genomic DNA.

The products produced can be fragmented to 0.2-2 kb in size, or more preferably, 0.3-0.6 kb in size (effectively releasing them from the solid support) and circularized for an RCR reaction. In one method of circularization, illustrated in FIG. 2A, after genomic DNA (200) is fragmented and denatured (202), single stranded DNA fragments (204) are first treated with a terminal transferase (206) to attach a poly dA tails (208) to 3-prime ends. This is then followed by ligation (212) of the free ends intra-molecularly with the aid of bridging oligonucleotide (210). that is complementary to the poly dA tail at one end and complementary to any sequence at the other end by virtue of a segment of degenerate nucleotides. Duplex region (214) of bridging oligonucleotide (210) contains at least a primer binding site for RCR and, in some embodiments, sequences that provide complements to a capture oligonucleotide, which may be the same or different from the primer binding site sequence, or which may overlap the primer binding site sequence. The length of capture oligonucleotides may vary widely, In one aspect, capture oligonucleotides and their complements in a bridging oligonucleotide have lengths in the range of from 10 to 100 nucleotides; and more preferably, in the range of from 10 to 40 nucleotides. In some embodiments, duplex region (214) may contain additional elements, such as an oligonucleotide tag, for example, for identifying the source nucleic acid from which its associated DNA fragment came. That is, in some embodiments, circles or adaptor ligation or concatemers from different source nucleic acids may be prepared separately during which a bridging adaptor containing a unique tag is used, after which they are mixed for concatemer preparation or application to a surface to produce a random array. The associated fragments may be identified on such a random array by hybridizing a labeled tag complement to its corresponding tag sequences in the concatemers, or by sequencing the entire adaptor or the tag region of the adaptor. Circular products (218) may be conveniently isolated by a conventional purification column, digestion of non-circular DNA by one or more appropriate exonucleases, or both.

As mentioned above, DNA fragments of the desired sized range, e.g. 50-600 nucleotides, can also be circularized using circularizing enzymes, such as CircLigase, as single stranded DNA ligase that circularizes single stranded DNA without the need of a template. CircLigase is used in accordance with the manufacturer's instructions (Epicentre, Madison, Wis.). A preferred protocol for forming single stranded DNA circles comprising a DNA fragment and one or more adapters is to use standard ligase such as T4 ligase for ligation an adapter to one end of DNA fragment and than to use CircLigase to close the circle, as described more fully below.

An exemplary protocol for generating a DNA circle comprising an adaptor oligonucleotide and a target sequence using T4 ligase. The target sequence is a synthetic oligo T1N (sequence: 5'-NNNNNNNNGCATANCACGANGTCAT-NATCGTNCAAACGTCAGTCCANGAATCNAGAT CCACTTAGANTGNCGNNNNNNNN-3') (SEQ ID NO: 1). The adaptor is made up of 2 separate oligos. The adaptor oligo that joins to the 5' end of T1N is BR2-ad (sequence: 5'-TAT-CATCTGGATGTTAGGAAGACAAAAG-GAAGCTGAGGACATTAACGGAC-3') (SEQ ID NO: 2) and the adaptor oligo that joins to the 3' end of T1N is UR3-ext (sequence: 5'-ACCTTCAGACCAGAT-3') (SEQ ID NO: 3) UR3-ext contains a type IIs restriction enzyme site (Acu I:

CTTCAG) to provide a way to linearize the DNA circular for insertion of a second adaptor. BR2-ad is annealed to BR2-temp (sequence 5'-NNNNNNNGTCCGTTAATGTCCT-CAG-3') (SEQ ID NO: 4) to form a double-stranded adaptor BR2 adaptor. UR3-ext is annealed to biotinylated UR3-temp (sequence 5'-[BIOTIN]ATCTGGTCTGAAGGT-NNNNNNN-3') (SEQ ID NO: 5) to form a double-stranded adaptor UR3 adaptor. 1 pmol of target T1N is ligated to 25 pmol of BR2 adaptor and 10 pmol of UR3 adaptor in a single ligation reaction containing 50 mM Tris-Cl, pH7.8, 10% PEG, 1 mM ATP, 50 mg/L BSA, 10 mM MgCl$_2$, 0.3 unit/µl T4 DNA ligase (Epicentre Biotechnologies, WI) and 10 mM DTT) in a final volume of 10 ul. The ligation reaction is incubated in a temperature cycling program of 15° C. for 11 min, 37° C. for 1 min repeated 18 times. The reaction is terminated by heating at 70° C. for 10 min. Excess BR2 adaptors are removed by capturing the ligated products with streptavidin magnetic beads (New England Biolabs, MA). 3.3 ul of 4× binding buffer (2M NaCl, 80 mM Tris HCl pH7.5) is added to the ligation reaction which is then combined with 15 µg of streptavidin magnetic beads in 1× binding buffer (0.5M NaCl, 20 mM Tris HCl pH7.5). After 15 min incubation in room temperature, the beads are washed twice with 4 volumes of low salt buffer (0.15M NaCl, 20 mM Tris HCl pH7.5). Elution buffer (10 mM Tris HCl pH7.5) is pre-warmed to 70 deg, 10 µl of which is added to the beads at 70° C. for 5 min. After magnetic separation, the supernatant is retained as primary purified sample. This sample is further purified by removing the excess UR3 adaptors with magnetic beads pre-bound with a biotinylated oligo BR-rc-bio (sequence: 5'-[BIOTIN]CTTTTGTCTTCCTAACATCC-3') (SEQ ID NO: 6) that is reverse complementary to BR2-ad similarly as described above. The concentration of the adaptor-target ligated product in the final purified sample is estimated by urea polyacrylamide gel electrophoresis analysis. The circularization is carried out by phosphorylating the ligation products using 0.2 unit/µl T4 polynucleotide kinase (Epicentre Biotechnologies) in 1 mM ATP and standard buffer provided by the supplier, and circularized with ten-fold molar excess of a splint oligo UR3-closing-88 (sequence 5'-AGAT-GATAATCTGGTC-3') (SEQ ID NO: 7) using 0.3 unit/µl of T4 DNA ligase (Epicentre Biotechnologies) and 1 mM ATP. The circularized product is validated by performing RCR reactions as described below.

Generating Polynucleotide Concatemers by Rolling Circle Replication

In one aspect of the invention, single molecules comprise concatemers of polynucleotides, usually polynucleotide analytes, i.e. target sequences, that have been produce in a conventional rolling circle replication (RCR) reaction. Guidance for selecting conditions and reagents for RCR reactions is available in many references available to those of ordinary skill, as evidence by the following that are incorporated by reference: Kool, U.S. Pat. No. 5,426,180; Lizardi, U.S. Pat. Nos. 5,854,033 and 6,143,495; Landegren, U.S. Pat. No. 5,871,921; and the like. Generally, RCR reaction components comprise single stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circles and be extended by the DNA polymerase to form concatemers of DNA circle complements. An exemplary RCR reaction protocol is as follows: In a 50 µL reaction mixture, the following ingredients are assembled: 2-50 pmol circular DNA, 0.5 units/µL phage φ29 DNA polymerase, 0.2 µg/µL BSA, 3 mM dNTP, 1×φ29 DNA polymerase reaction buffer (Amersham). The RCR reaction is carried out at 30° C. for 12 hours. In some embodiments, the concentration of circular DNA in the polymerase reaction may be selected to be low (approximately 10-100 billion circles per ml, or 10-100 circles per picoliter) to avoid entanglement and other intermolecular interactions.

Preferably, concatemers produced by RCR are approximately uniform in size; accordingly, in some embodiments, methods of making arrays of the invention may include a step of size-selecting concatemers. For example, in one aspect, concatemers are selected that as a population have a coefficient of variation in molecular weight of less than about 30%; and in another embodiment, less than about 20%. In one aspect, size uniformity is further improved by adding low concentrations of chain terminators, such ddNTPs, to the RCR reaction mixture to reduce the presence of very large concatemers, e.g. produced by DNA circles that are synthesized at a higher rate by polymerases. In one embodiment, concentrations of ddNTPs are used that result in an expected concatemer size in the range of from 50-250 Kb, or in the range of from 50-100 Kb. In another aspect, concatemers may be enriched for a particular size range using a conventional separation techniques, e.g. size-exclusion chromatography, membrane filtration, or the like.

Solid Phase Surfaces for Constructing Random Arrays

A wide variety of supports may be used with the invention. In one aspect, supports are rigid solids that have a surface, preferably a substantially planar surface so that single molecules to be interrogated are in the same plane. The latter feature permits efficient signal collection by detection optics, for example. In another aspect, solid supports of the invention are nonporous, particularly when random arrays of single molecules are analyzed by hybridization reactions requiring small volumes. Suitable solid support materials include materials such as glass, polyacrylamide-coated glass, ceramics, silica, silicon, quartz, various plastics, and the like. In one aspect, the area of a planar surface may be in the range of from 0.5 to 4 cm$^2$. In one aspect, the solid support is glass or quartz, such as a microscope slide, having a surface that is uniformly silanized. This may be accomplished using conventional protocols, e.g. acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface. e.g. Beattie et a (1995), Molecular Biotechnology, 4: 213. Such a surface is readily treated to permit end-attachment of capture oligonucleotides, e.g. by providing capture oligonucleotides with a 3' or 5' triethylene glycol phosphoryl spacer (see Beattie et al, cited above) prior to application to the surface. Many other protocols may be used for adding reactive functionalites to glass and other surfaces, as evidenced by the disclosure in Beaucage (cited above).

Whenever enzymatic processing is not required, capture oligonucleotides may comprise non-natural nucleosidic units and/or linkages that confer favorable properties, such as increased duplex stability; such compounds include, but not limited to, peptide nucleic acids (PNAs), locked nucleic acids (LNA), oligonucleotide N3'→P5' phosphoramidates, oligo-2'-O-alkylribonucleotides, and the like.

In embodiments of the invention in which patterns of discrete spaced apart regions are required, photolithography, electron beam lithography, nano imprint lithography, and nano printing may be used to generate such patterns on a wide variety of surfaces, e.g. Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference.

In one aspect, surfaces containing a plurality of discrete spaced apart regions are fabricated by photolithography. A commercially available, optically flat, quartz substrate is spin coated with a 100-500 nm thick layer of photo-resist. The photo-resist is then baked on to the quartz substrate. An image of a reticle with a pattern of regions to be activated is projected onto the surface of the photo-resist, using a stepper. After exposure, the photo-resist is developed, removing the areas of the projected pattern which were exposed to the UV source. This is accomplished by plasma etching, a dry developing technique capable of producing very fine detail. The substrate is then baked to strengthen the remaining photo-resist. After baking, the quartz wafer is ready for functionalization. The wafer is then subjected to vapor-deposition of 3-aminopropyldimethylethoxysilane. The density of the amino functionalized monomer can be tightly controlled by varying the concentration of the monomer and the time of exposure of the substrate. Only areas of quartz exposed by the plasma etching process may react with and capture the monomer. The substrate is then baked again to cure the monolayer of amino-functionalized monomer to the exposed quartz. After baking, the remaining photo-resist may be removed using acetone. Because of the difference in attachment chemistry between the resist and silane, aminosilane-functionalized areas on the substrate may remain intact through the acetone rinse. These areas can be further functionalized by reacting them with p-phenylenediisothiocyanate in a solution of pyridine and N—N-dimethlyformamide. The substrate is then capable of reacting with amine-modified oligonucleotides. Alternatively, oligonucleotides can be prepared with a 5'-carboxy-modifier-c10 linker (Glen Research). This technique allows the oligonucleotide to be attached directly to the amine modified support, thereby avoiding additional functionalization steps.

In another aspect, surfaces containing a plurality of discrete spaced apart regions are fabricated by nano-imprint lithography (NIL). For DNA array production, a quartz substrate is spin coated with a layer of resist, commonly called the transfer layer. A second type of resist is then applied over the transfer layer, commonly called the imprint layer. The master imprint tool then makes an impression on the imprint layer. The overall thickness of the imprint layer is then reduced by plasma etching until the low areas of the imprint reach the transfer layer. Because the transfer layer is harder to remove than the imprint layer, it remains largely untouched. The imprint and transfer layers are then hardened by heating. The substrate is then put into a plasma etcher until the low areas of the imprint reach the quartz. The substrate is then derivatized by vapor deposition as described above.

In another aspect, surfaces containing a plurality of discrete spaced apart regions are fabricated by nano printing. This process uses photo, imprint, or e-beam lithography to create a master mold, which is a negative image of the features required on the print head. Print heads are usually made of a soft, flexible polymer such as polydimethylsiloxane (PDMS). This material, or layers of materials having different properties, are spin coated onto a quartz substrate. The mold is then used to emboss the features onto the top layer of resist material under controlled temperature and pressure conditions. The print head is then subjected to a plasma based etching process to improve the aspect ratio of the print head, and eliminate distortion of the print head due to relaxation over time of the embossed material. Random array substrates are manufactured using nano-printing by depositing a pattern of amine modified oligonucleotides onto a homogenously derivatized surface. These oligo-nucleotides would serve as capture probes for the RCR products. One potential advantage to nano-printing is the ability to print interleaved patterns of different capture probes onto the random array support. This would be accomplished by successive printing with multiple print heads, each head having a differing pattern, and all patterns fitting together to form the final structured support pattern. Such methods allow for some positional encoding of DNA elements within the random array. For example, control concatemers containing a specific sequence can be bound at regular intervals throughout a random array.

In still another aspect, a high density array of capture oligonucleotide spots of sub micron size is prepared using a printing head or imprint-master prepared from a bundle, or bundle of bundles, of about 10,000 to 100 million optical fibers with a core and cladding material. By pulling and fusing fibers a unique material is produced that has about 50-1000 nm cores separated by a similar or 2-5 fold smaller or larger size cladding material. By differential etching (dissolving) of cladding material a nano-printing head is obtained having a very large number of nano-sized posts. This printing head may be used for depositing oligonucleotides or other biological (proteins, oligopeptides, DNA, aptamers) or chemical compounds such as silane with various active groups. In one embodiment the glass fiber tool is used as a patterned support to deposit oligonucleotides or other biological or chemical compounds. In this case only posts created by etching may be contacted with material to be deposited. Also, a flat cut of the fused fiber bundle may be used to guide light through cores and allow light-induced chemistry to occur only at the tip surface of the cores, thus eliminating the need for etching. In both cases, the same support may then be used as a light guiding/collection device for imaging fluorescence labels used to tag oligonucleotides or other reactants. This device provides a large field of view with a large numerical aperture (potentially >1). Stamping or printing tools that perform active material or oligonucleotide deposition may be used to print 2 to 100 different oligonucleotides in an interleaved pattern. This process requires precise positioning of the print head to about 50-500 nm. This type of oligonucleotide array may be used for attaching 2 to 100 different DNA populations such as different source DNA. They also may be used for parallel reading from sub-light resolution spots by using DNA specific anchors or tags. Information can be accessed by DNA specific tags, e.g. 16 specific anchors for 16 DNAs and read 2 bases by a combination of 5-6 colors and using 16 ligation cycles or one ligation cycle and 16 decoding cycles. This way of making arrays is efficient if limited information (e.g. a small number of cycles) is required per fragment, thus providing more information per cycle or more cycles per surface.

In one embodiment "inert" concatemers are used to prepare a surface for attachment of test concatemers. The surface is first covered by capture oligonucleotides complementary to the binding site present on two types of synthetic concatemers; one is a capture concatemer, the other is a spacer concatemer. The spacer concatemers do not have DNA segments complementary to the adapter used in preparation of test concatemers and they are used in about 5-50, preferably 10× excess to capture concatemers. The surface with capture oligonucleotide is "saturated" with a mix of synthetic concatemers (prepared by chain ligation or by RCR) in which the spacer concatemers are used in about 10-fold (or 5 to 50-fold)

excess to capture concatemers. Because of the ~10:1 ratio between spacer and capture concatemers, the capture concatemers are mostly individual islands in a sea of spacer concatemers. The 10:1 ratio provides that two capture concatemers are on average separated by two spacer concatemers. If concatemers are about 200 nm in diameter, then two capture concatemers are at about 600 nm center-to-center spacing. This surface is then used to attach test concatemers or other molecular structures that have a binding site complementary to a region of the capture concatemers but not present on the spacer concatemers. Capture concatemers may be prepared to have less copies than the number of binding sites in test concatemers to assure single test concatemer attachment per capture concatemer spot. Because the test DNA can bind only to capture concatemers, an array of test concatemers may be prepared that have high site occupancy without congregation. Due to random attachment, some areas on the surface may not have any concatemers attached, but these areas with free capture oligonucleotide may not be able to bind test concatemers since they are designed not to have binding sites for the capture oligonucleotide. An array of individual test concatemers as described would not be arranged in a grid pattern. An ordered grid pattern should simplify data collection because less pixels are needed and less sophisticated image analysis systems are needed also.

In one aspect, multiple arrays of the invention may be place on a single surface. For example, patterned array substrates may be produced to match the standard 96 or 384 well plate format. A production format can be an 8×12 pattern of 6 mm×6 mm arrays at 9 mm pitch or 16×24 of 3.33 mm×3.33 mm array at 4.5 mm pitch, on a single piece of glass or plastic and other optically compatible material. In one example each 6 mm×6 mm array consists of 36 million 250-500 nm square regions at 1 micrometer pitch. Hydrophobic or other surface or physical barriers may be used to prevent mixing different reactions between unit arrays.

By way of example, binding sites (i.e. discrete spaced apart regions) for DNA samples are prepared by silanization of lithographically defined sites on silicon dioxide on silicon, quartz, or glass surfaces with 3-aminopropyldimethylethoxysilane or similar silanization agent followed by derivatization with p-phenylenediisothiocyanate or similar derivatization agent. For example, the binding sites may be square, circular or regular/irregular polygons produced by photolithography, direct-write electron beam, or nano-imprint lithography. Minimization of non-specific binding in regions between binding site The wetability (hydrophobic v. hydrophilic) and reactivity of the field surrounding the binding sites can be controlled to prevent DNA samples from binding in the field; that is, in places other than the binding sites. For example, the field may be prepared with hexamethyldisilazane (HMDS), or a similar agent covalently bonded to the surface, to be hydrophobic and hence unsuitable to hydrophilic bonding of the DNA samples. Similarly, the field may be coated with a chemical agent such as a fluorine-based carbon compound that renders it unreactive to DNA samples.

For the three surface fabrication processes listed in the prior paragraph, the follow exemplary steps are followed. For photolithography:
1) Clean glass wafer
2) Prime surface with HMDS
3) Pattern binding sites in photoresist
4) Reactive ion etch binding site surface with oxygen to remove HMDS
5) Silanize with 0.3% 3-aminopropyldimethylethoxysilane
6) Coat with photoresist to protect wafer during sawing
7) Saw wafer into chips
8) Strip photoresist
9) Derivatize binding sites with solution of 10% pyridine and 90% N,N-Dimethylformamide (DMF) using 2.25 mg p-phenylenediisothiocyanate (PDC) per ml of solution for 2 h followed by methanol, acetone, and water rinses For direct write electron beam surface fabrication:
1) Clean glass wafer
2) Prime surface with HMDS
3) Pattern binding sites in PMMA with electron beam
4) Reactive ion etch binding site surface with oxygen to remove HMDS
5) Silanize with 0.3% 3-aminopropyldimethylethoxysilane
6) Coat with photoresist to protect wafer during sawing
7) Saw wafer into chips
8) Strip photoresist
9) Derivatize binding sites with solution of 10% pyridine and 90% N,N Dimethylformamide (DMF) using 2.25 mg p-phenylenediisothiocyanate (PDC) per ml of solution for 2 h followed by methanol, acetone, and water rinses.

For nano imprint lithography surface fabrication:
1) Clean glass wafer
2) Prime surface with HMDS
3) Coat wafer with transfer layer
4) Contact print pattern with nano imprint template and photopolymer on top of transfer layer
5) Dry etch pattern into transfer layer
6) Reactive ion etch binding site surface with oxygen to remove HMDS
7) Silanize with 0.3% 3-aminopropyldimethylethoxysilane
8) Coat with photoresist to protect wafer during sawing
9) Saw wafer into chips
10) Strip photoresist
11) Derivatize binding sites with solution of 10% pyridine and 90% N,N Dimethylformamide (DMF) using 2.25 mg p-phenylenediisothiocyanate (PDC) per ml of solution for 2 h followed by methanol, acetone, and water rinses.

As mentioned above, a glass surface may also be used for constructing random arrays of the invention. For example, a suitable glass surface may be constructed from microscope cover slips. Microscope cover slips (22 mm sq~170 um thick) are placed in Teflon racks. They are soaked in 3 molar KOH in 95% ethanol/water for 2 minutes. They are then rinsed in water, followed by an acetone rinse. This removes surface contamination and prepares the glass for silanization. Plasma cleaning is an alternative to KOH cleaning. Fused silica or quartz may also be substituted for glass. The clean, dry cover slips are immersed in 0.3% 3-aminopropyldimethylethoxysilane, 0.3% water, in acetone. They are left to react for 45 minutes. They are then rinsed in acetone and cured at 100° C. for 1 hour. 3-aminopropyldimethylethoxysilane may be used as a replacement for 3-aminopropyltriethoxysilane because it forms a mono-layer on the glass surface. The monolayer surface provides a lower background. The silanization agent may also be applied using vapor deposition. 3-aminopropyltriethoxysilane tends to form more of a polymeric surface when deposited in solution phase. The amino modified silane is then terminated with a thiocyanate group. This is done in a solution of 10% pyridine and 90% N,N-Dimethylformamide (DMF) using 2.25 mg p-phenylenediisothiocyanate (PDC) per ml of solution. The reaction is run for 2 hours, then the slide is washed in methanol, followed by acetone, and water rinses. The cover slips are then dried and ready to bind probe. There are additional chemistries that can be used to modify the amino group at the end of the silanization agent. For example, glutaraldehyde can be used to modify the amino group at the end of the silanization agent to a aldehyde group which can be coupled to an amino modified oligonucleotide.

Capture oligonucleotides are bound to the surface of the cover slide by applying a solution of 10-50 micromolar capture oligonucleotide in 100 millimolar sodium bicarbonate in water to the surface. The solution is allowed to dry, and is then washed in water. It may be beneficial to avoid terminating the 3-amino group with PDC and perform a direct conjugation (of the 3-amino end) to the capture oligonucleotide which has been modified with either a carboxyl group or an aldehyde group at the 5' end. In the case of the carboxyl group, the oligonucleotide is applied in a solution that contains EDC (1-Ethyl-3-(3-dimethylaminopropyl)-carbodiimide). In the case of the aldehyde group, the oligo is kept wet for 5-10 minutes then the surface is treated with a 1% solution of sodium borohydride.

In another aspect of the invention, random arrays are prepared using nanometer-sized beads. Sub-micron glass or other types of beads (e.g. in the 20-50 nm range) are used which are derivatized with a short oligonucleotide, e.g. 6-30 nucleotides, complementary to an adaptor oligonucleotide in the circles used to generate concatemers. The number of oligonucleotides on the bead and the length of the sequence can be controlled to weakly bind the concatemers in solution. Reaction rate of the beads should be much faster than that of the solid support alone. After binding concatemers, the beads are then allowed to settle on the surface of an array substrate. The array substrate has longer, more stable, more numerous oligonucleotides, such that conditions may be selected to permit preferential binding to the surface, thereby forming a spaced array of concatemers. If the beads are magnetic, a magnetic field can be used to pull them to the surface, it may also be used to move them around the surface. Alternatively, a centrifuge may be used to concentrate the beads on the surface. An exemplary protocol is as follows: 1. A preparation of 20 ul of concatemer solution with one million concatemers per 1 ul is mixed with 20 million nano-beads with about 500 capture oligonucleotides about 8 bases in length (6-16 bases may be use under different conditions). A 100 nm nano-bead there is approximately 40,000 nm2 and can hold up to 4000 short oligonucleotides. One way to control the density of capture probes is to mix in this case about 8 times more of a 2-4 bases long oligonucleotides with the same attachment chemistry with the capture probe. Also, much smaller nano-beads (20-50 nm) may be used. 2. Reaction conditions (temperature, pH, salt concentration) are adjusted so that concatemers with over 300 copies will attach to nanobeads in significant numbers. 3. The reaction is applied under the same stringent conditions to a support with 4×4 mm of patterned surface with 16 million active sites about 200 nm in size, and nanobeads are allowed or forced to settle on the substrate surface bringing large concatemers with them. The largest distance that a nano-bead-concatemer has to travel is about 1 mm. The vertical movement of beads minimizes number of potential concatemer-concatemer encounters. The reaction solution may be applied in aliquots, e.g. 4 applications 5 ul each. In this case the thickness of the applied solution (e.g. the nano-bead maximal travel distance) is only about 250 microns. 4. Further increase stringency of the reaction to release concatemers from nano-beads and attach them to active sites on the support with ~300 capture oligonucleotides 20-50 bases in length. 5. Concatemers attached to nano-beads will predominately settle initially between active sites on the support because there are 25 times more inactive than active surface. Slight horizontal movement force (e.g. substrate tilting, and other forces), may be applied to move nano-bead-concatemers about one to a few microns around.

Identification of Probe Sequences in Random Arrays

A variety of sequencing methodologies can be used to determine probe sequences of random arrays, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g. Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003), which are incorporated by reference, and ligation-based methods, e.g. Shendure et al (2005), Science, 309: 1728-1739, which is incorporated by reference.

Whenever probe sequences are individually synthesized, they may be associated with one or more decoder oligonucleotides, e.g. as sequences contiguous with a probe sequence used in the formation of a polynucleotide molecule. After deposition of polynucleotide molecules, probe sequences are identified by applying a sequence of combinatorial mixtures of labeled complements of the decoder probes (i.e. identifier probes), as disclosed in Gunderson et al, Genome Research, 14: 870-877 (2004); Epstein et al, J. Am. Chem. Soc., 125: 13753-13759 (2003); Kuhn et al, Genome Research, 14: 2347-2356 (2004); Gunderson and Chee, US. patent publication 2003/0096239; which references are incorporated herein by reference.

In one aspect, parallel sequencing of probe sequences on a random array is accomplished by combinatorial SBH (cSBH), as disclosed by Drmanac in the above-cited patents. In one aspect, a first and second sets of oligonucleotide probes are provide, wherein each sets has member probes that comprise oligonucleotides having every possible sequence for the defined length of probes in the set. For example, if a set contains probes of length six, then it contains 4096 (=$4^6$) probes. In another aspect, first and second sets of oligonucleotide probes comprise probes having selected nucleotide sequences designed to detect selected sets of target polynucleotides. Sequences are determined by hybridizing one probe or pool of probe, hybridizing a second probe or a second pool of probes, ligating probes that form perfectly matched duplexes on their target sequences, identifying those probes that are ligated to obtain sequence information about the target sequence, repeating the steps until all the probes or pools of probes have been hybridized, and determining the nucleotide sequence of the target from the sequence information accumulated during the hybridization and identification steps.

For sequencing operation, in some embodiments, the sets may be divided into subsets that are used together in pools, as disclosed in U.S. Pat. No. 6,864,052. Probes from the first and second sets may be hybridized to target sequences either together or in sequence, either as entire sets or as subsets, or pools. In one aspect, lengths of the probes in the first or second sets are in the range of from 5 to 10 nucleotides, and in another aspect, in the range of from 5 to 7 nucleotides, so that when ligated they form ligation products with a length in the range of from 10 to 20, and from 10 to 14, respectively.

In another aspect, using such techniques, the sequence identity of each attached DNA concatemer may be determined by a "signature" approach. About 50 to 100 or possibly 200 probes are used such that about 25-50% or in some applications 10-30% of attached concatemers will have a full match sequence for each probe. This type of data allows each amplified DNA fragment within a concatemer to be mapped to the reference sequence. For example, by such a process one can score 64 4-mers (i.e. 25% of all possible 256 4-mers) using 16 hybridization/stripoff cycles in a 4 colors labeling schema. On a 60-70 base fragment amplified in a concatemer about 16 of 64 probes will be positive since there are 64 possible 4mers present in a 64 base long sequence (i.e. one quarter of all possible 4mers). Unrelated 60-70 base fragments will have a very different set of about 16 positive decoding probes. A combination of 16 probes out of 64 probes has a random chance of occurrence in 1 of every one billion fragments which practically provides a unique signature for that concatemer. Scoring 80 probes in 20 cycles and generating 20 positive probes create a signature even more likely to be unique: occurrence by chance is 1 in billion billions. Previously, a "signature" approach was used to select novel genes from cDNA libraries. An implementation of a signature approach is to sort obtained intensities of all tested probes and select up to a predefined (expected) number of probes that satisfy the positive probe threshold. These probes will be mapped to sequences of all DNA fragments (sliding window of a longer reference sequence may be used) expected to be present in the array. The sequence that has all or a statistically sufficient number of the selected positive probes is assigned as the sequence of the DNA fragment in the given concatemer. In another approach an expected signal can be defined for all used probes using their pre measured full match and mismatch hybridization/ligation efficiency. In this case a measure similar to the correlation factor can be calculated.

A preferred way to score 4-mers is to ligate pairs of probes, for example: $N_{(5-7)}BBB$ with $BN_{(7-9)}$, where B is the defined base and N is a degenerate base. For generating signatures on longer DNA concatemer probes, more unique bases will be used. For example, a 25% positive rate in a fragment 1000 bases in length would be achieved by $N_{(4-6)}BBBB$ and $BBN_{(6-8)}$. Note that longer fragments need the same number of about 60-80 probes (15-20 ligation cycles using 4 colors).

In one embodiment all probes of a given length (e.g. 4096 $N_{2-4}BBBBBBN_{2-4}$) or all ligation pairs may be used to determine complete sequence of the DNA in a concatemer. For example, 1024 combinations of $N_{(5-7)}B_3$ and $BBN_{(6-8)}$ may be scored (256 cycles if 4 colors are used) to determine sequence of DNA fragments of up to about 250 bases, preferably up to about 100 bases.

The decoding of sequencing probes with large numbers of Ns may be prepared from multiple syntheses of subsets of sequences at degenerated bases to minimize difference in the efficiency. Each subset is added to the mix at a proper concentration. Also, some subsets may have more degenerated positions than others. For example, each of 64 probes from the set $N_{(5-7)}BBB$ may be prepared in 4 different synthesis. One is regular all 5-7 bases to be fully degenerated; second is N0-3(A,T)5BBB; third is N0-2(A,T)(G,C)(A,T)(G,C)(A,T) BBB, and the fourth is N0-2(G,C)(A,T)(G,C)(A,T)(G,C) BBB.

Oligonucleotide preparation from the three specific syntheses is added in to regular synthesis in experimentally determined amounts to increase hybrid generation with target sequences that have in front of the BBB sequence an AT rich (e.g. AATAT) or (A or T) and (G or C) alternating sequence (e.g. ACAGT or GAGAC). These sequences are expected to be less efficient in forming a hybrid. All 1024 target sequences can be tested for the efficiency to form hybrid with $N_{0-3}BBB$ probes and those types that give the weakest binding may be prepared in about 1-10 additional synthesis and added to the basic probe preparation.

Decoding by Signatures: a smaller number of probes for small number of distinct samples: 5-7 positive out of 20 probes (5 cycles using 4 colors) has capacity to distinct about 10-100 thousand distinct fragments Decoding of 8-20mer RCR products. In this application arrays are formed as random distributions of unique 8 to 20 base recognition sequences in the form of DNA concatemers. The probes need to be decoded to determine the sequence of the 8-20 base probe region. At least two options are available to do this and the following example describes the process for a 12 mer. In the first, one half of the sequence is determined by utilizing the hybridization specificity of short probes and the ligation specificity of fully matched hybrids. Six to ten bases adjacent to the 12 mer are predefined and act as a support for a 6mer to 10-mer oligonucleotide. This short 6mer will ligate at its 3-prime end to one of 4 labeled 6-mers to 10-mers. These decoding probes consist of a pool of 4 oligonucleotides in which each oligonucleotide consists of 4-9 degenerate bases and 1 defined base. This oligonucleotide will also be labeled with one of four fluorescent labels. Each of the 4 possible bases A, C, G, or T will therefore be represented by a fluorescent dye. For example these 5 groups of 4 oligonucleotides and one universal oligonucleotide (Us) can be used in the ligation assays to sequence first 5 bases of 12-mers: B=each of 4 bases associated with a specific dye or tag at the end:

UUUUUUUU.BNNNNNNN*

UUUUUUUU.NBNNNNNN

UUUUUUUU.NNBNNNNN

UUUUUUUU.NNNBNNNN

UUUUUUUU.NNNNBNNN

Six or more bases can be sequences with additional probe pools. To improve discrimination at positions near the center of the 12mer the 6mer oligonucleotide can be positioned further into the 12mer sequence. This will necessitate the incorporation of degenerate bases into the 3-prime end of the non-labeled oligonucleotide to accommodate the shift. This is an example of decoding probes for position 6 and 7 in the 12-mer.

UUUUUUNN.NNNBNNNN

UUUUUUNN.NNNNBNNN

In a similar way the 6 bases from the right side of the 12mer can be decoded by using a fixed oligonucleotide and 5-prime labeled probes. In the above described system 6 cycles are required to define 6 bases of one side of the 12mer. With redundant cycle analysis of bases distant to the ligation site this may increase to 7 or 8 cycles. In total then, complete sequencing of the 12mer could be accomplished with 12-16 cycles of ligation. Partial or complete sequencing of arrayed DNA by combining two distinct types of libraries of detector probes. In this approach one set has probes of the general type $N_{3-8}B_{4-6}$ (anchors) that are ligated with the first 2 or 3 or 4 probes/probe pools from the set $BN_{6-8}$, $NBN_{5-7}$, $N_2BN_{4-6}$, and $N_3BN_{3-5}$. The main requirement is to test in a few cycles a probe from the first set with 2-4 or even more probes from the second set to read longer continuous sequence such as 5−6+3−4=8−10 in just 3-4 cycles. In one example, the process is:

1) Hybridize 1-4 4-mers or more 5-mer anchors to obtain 70-80% 1 or 2 anchors per DNA. One way to discriminate which anchor is positive from the pool is to mix specific probes with distinct hybrid stability (maybe different number of Ns in addition). Anchors may be also tagged to determine which anchor from the pool is hybridized to a spot. Tags, as additional DNA segment, may be used for adjustable displacement as a detection method. For example, EEEEEEENNNAAAAA and FFFFFFFFNNNCCCCC probes can be after hybridization or hybridization and ligation differentially removed with two corresponding displacers: EEEEEEENNNNN and FFFFFFFFNNNNNNNN where the second is more efficient. Separate cycles may be used just to determine which anchor is positive. For this purpose anchors labeled or tagged with multiple colors may be ligated to unlabeled N7-N10 supporter oligonucleotides.

2) Hybridize BNNNNNNNN probe with 4 colors corresponding to 4 bases; wash discriminatively (or displace by complement to the tag) to read which of two scored bases is associated to which anchor if two anchors are positive in one DNA. Thus, two 7-10 base sequences can be scores at the same time.

In 2-4 cycles extend to 4-6 base anchor for additional 2-4 bases run 16 different anchors per each array (32-64 physical cycles if 4 colors are used) to determine about 16 possible 8-mers (~100 bases total) per each fragment (more then enough to map it to the reference (probability that a 100-mer will have a set of 10 8-mers is less than 1 in trillion trillions; (10exp-28). By combining data from different anchors scored in parallel on the same fragment in another array complete sequence of that fragment and by extension to entire genomes may be generated from overlapping 7-10-mers.

Tagging probes with DNA tags for larger multiplex of decoding or sequence determination probes Instead of directly labeling probes they can be tagged with different oligonucleotide sequences made of natural bases or new synthetic bases (such as isoG and isoC). Tags can be designed to have very precise binding efficiency with their anti-tags using different oligonucleotide lengths (about 6-24 bases) and/or sequence including GC content. For example 4 different tags may be designed that can be recognized with specific anti-tags in 4 consecutive cycles or in one hybridization cycle followed by a discriminative wash. In the discriminative wash initial signal is reduced to 95-99%, 30-40%, 10-20% and 0-5% for each tag, respectively. In this case by obtaining two images 4 measurements are obtained assuming that probes with different tags will rarely hybridize to the same dot. Another benefit of having many different tags even if they are consecutively decoded (or 2-16 at a time labeled with 2-16 distinct colors) is the ability to use a large number of individually recognizable probes in one assay reaction. This way a 4-64 times longer assay time (that may provide more specific or stronger signal) may be affordable if the probes are decoded in short incubation and removal reactions.

The decoding process requires the use of 48-96 or more decoding probes. These pools will be further combined into 12-24 or more pools by encoding them with four fluorophores, each having different emission spectra. Using a 20× objective, each 6 mm×6 mm array may require roughly 30 images for full coverage by using a 10 mega pixel camera with. Each of 1 micrometer array areas is read by about 8 pixels. Each image is acquired in 250 milliseconds, 150 ms for exposure and 100 ms to move the stage. Using this fast acquisition it will take ~7.5 seconds to image each array, or 12 minutes to image the complete set of 96 arrays on each substrate. In one embodiment of an imaging system, this high image acquisition rate is achieved by using four ten-megapixel cameras, each imaging the emission spectra of a different fluorophore. The cameras are coupled to the microscope through a series of dichroic beam splitters. The autofocus routine, which takes extra time, runs only if an acquired image is out of focus. It will then store the Z axis position information to be used upon return to that section of that array during the next imaging cycle. By mapping the autofocus position for each location on the substrate we will drastically reduce the time required for image acquisition.

Each array requires about 12-24 cycles to decode. Each cycle consists of a hybridization, wash, array imaging, and strip-off step. These steps, in their respective orders, may take for the above example 5, 2, 12, and 5 minutes each, for a total of 24 minutes each cycle, or roughly 5-10 hours for each array, if the operations were performed linearly. The time to decode each array can be reduced by a factor of two by allowing the system to image constantly. To accomplish this, the imaging of two separate substrates on each microscope is staggered. While one substrate is being reacted, the other substrate is imaged.

An exemplary decoding cycle using cSBH includes the following steps: (i) set temperature of array to hybridization temperature (usually in the range 5-25° C.); (ii) use robot pipetter to pre mix a small amount of decoding probe with the appropriate amount of hybridization buffer; (iii) pipette mixed reagents into hybridization chamber; (iv) hybridize for predetermined time; (v) drain reagents from chamber using pump (syringe or other); (vi) add a buffer to wash mismatches of non-hybrids; (vii) adjust chamber temperature to appropriate wash temp (about 10-40° C.); (viii) drain chamber; (ix) add more wash buffer if needed to improve imaging; (x) image each array, preferably with a mid power (20×) microscope objective optically coupled to a high pixel count high sensitivity ccd camera, or cameras; plate stage moves chambers (or perhaps flow-cells with input funnels) over object, or objective-optics assembly moves under chamber; certain optical arrangements, using di-chroic mirrors/beam-splitters can be employed to collect multi-spectral images simultaneously, thus decreasing image acquisition time; arrays can be imaged in sections or whole, depending on array/image size/pixel density; sections can be assembled by aligning images using statistically significant empty regions pre-coded onto substrate (during active site creation) or can be made using a multi step nano-printing technique, for example sites (grid of activated sites) can be printed using specific capture probe, leaving empty regions in the grid; then print a different pattern or capture probe in that region using separate print head; (xi) drain chamber and replace with probe strip buffer (or use the buffer already loaded) then heat chamber to probe stripoff temperature (60-90° C.); high pH buffer may be used in the strip-off step to reduce stripoff temperature; wait for the specified time; (xii) remove buffer; (xiii) start next cycle with next decoding probe pool in set.

Probe Identification by Interspersed Adaptors

In some embodiments, the number of nucleotides that must be determined in order to identify probe sequences may be higher than the expected read-length of most sequencing methods, such as those mentioned above. In such cases, probe sequences in a random array may be analyzed by use of multiple adaptors interspersed at known locations within each probe. Such adaptors are referred to herein as "interspersed adaptors." Interspersed adaptors may serve as platforms for interrogating adjacent sequences using various sequencing chemistries, such as those that identify nucleotides by primer extensions, probe ligations, and the like. In one aspect, sequencing probe sequences by interspersed adaptors comprises the steps of: (a) generating a plurality of interspersed adaptors within a probe sequence, each interspersed adaptor having at least one boundary with the probe sequence; and (b) determining the identity of at least one nucleotide adjacent to at least one boundary of at least two interspersed adaptors, thereby determining a nucleotide sequence of the probe sequence. In another aspect, random arrays of probe sequences having interspersed adaptors are constructed in the following steps: (a) generating an amplicon from each of a plurality of probe sequences, each probe sequence containing a plurality of interspersed adaptors at predetermined sites, and each amplicon comprising multiple copies of a probe sequence and the amplicons including a number of probe sequences; (b) forming a random array of amplicons fixed to a surface at a density such that at least a majority of the amplicons are optically resolvable; (c) hybridizing one or more sequencing probes to the random array under conditions that permit the formation of perfectly matched duplexes between the one or more probes and complementary sequences on interspersed adaptors; (d) determining the identity of at least one nucleotide adjacent to at least one interspersed adaptor by extending the one of more sequencing probes in a sequence specific reaction; and (e) repeating steps (c) and (d) until a nucleotide sequence of the probe sequence is determined In one aspect, using interspersed adaptors with probe sequences addresses the problems associated with short sequence read-lengths produced by many approaches to large-scale DNA sequencing, including the problem of obtaining limited sequence information per enzymatic cycle.

In accordance with the invention, probe sequences are provided that have interspersed adaptors that permit acquisition of sequence information from multiple sites, either consecutively or simultaneously. As mentioned above, interspersed adaptors are oligonucleotides that are inserted at spaced locations within the interior region of a probe sequence. In another aspect, a plurality of interspersed adaptors are inserted at intervals within a contiguous region of a probe sequence. In some cases, such intervals have predetermined lengths, which may or may not be equal. In other cases, the spacing between interspersed adaptors may be known only to an accuracy of from one to a few nucleotides (e.g. from 1 to 15), or from one to a few tens of nucleotides (e.g. from 10 to 40), or from one to a few hundreds of nucleotides (e.g. from 100 to 200). Preferably, the ordering and number of interspersed adaptors within each probe sequence is known.

Interspersed adaptors may vary widely in length, which depends in part on the number and type of functional elements desired. Such functional elements may include primer binding sites, recognition sites for nucleases, such as nicking enzymes, restriction endonucleases, and the like, that may be employed in processing probe sequences. In one aspect, interspersed adaptors each have a length in the range of from 8 to 60 nucleotides; or in another aspect, they have a length in the range of from 8 to 32 nucleotides; in another aspect, they have a length in the range of from 20 to 100 nucleotides. The number of interspersed adaptors inserted into probe sequences may vary widely also and depends on a number of factors, including the sequencing chemistry being used (and its read-length capacity), the number of nucleotides desired to be identified within each probe sequence, whether amplification steps are employed between insertions, and the like. In one aspect, a plurality of interspersed adaptors are inserted at sites in a contiguous segment of a target polynucleotide; in another aspect, a plurality of three or more interspersed adaptors are inserted at sites in a contiguous segment of a probe sequence; in another aspect, a plurality of four or more interspersed adaptors are inserted at sites in a contiguous segment of a probe sequence; in still another aspect, a number of interspersed adaptors are inserted into a probe sequence that is selected from the range of from 2 to 10; or in the range of from 2 to 4; or in the range of from 3 to 6; or in the range of from 3 to 4; or in the range of from 4 to 6. In another aspect, interspersed adaptors may be inserted in one or both polynucleotide segments of a longer polynucleotide, e.g., 0.4-4 kb in length, that have been ligated together directly or indirectly in a circularization operation (referred to herein as a "mate-pair"). In one aspect, such polynucleotide segments may be 4-400 (preferably 10-100) bases long.

Figure 1E:
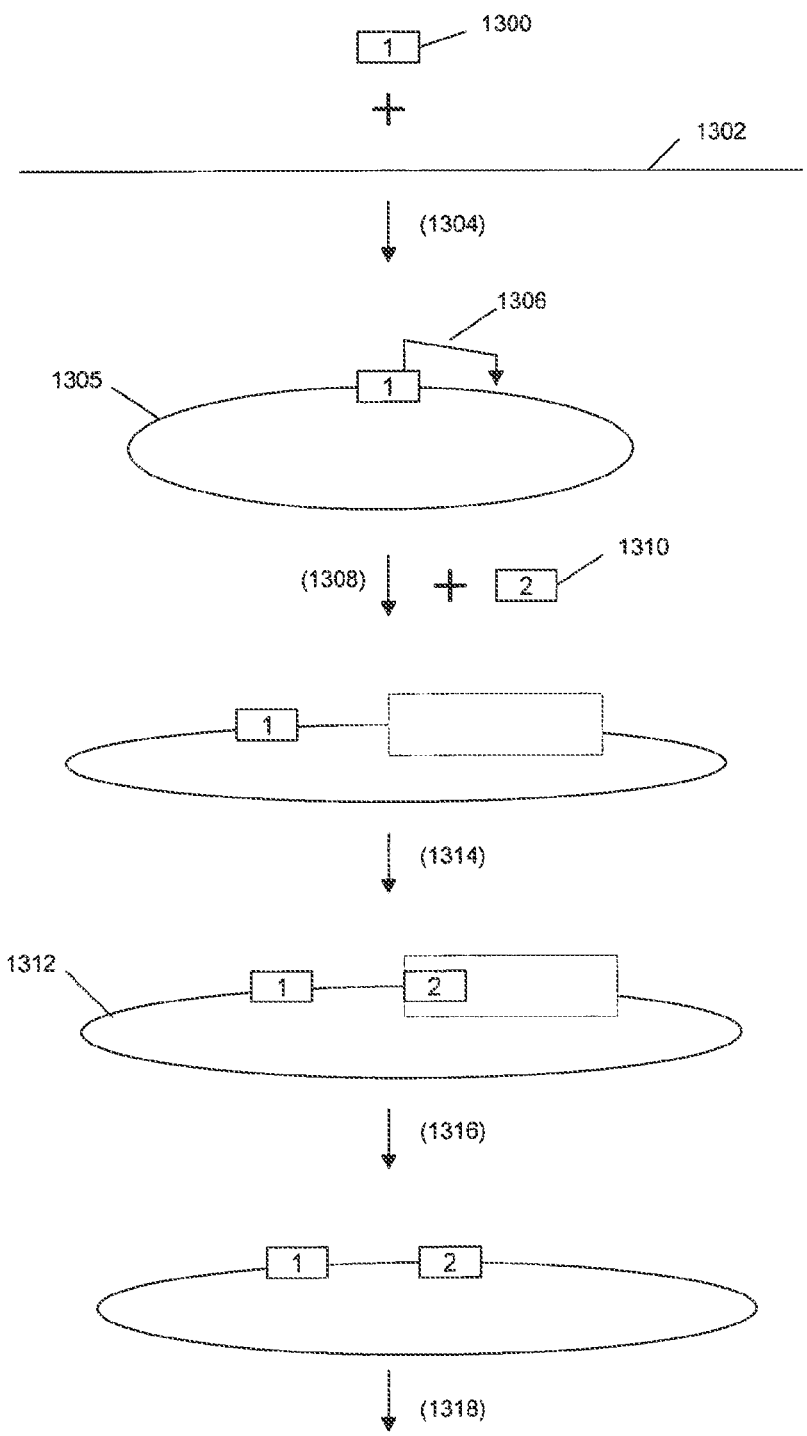
Figure 1F:
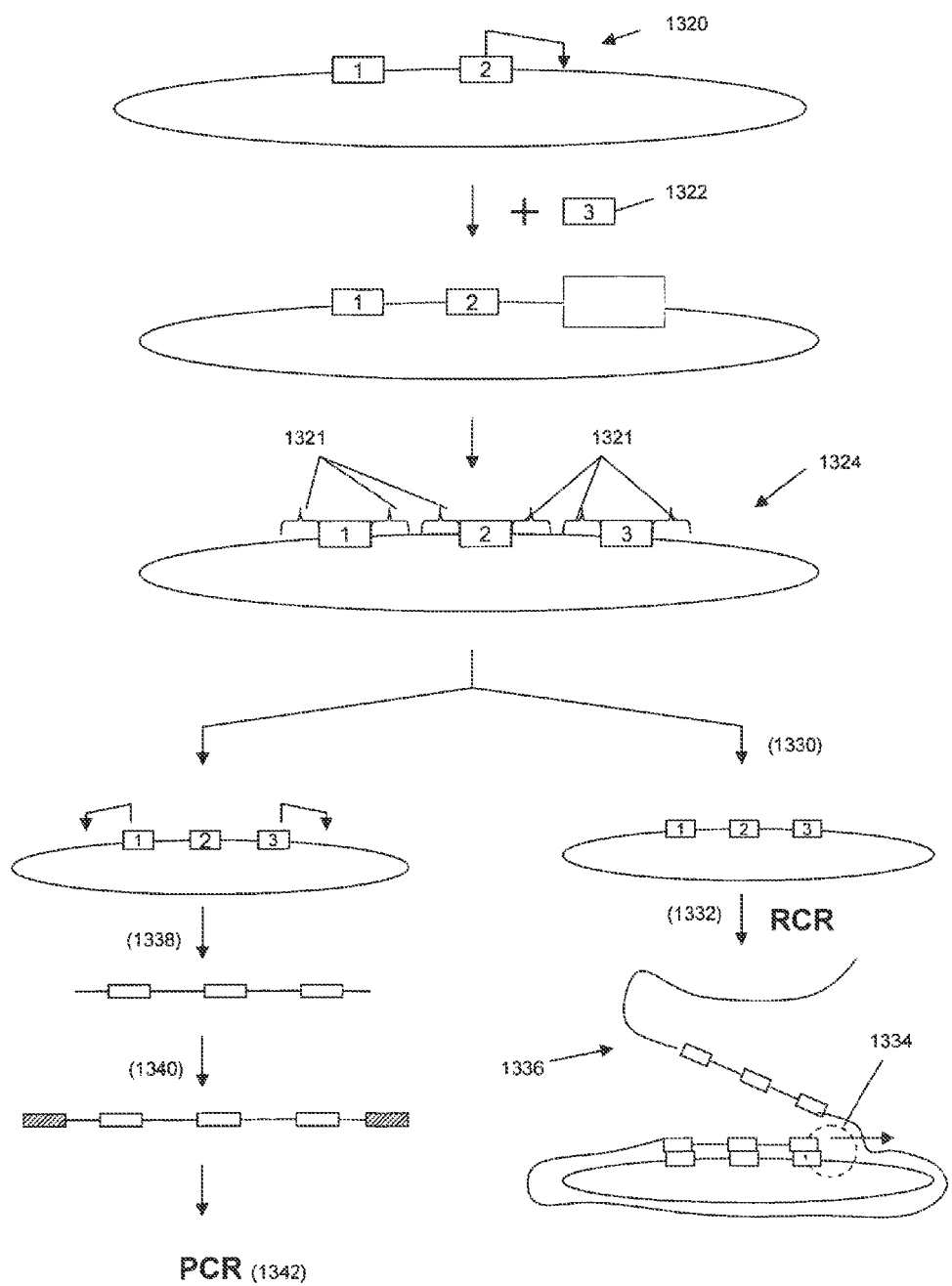
Figure 1G:
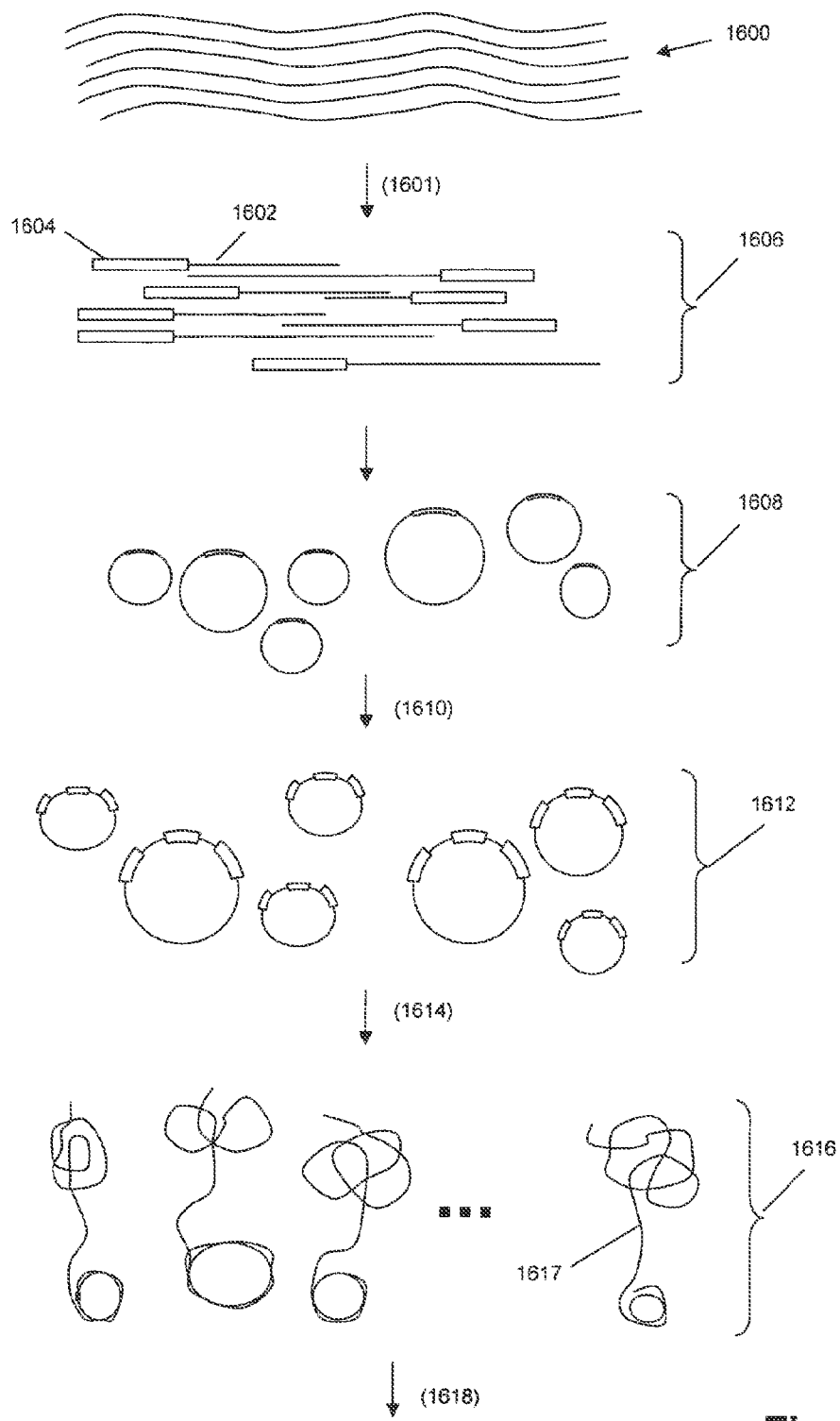
Figure 1H:
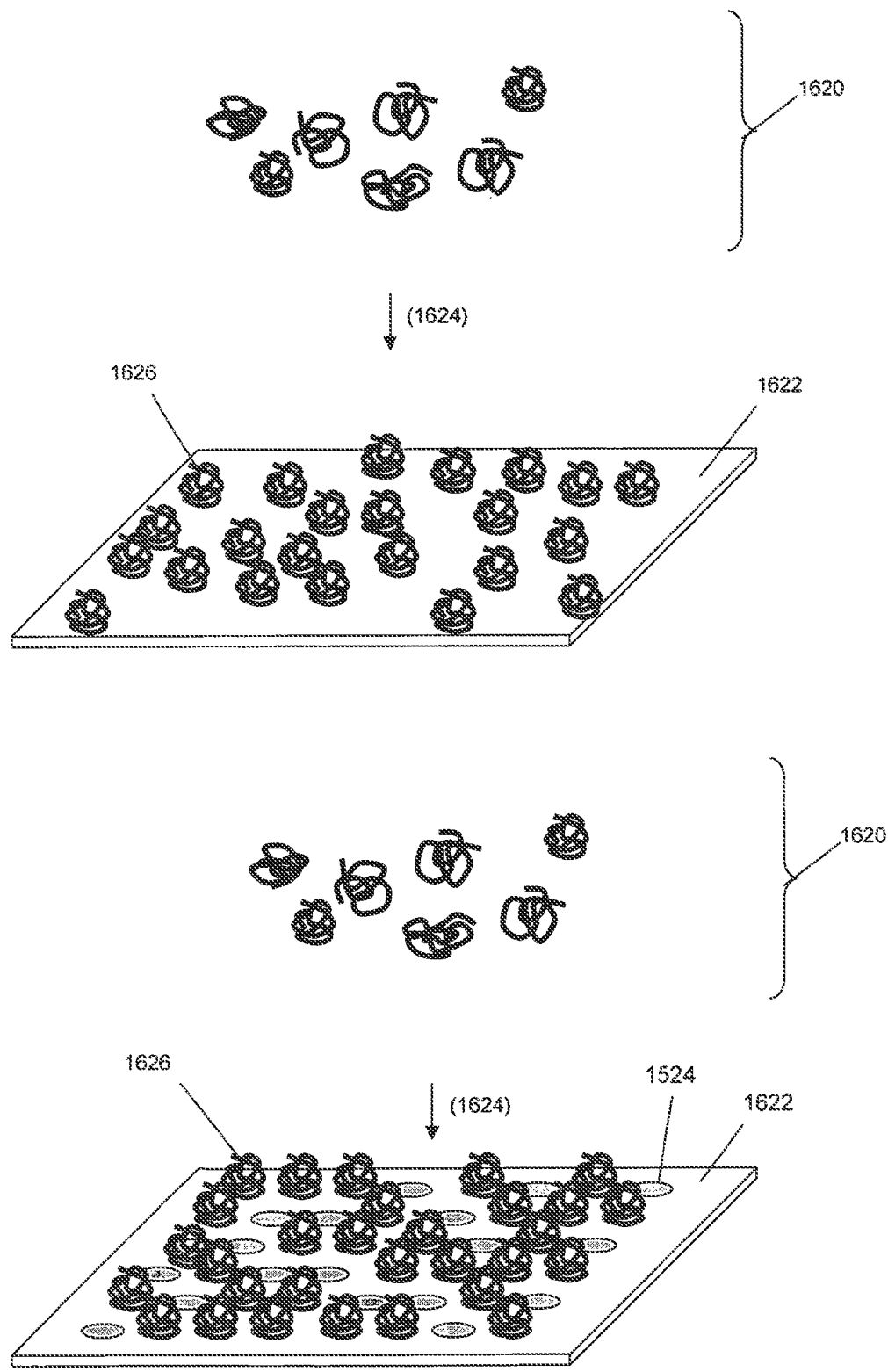
Figure 1L:
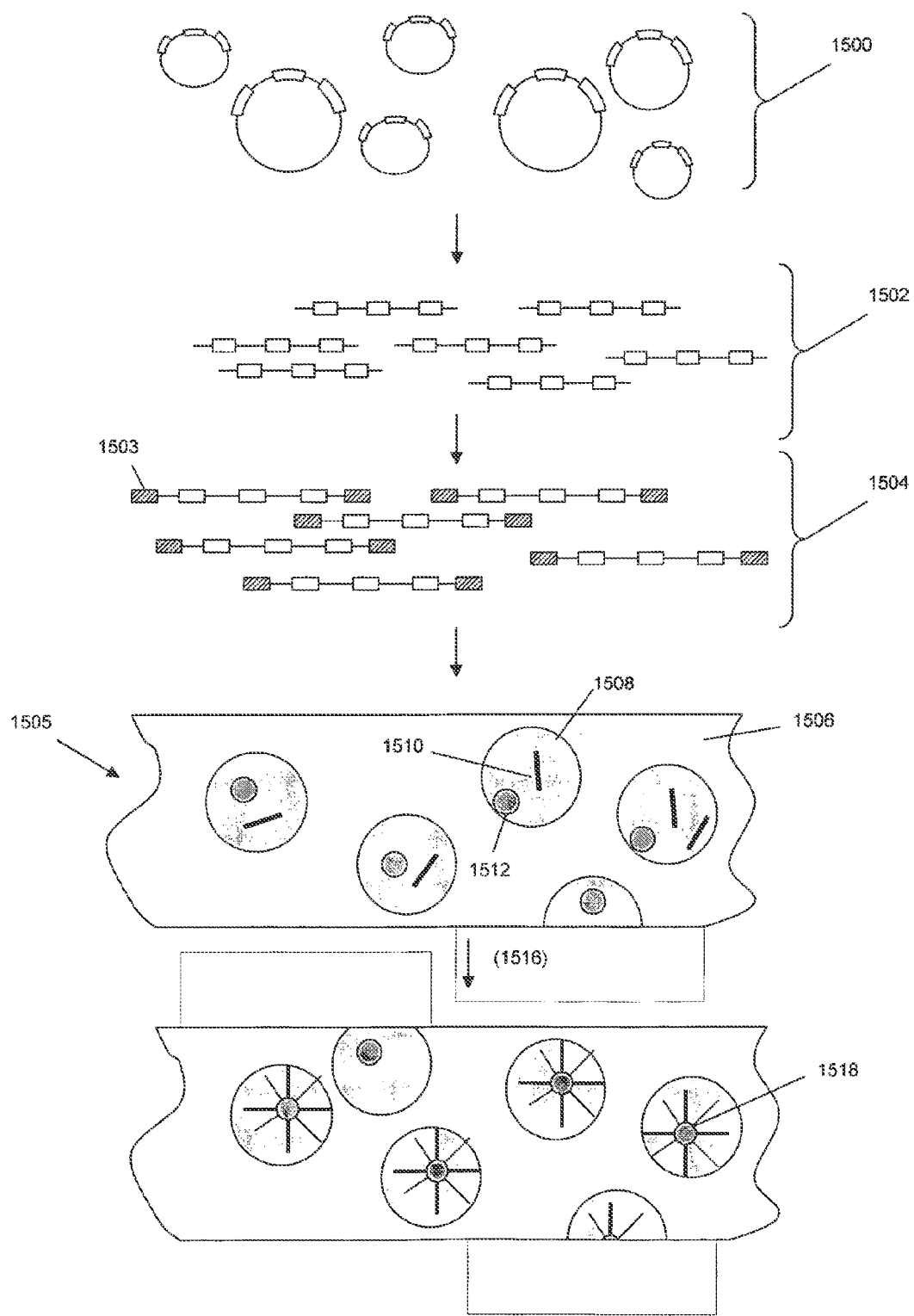

One aspect of the invention, a probe sequence having interspersed adaptors may be produced as illustrated diagrammatically in FIGS. 1E-1F. Probe sequence (1302) is combined with adaptor (1300), which may or may not be an interspersed adaptor, to form (1304) circle (1305), which may be either single stranded or double stranded. Usually, probe sequences are obtained from larger pieces of DNA, such as chromosomal or other genomic DNA or cDNAs after fragmentation. If double stranded DNA is used, then the ends of the fragments may be prepared for circularization by "polishing" and optional ligation of adaptors using conventional techniques, such as employed in conventional shotgun sequencing, e.g. Bankier, Methods Mol. Biol., 167: 89-100 (2001); Roe, Methods Mol. Biol., 255: 171-185 (2004); and the like. In order to generate the next site for inserting a second interspersed adaptor, circle (1305) is usually rendered double stranded, at least temporarily. Adaptor (1300) is usually designed to include a recognition site of a type IIs restriction endonuclease, which is oriented so that its cleavage site (1306) is interior to the probe sequence, shown, for example, to the right of adaptor (1300), thereby opening (1308) circle (1305). Usually, type IIs restriction endonucleases are selected which have cleavage sites separated from their recognition sites by at least six nucleotides (i.e. the number of nucleotides between the end of the recognition site and the closest cleavage point). Exemplary type IIs restriction endonucleases include, but are not limited to, Eco57M I, Mme I, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, or the like. In one aspect, as described more fully below, type IIs restriction endonucleases that leave 3' protruding strands after cleavage are preferred. For less precise insertion nicking enzyme may be used or one strand of the first adaptor may be disabled from ligation, thus creating a nick that can be translated at an approximate distance and used to initiate polynucleotide cutting.

After such cleavage, interspersed adaptor (1310) is ligated into place using conventional techniques to produce open circle (1312) containing two adaptors, which is then closed (1316) by ligation. Typically, sequences of a probe sequence are analyzed at or adjacent to one or both of the boundaries (e.g. 1321) between each interspersed adaptor and the probe sequence. The process is then repeated (1318): cleaving, inserting, and closing, until a desired number of interspersed adaptors are inserted (1326) into probe sequence (1302), such as three as shown in FIG. 1B. The final circle (1324) containing the interspersed adaptors may then be processed in a number of ways to obtain sequence information at sites in the target polynucleotide adjacent to at least one boundary of each interspersed adaptor. In one aspect, final circle (1324), or a segment of it, may be amplified to generate an amplicon that is analysed by a selected sequencing chemistry, such as one based on ligation or sequencing-by-synthesis. In one aspect, the first and last interspersed adaptors may be selected so that the region of final circle (1324) containing the interspersed adaptors can be cleaved (1338) from the circle, after which adaptors are ligated (1340) for amplification by polymerase chain reaction (PCR). Cleavage of the circle may be performed on one or two sites outside of the adaptors 1 and 3. In another aspect, final circle (1324) may be used directly to generate amplicons by rolling circle replication (RCR).

Figure 1J:
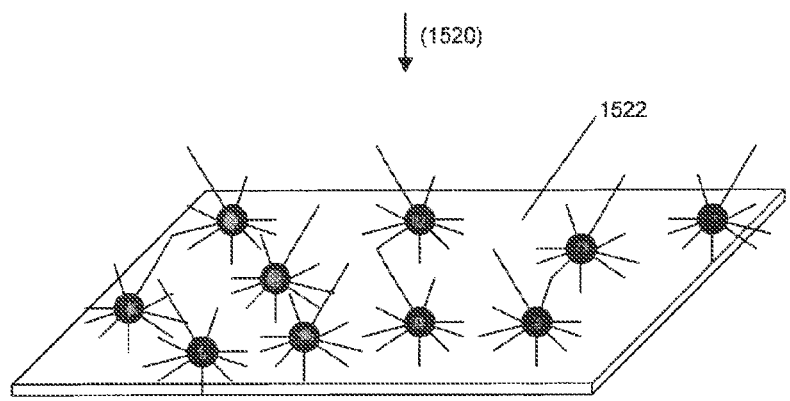
Figure 1K:
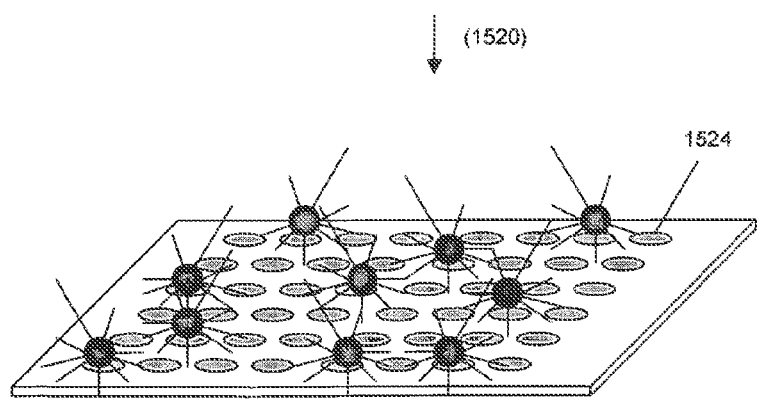

When many different probe sequences are analyzed in parallel, probe sequences having interspersed adaptors may be amplified using RCR or emulsion PCR as shown in FIGS. 1C-1D and FIGS. 1I-1K, respectively. A mixture of fragments may be amplified using emulsion PCR, e.g. as disclosed by Margulies et al, Nature, 437: 376-380 (2005); Shendure et al (2005), Science, 309: 1728-1732; Berka et al, U.S. patent publication 2005/0079510; Church et al, PCT publication WO 2005/082098; Nobile et al, U.S. patent publication 2005/0227264; Griffiths et al, U.S. Pat. No. 6,489,103; Tillett et al, PCT publication WO 03/106678; Kojima et al, Nucleic Acids Research, 33 (17): e150 (2005); Dressman et al, Proc. Natl. Acad. Sci., 100: 8817-8822 (2003); Mitra et al, Anal. Biochem., 320: 55-65 (2003); Musyanovych et al, Biomacromolecules, 6: 1824-1828 (2005); Li et al, Nature Methods, 3: 95-97 (2006); and the like, which are incorporated herein by reference. Briefly, going to FIG. 1I, after isolation of DNA circles (1500) comprising probe sequences with interspersed adaptors, the adaptors are excised, e.g. as shown in FIG. 1E (1038), to form a population of excised sequences, which are then ligated to adaptors (1503). The adaptored sequences are combined in a water-oil emulsion (1505) with primers specific for an adaptor at one end, beads having attached primers specific for an adaptor at the other end, and a DNA polymerase. Conditions are selected that permit a substantial number (e.g. greater than 15-20 percent) of aqueous bubbles (1508) in oil (1506) to contain a single adaptored sequence (1510) and at least one bead (1512). The aqueous phase in bubbles (1508) otherwise contain a conventional reaction mixture for conduction PCR, which results in beads (1518) each having a clonal population of a distinct adaptored sequence attached. After breaking emulsion (1505), beads containing clones of the adaptored sequences may be arrayed (1520) on a solid surface (1522) for sequence analysis. Such array of beads may be random, as illustrated in FIG. 1J, where the locations of the beads are not determined prior to arraying, or the array may be in accordance with a predetermined pattern of binding sites (1524), even though the distribution of beads on such sites is randomly determined. Both of such distributions are referred to herein as "random arrays."

In another aspect, the invention provides methods and compositions for generating concatemers of a plurality of probe sequences containing interspersed adaptors. In one embodiment, such concatemers may be generated by RCR, as described below and illustrated in FIGS. 1G-1K. Source nucleic acid (1600) (which may be, or contain, a single or several probe sequences) is treated (1601) to form single stranded fragments (1602), preferably in the range of from 50 to 600 nucleotides, and more preferably in the range of from 300 to 600 nucleotides, which are then ligated to adaptor oligonucleotides (1604) to form a population of adaptor-fragment conjugates (1606). Adaptor (1604) is usually an initial interspersed adaptor. Source nucleic acid (1600) may be genomic DNA extracted from a sample using conventional techniques, or a cDNA or genomic library produced by conventional techniques, or synthetic DNA, or the like. Treatment (1601) usually entails fragmentation by a conventional technique, such as chemical fragmentation, enzymatic fragmentation, or mechanical fragmentation, followed by denaturation to produce single stranded DNA fragments. Adaptor oligonucleotides (1604), in this example, are used to form (1608) a population of DNA circles by the method illustrated in FIG. 2A. In one aspect, each member of population (1608) has an adaptor with an identical anchor probe binding site and type IIs recognition site attached to a DNA fragment from source nucleic acid (1600). The adaptor also may have other functional elements including, but not limited to, tagging sequences, sequences for attachment to a solid surface, restriction sites, functionalization sequences, and the like. In other embodiments, classes of DNA circles may be created by providing adaptors having different anchor probe binding sites. After DNA circles (1608) are formed, further interspersed adaptors are inserted as described generally above to form circles (1612) containing interspersed adaptors. To these circles, a primer and rolling circle replication (RCR) reagents are added to generate (1614) in a conventional RCR reaction a population (1616) of concatemers (1617) of the complements of the adaptor oligonucleotide and DNA fragments. This population can then be isolated or otherwise processed (e.g. size selected) (1618) using conventional techniques, e.g. a conventional spin column, or the like, to form population (1620) for analysis.

In one aspect, concatemers (1620) may be fixed to surface (1622) by any of a variety of techniques, including covalent attachment and non-covalent attachment. In one embodiment, surface (1622) may have attached capture oligonucleotides that form complexes, e.g. double stranded duplexes, with a segment of an adaptor oligonucleotide in the concatemers, such as an anchor binding site or other elements. In other embodiments, capture oligonucleotides may comprise oligonucleotide clamps, or like structures, that form triplexes with adaptor oligonucleotides, e.g. Gryaznov et al, U.S. Pat. No. 5,473,060. In another embodiment, surface (1622) may have reactive functionalities that react with complementary functionalities on the concatemers to form a covalent linkage, e.g. by way of the same techniques used to attach cDNAs to microarrays, e.g. Smirnov et al (2004), Genes, Chromosomes & Cancer, 40: 72-77; Beaucage (2001), Current Medicinal Chemistry, 8: 1213-1244, which are incorporated herein by reference. Long DNA molecules, e.g. several hundred nucleotides or larger, may also be efficiently attached to hydrophobic surfaces, such as a clean glass surface that has a low concentration of various reactive functionalities, such as —OH groups.

Figure 2D:
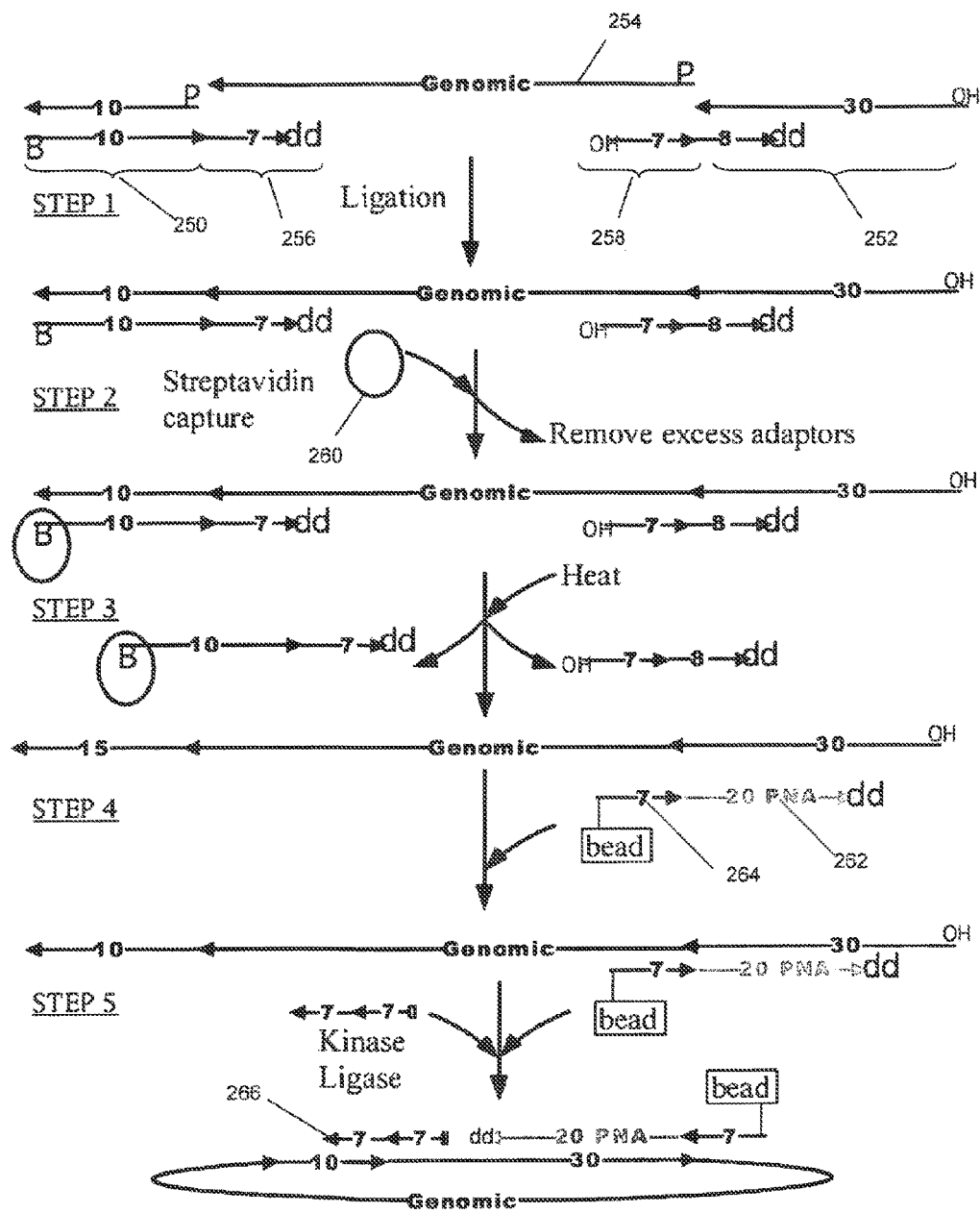

In FIG. 2D, another exemplary method for incorporating interspersed adaptors is illustrated. The method comprises the following steps: (1) Ligate two adaptor segments (250 and 252) to single stranded DNA fragments (254) using template oligonucleotides (the double stranded segment of 250 may be about 10 bases long, and the double stranded segment of 252 may be 8-10 bases long) containing degenerate bases (for example, segments 256 and 258 show the use of 7 degenerate bases, but 8 degenerate bases could also be used). Both ends of template oligonucleotides (250 and 256) are blocked from ligation with dideoxy termination on the 3' ends and either OH-group or biotin on the 5' ends. The adaptor/template hybrids are used at very high concentrations such as 1 µM and are in 1000-folds excess concentrations over genomic DNA. (2) DNA is collected on streptavidin support (260) via the biotin on the 5' end of the 3' adaptor (250). Excess free 5' adaptors are removed with the supernatant. (3) DNA is released from the streptavidin support by elevated temperature and the supernatant is collected. (4) DNA is recaptured to a solid support using a long capture oligonucleotide (262) with 3' end blocked by dideoxy termination. The oligonucleotide may be in the form of a peptide nucleic acid (PNA) to provide tight binding of the DNA to the solid support to facilitate removal of excess free adaptors in subsequent procedures. Capture oligonucleotide (262) can be extended by addition of 1-10 degenerate bases at the 5' end (264) for binding the genomic portion to increase stability. (5) The bridge template (266, which may be 14-18 bases long) is used to bring the two ends of the adaptors together to circularize the DNA molecule. It will be blocked on the 5' end with an amide group, but the 3'-OH group will be available for subsequent elongation by DNA polymerase in later steps. Kinase and ligase are provided in the reaction to phosphorylate the 5' end of the 5' adaptor and the ligation of the two ends of the DNA molecule.

Controlled closing of ssDNA circles and adaptor insertion. In this capture procedure, two adaptor segments are ligated to genomic ssDNA fragments using degenerated templates (FIG. 2D). The 3' end of the adaptor segment that ligates to the 5' end of the genomic DNA has a blocking complement. The template for the 3' adaptor segment has biotin. Adaptor/templates are in very high concentration such as 1 uM and have ~1000× high concentration from genomic DNA. DNA is collected on a streptavidin support and the solution is removed with the excess of adaptor components. The genomic DNA is released at an elevated temperature and the DNA solution is collected. The DNA is collected again on a second solid support with a long oligonucleotide (with blocked ends) complementary to the 5' end adaptor segment with removal of all other synthetic DNA. A bridging template is then added that serves also as a primer. Kinase and ligase (and polymerase) are added to close the circle and extend the primer to about 30 bases. Extension is controlled by time or by presence of ddNTPs. The enzymes are heat inactivated and the DNA is then cut with a type IIS restriction enzyme. The short double stranded portions are removed at elevated temperature with the circle attached to the solid support via a strong hybrid to the attached oligonucleotide. This stronger hybrid is maintained by incorporating LNA or PNA bases into the oligonucleotide. Two adaptor segments with templates for the second adaptor are then added (same design as above) no additional solid support attachment is required since the circle DNA will be continually associated with the solid support for further steps. Elevated temperatures are used to remove templates bound to the circular DNA. This step is repeated to insert a third adaptor. If no additional adaptors are planed then no polymerase is added and after a buffer exchange the DNA is released at elevated temperatures for the RCR reaction.

Figure 2E:
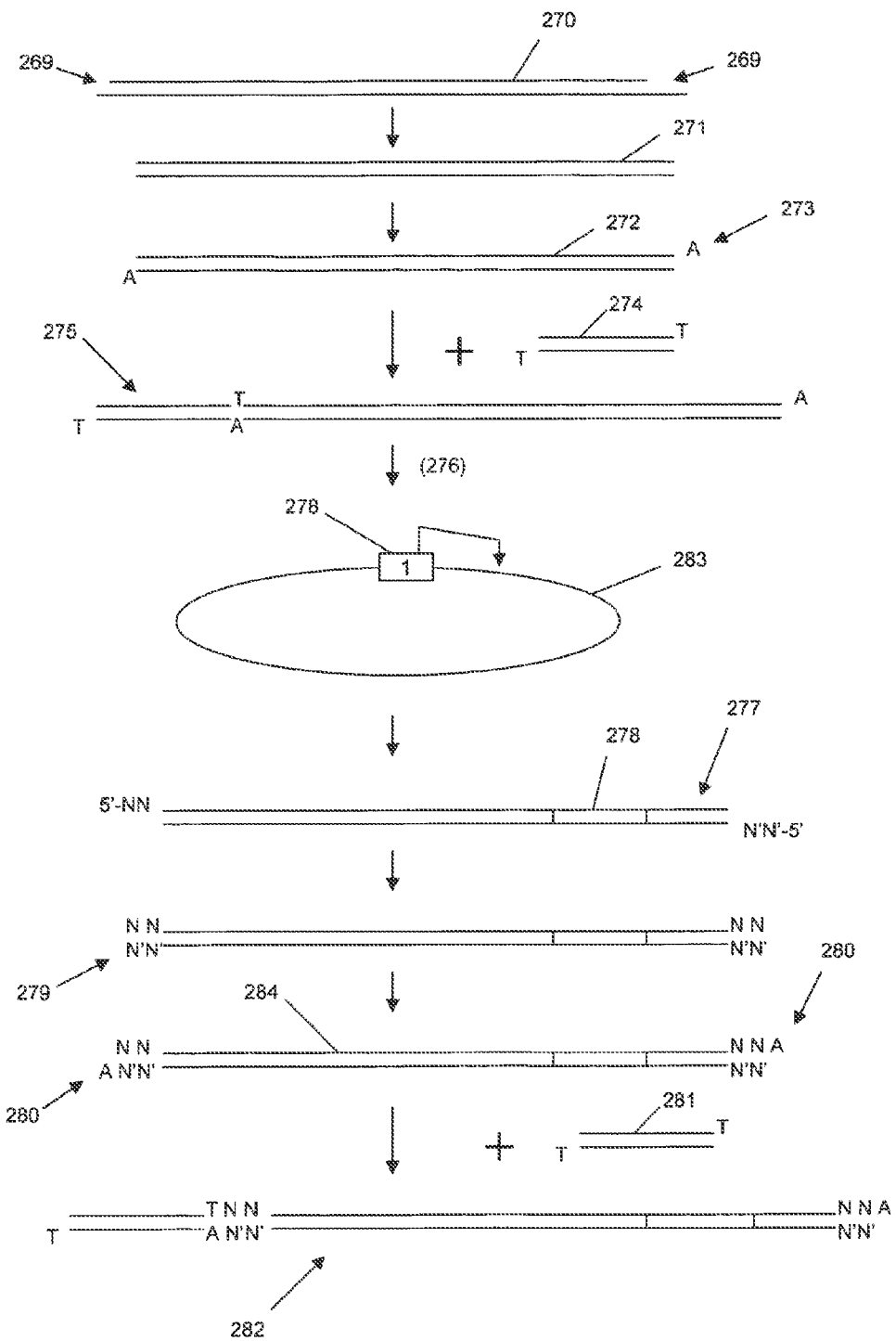

In FIG. 2E, another method for inserting interspersed adaptors is illustrated. This method has the advantage of generating segments of target polynucleotide having predetermined lengths adjacent to interspersed adaptors. The predetermined length are selected by selecting and positioning type IIs restriction endonucleases within the interspersed adaptors. In one aspect of this method, each different interspersed adaptor from the initial adaptor to the penultimate adaptor has a recognition site of a different type IIs restriction endonuclease. Double stranded DNA (dsDNA) is fragmented to produce target polynucleotides (270) having frayed ends (269), after which such ends are repaired using conventional techniques to form fragments (271) with blunt ends. To the 3' ends of blunt end fragments (271) a single nucleotide (273) is added, e.g. dA, using Taq polymerase, or like enzyme, to produce augmented fragments (272). Augmented fragments (272) are combined with interspersed adaptors (274) that have complementary nucleotide overhangs, e.g. dT, in the presence of a ligase so that multiple ligation products form, including product (275) that consists of a single interspersed adaptor and a single fragment. Conditions are adjusted to promote the circularization (276) of product (275) so that dsDNA circles (283) are formed. Other products (not shown, e.g. conjugates with interspersed adaptors at both ends or unligated fragments and adaptors) do not have the ability to form circles and are digested with a single stranded exonuclease after circularization of product (275). dsDNA circles (283) are treated with a type IIs restriction endonuclease recognizing a site in adaptor (278) to cleave dsDNA circles (283) to leave segment (277) of target polynucleotide (270) adjacent to adaptor (278). In this example, cleavage by the type IIs restriction endonuclease leaves 3' indented ends that are extended by a DNA polymerase to form blunt ends (279), after which fragment (284) is treated to add a single nucleotide to its 3' ends, as above. In this example, cleavage by the type IIs restriction endonuclease is shown to leave a two-base 3'-indented (or equivalently a 5' protruding) strand; however, the length of the protruding strand may be different than two, and may vary from cycle to cycle of adaptor incorporations. To fragment (284), a second interspersed adaptor (281) having complementary overhangs is ligated as described above. The process is repeated to incorporate additional interspersed adaptors. Optionally, in each cycle of interspersed adaptor incorporation, the desired product may be amplified to generate sufficient material for subsequent processing steps.

Figure 2F:
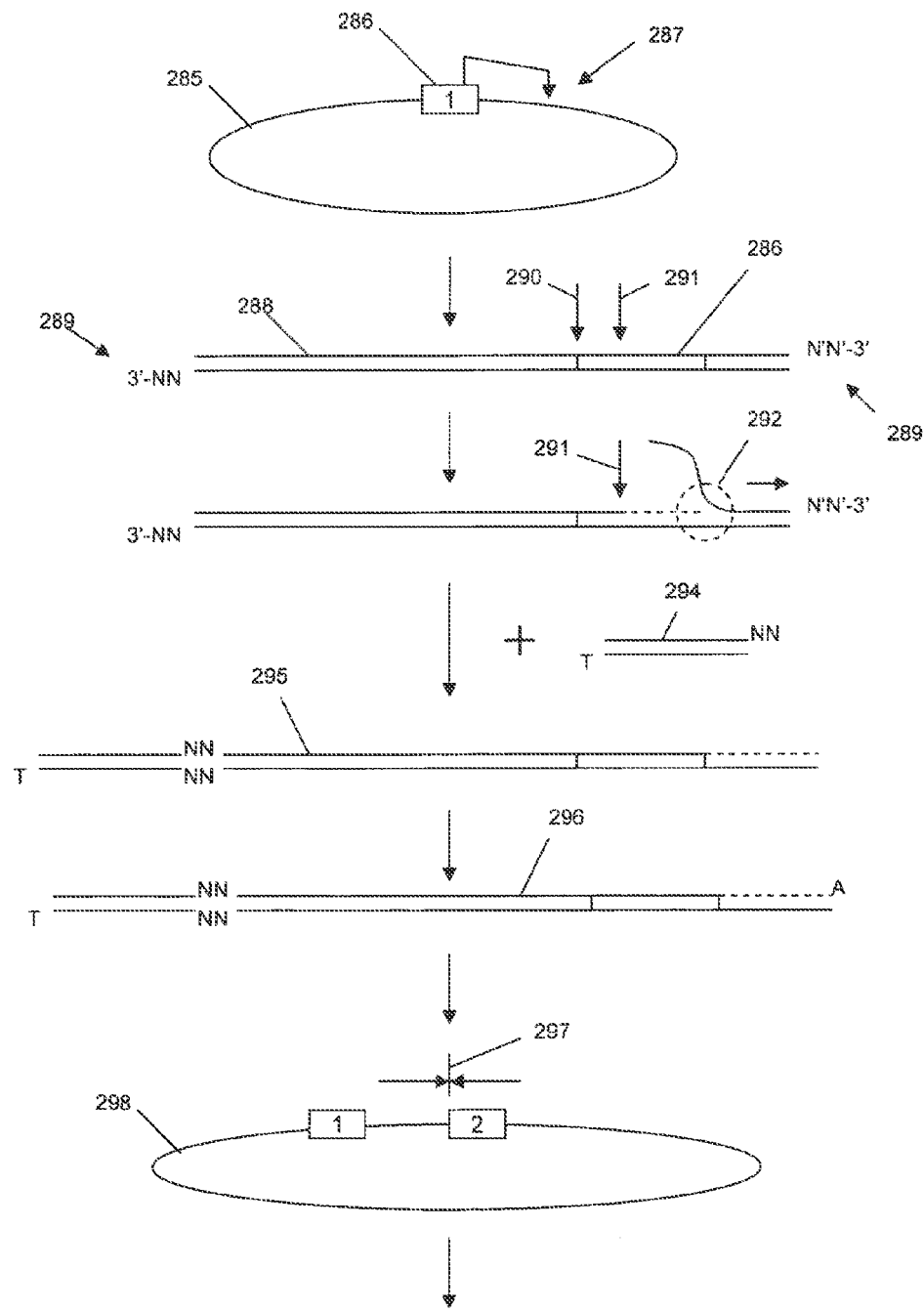

In FIG. 2F, another method is disclosed for incorporating interspersed adaptors at predetermined sites in a target polynucleotide. Fragments are generated as in FIG. 2E and dsDNA circles (285) are produced that have an initial interspersed adaptor (286) containing a type IIs recognition site, as described above, that cleaves dsDNA circle (285) at a predetermined site (287) to give fragment (288) having 3' overhangs (289), which as above may have lengths different than two. Interspersed adaptor of fragment (288) either contains a nick (290) at the boundary of the adaptor and the fragment or it contains the recognition site for a nicking endonuclease that permits the introduction of a nick (291) at the interior of the adaptor. In either case, fragment (288) is treated with a DNA polymerase (292) that can extend the upper strand from a nick (e.g. 291) to the end of the lower strand of fragment (288) to form a fragment having a 3' overhang at one end and a blunt end at the other. To this fragment is ligated an interspersed adaptor (294) that has degenerate nucleotide overhang at one end and a single 3' nucleotide (e.g. dT) overhang at the other end to form fragment (295), which is treated (e.g. with Taq polymerase) to add a 3' dA to its blunt end forming fragment (296). Fragment (296) is then circularized by ligation at site (297) to form dsDNA circle (298) and other ligation products are digested, as described above. Additional cycles of this process may be carried out to incorporate additional interspersed adaptors, and as above, optional steps of amplification may be added in each cycle, or as needed.

Figure 2G:
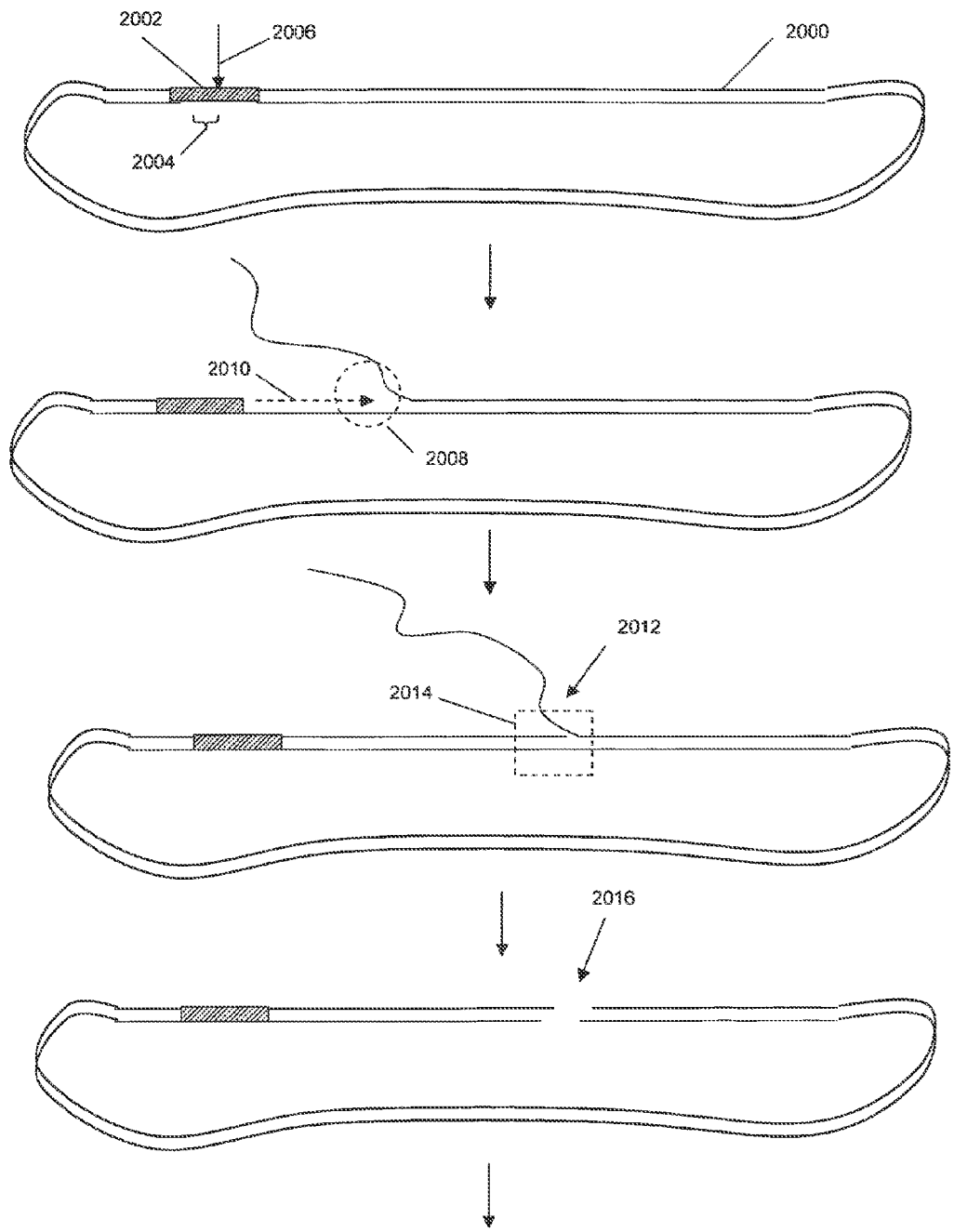
Figure 2H:
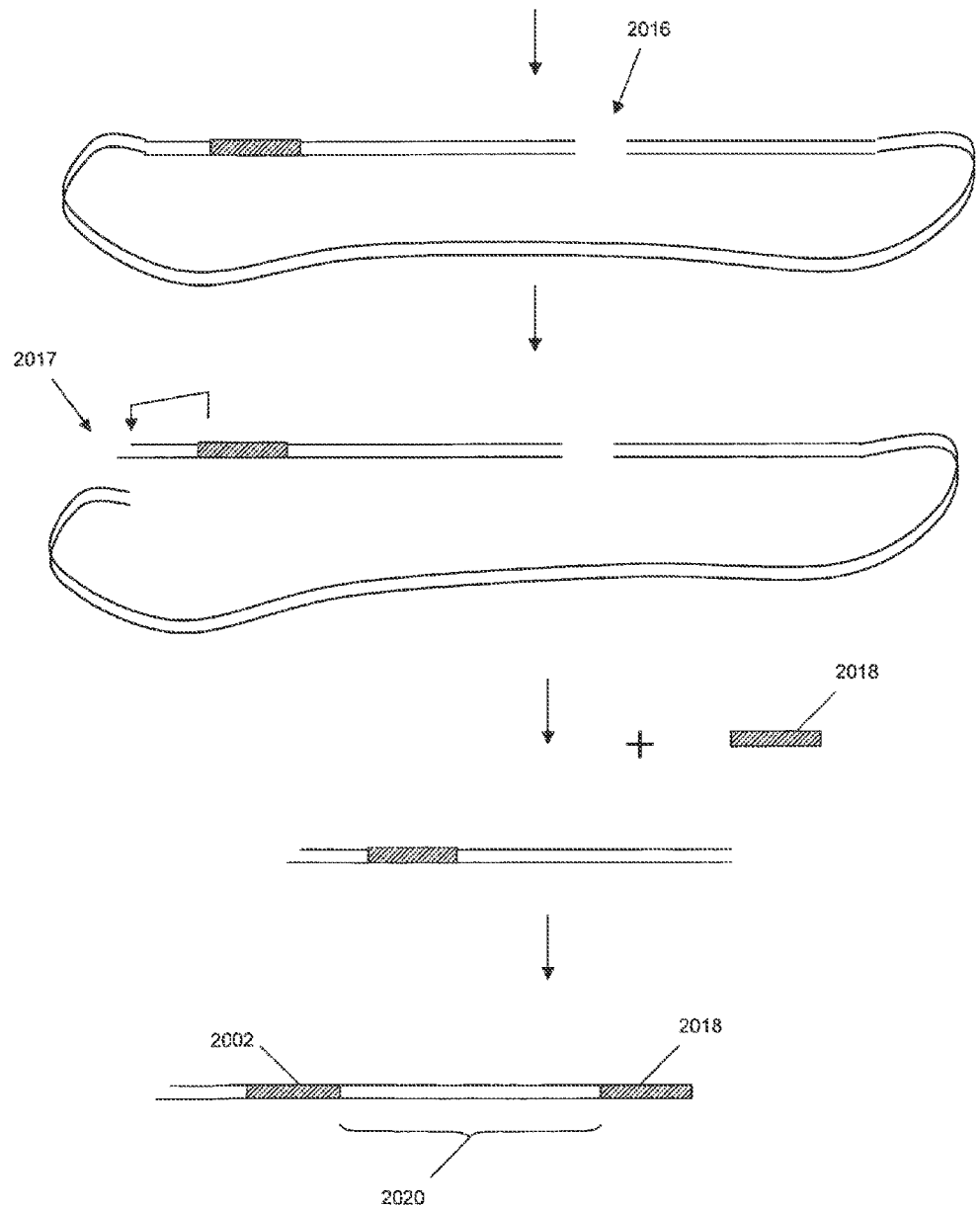

In FIG. 2G, another method of incorporating interspersed adaptors is illustrated that provides segments of variable lengths between interspersed adaptors. That is, in this example, interspersed adaptors are incorporated in a predetermined order, but at spacings that are not known precisely. This method allows incorporation of adapters at the distance longer than then provided by known or restriction enzymes. As above, dsDNA circles (2000) are prepared having an initial adaptor (2002) (that may or may not be an interspersed adaptor) containing a recognition site (2004) for a nicking enzyme. After creation of nick (2006), dsDNA circle (2000) is treated with a DNA polymerase (2008) that extends (2010) the free 3' strand and displaces or degrades the strand with the free 5' end at nick site (2006). The reaction is stopped after a predetermined interval, which is selected to be shorter than the expected time to synthesize more than a few hundred bases. Such extension may be halted by a variety of methods, including changing reaction conditions such as temperature, salt concentration, or the like, to disable the polymerase being used. This leaves dsDNA circle with a nick or other gap (2012), which is recognized and cleaved by a variety of enzymes having nuclease activities, such as DNA polymerases, FEN-1 endonucleases, 51 nuclease (2014), and the like, which may be used alone or in combination, e.g. Lieber, BioEssays, 19: 233-340 (1997). After cleavage at nick or gap (2012), the ends of the target polynucleotide may be repaired using techniques employed in shotgun sequencing, after which target polynucleotide (2000) may be cleaved (2017) to the left of adaptor (2002) using a type IIs restriction endonuclease that leaves a staggered, or sticky, end. To the blunt end, the next interspersed adaptor is attached, after which the resulting construct may be circularized using conventional techniques for further insertions of interspersed adaptors. Distance between successive interspersed adaptors, e.g. (2002) and (2018), are not know precisely and depend on the cleaving enzyme employed, the polymerase employed, the time interval allowed for synthesis, the method of stopping synthesis, reaction conditions, such as dNTP concentrations, and the like. In step (2010), nick translation can be used instead of strand displacement. In one aspect, in the polynucleotide break (2016) second adaptor may be ligated only to the sided connected to the first adaptor. This method can be combined with a second cut on the opposite side of the adaptor (2006) to create a mate-pair structure with various lengths of two segments such as (10-50)+(30-300) bases.

Figure 3A:
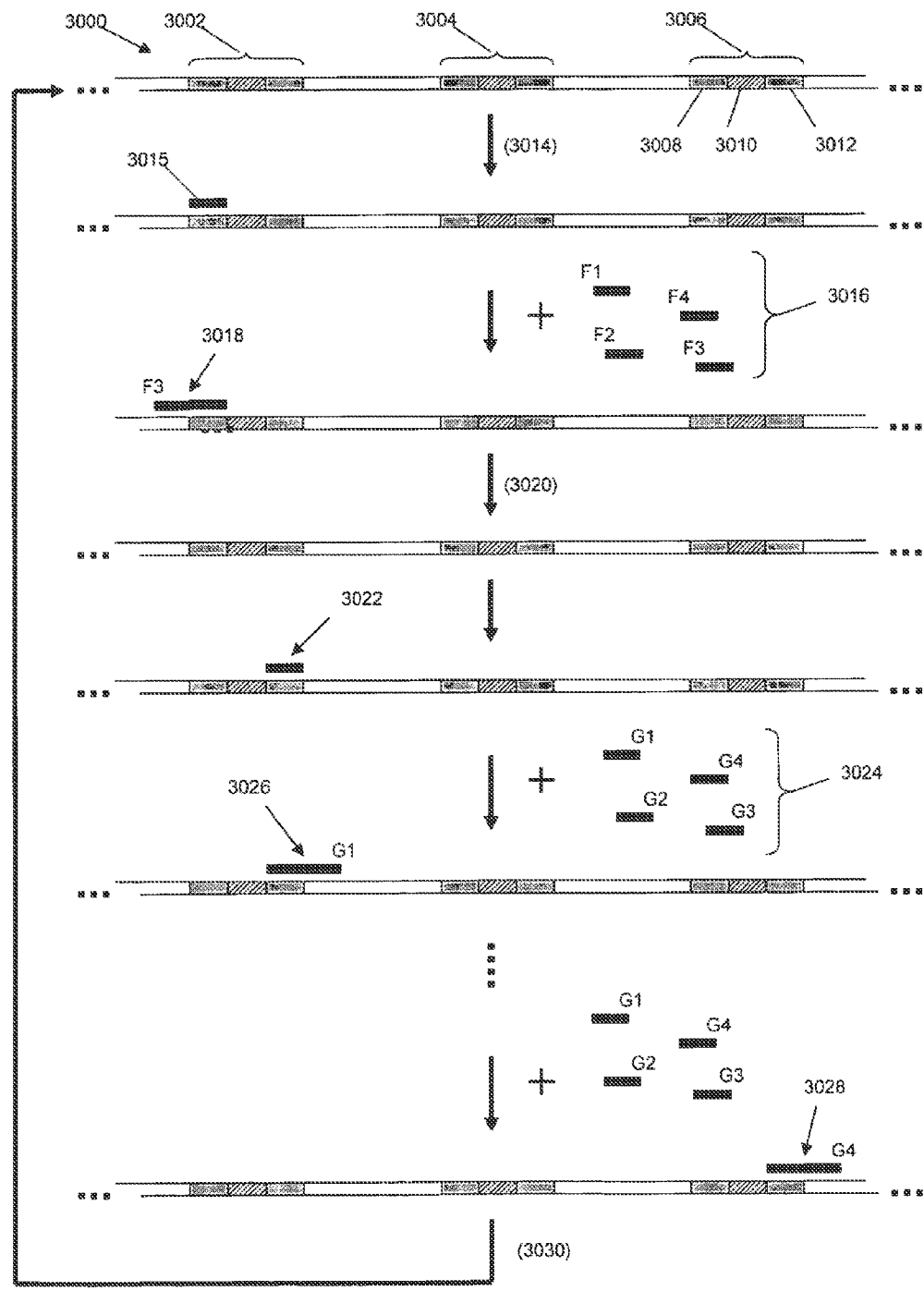
FIGS. 3A-3E illustrate a method of high-throughput sequencing that can be used to identify probe sequences containing interspersed adaptors.

In one aspect of the invention, a ligation-based sequencing method may be used that is illustrated in FIGS. 3A-3E. Many different variations of this sequencing approach may be selected by one of ordinary skill in the art depending on factors, such as, the volume of sequencing desired, the type of labels employed, the type of target polynucleotide amplicons employed and how they are attached to a surface, the desired speed of sequencing operations, signal detection approaches, and the like. The variations shown in FIGS. 3A-3E are only exemplary and generally are designed to identify bases adjacent to interspersed adaptors. In one aspect, such sequence information is used as a signature sequence of the probe sequence of a concatemer; that is, enough sequence information is obtained in a sequencing operation to unambiguously identify which probe sequence is present from the set of all probe sequences being used in a random array. Clearly, the amount of sequence information necessary to infer the identity of the probe sequences depends on the number of probe sequences being used. The greater number of different probe sequences, the more sequence information will be necessary for unambiguous identification. In some embodiments, this may include sequencing the entire probe sequence. In other embodiment, this may include sequencing only a small number of bases of the probe sequences. A predetermined size polynucleotide forming concatemer will be continuous without adapters to serve as long probe (about 20-200 bases). The sequence of the probe will be inferred from the reference sequence adjacent to the sequenced part. In one aspect sequenced parts may be obtained from both ends of the probe to provide full mapping of the unsequenced part of the probe. Single stranded target polynucleotide (3000) is provided that contains a plurality of interspersed adaptors. In FIG. 3A, three interspersed adaptors (3002, 3004, and 3006) are shown, which may be part of an amplicon, such as a concatemer, comprising multiple copies of target polynucleotide (3000). Each interspersed adaptor has a region (e.g. 3008 and 3012) at each end that has a unique sequence (in this example six such unique sequences among three interspersed adaptors in all) designed as a binding site for a corresponding anchor probe, which is an oligonucleotide (which may or may not carry a label) to which a sequencing probe is ligated. Such end regions may have lengths in the range of from 6 to 14 nucleotides, and more usually, from 8 to 12 nucleotides. Interspersed adaptors optionally have central region (3010), which may contain additional elements such as recognition sites for various enzymes (when in double stranded form) or binding sites for capture oligonucleotides for immobilizing the target polynucleotide amplicons on a surface, and so on. In one aspect, a sequencing operation with interspersed adaptors (3002-3006) comprises six successive routines of hybridizing anchor probes to each of the different unique anchor probe binding sites. Each such routine comprises a cycle of hybridizing the anchor probe to its end site of its interspersed adaptor, combining with sequencing probes under conditions that permit hybridization of only perfectly matched probes, ligating perfectly matched sequencing probes to juxtaposed anchor probes, detecting ligated sequencing probes, identifying one or more bases adjacent to the anchor probe by the signal generated by the sequencing probe, and removing the sequencing probe and the anchor probe from the target polynucleotide amplicon. Depending on the number of bases detected by each sequencing probe, either the six successive routines are repeated from 1 to 4 times (or more usually from 2 to 3 times), so that nucleotides at different distances from the interspersed adaptor may be identified, or the six successive routines are carried out once, but each cycle of anchor probe hybridization, sequencing probe hybridization, ligating, etc., is repeated from 1 to 4, or from 2 to 3 times. The former is illustrated in FIG. 3A, so that after anchor probe (3015) hybridizes to its binding site in interspersed adaptor (3002), labeled sequencing probes (3016) are added to the reaction mixture under conditions that permit ligation to anchor probe (3015) if a perfectly matched duplex is formed. Sequencing probes may have a variety of different structures. Typically, they contain degenerate sequences and are either directly or indirectly labeled. In the example of FIG. 3A, sequencing probes are directly labeled with, e.g. fluorescent dyes F1, F2, F3, and F4, which generate signals that are mutually distinguishable, and fluorescent dyes G1, G2, G3, and G4, which also generate signals that are mutually distinguishable. In this example, since dyes of each set, i.e. F and G, are detected in different cycles, they may be the same dyes. When 8-mer sequencing probes are employed, a set of F-labeled probes for identifying a base immediately adjacent to an interspersed adaptor may have the following structure: 3'-F1-NNNNNNNAp, 3'-F2-NNNNNNNCp, 3'-F3-NNNNNNNGp, 3'-F4-NNNNNNNT. Here it is assumed that sequence (3000) is in a 5'→3' orientation from left to right; thus, the F-labeled probes must carry a phosphate group on their 5' ends, as long as conventional ligase-mediated ligation reactions are used. Likewise, a corresponding set of G-labeled probes may have the following structure: 3'-ANNNNNNN-G1,3'-CNNNNNNN-G2,3'-GNNNNNNN-G3,3'-TNNNNNNN-G4, and for ligation of these probes, their associated anchor probe must have a 5'-phosphate group. F-labeled probes in successive cycles may have the following structures: 3'-F1-NNNNNNANp, 3'-F2-NNNNNNCNp, 3'-F3-NNNNNNGNp, 3'-F4-NNNNNNTN, and 3'-F1-NNNNNANNp, 3'-F2-NNNNNCNNp, 3'-F3-NNNNNGNNp, 3'-F4-NNNNNTNN, and so on. Returning to FIG. 3A, after ligated probe (3018) is identified, it is removed from the target polynucleotide amplicon (3020), and the next anchor probe (3022) is hybridized to its respective binding site. G-labeled sequencing probes are hybridized to the target polynucleotide so that those forming perfectly match duplexes juxtaposed to the anchor probe are ligated and identified. This process continues for each anchor probe binding site until the last ligated probe (3028) is identified. The whole sequence of cycles is then repeated (3030) using F-labeled sequencing probes and G-labeled sequencing probes that are design to identify a different base adjacent to its respective anchor probe.

Figure 3B:
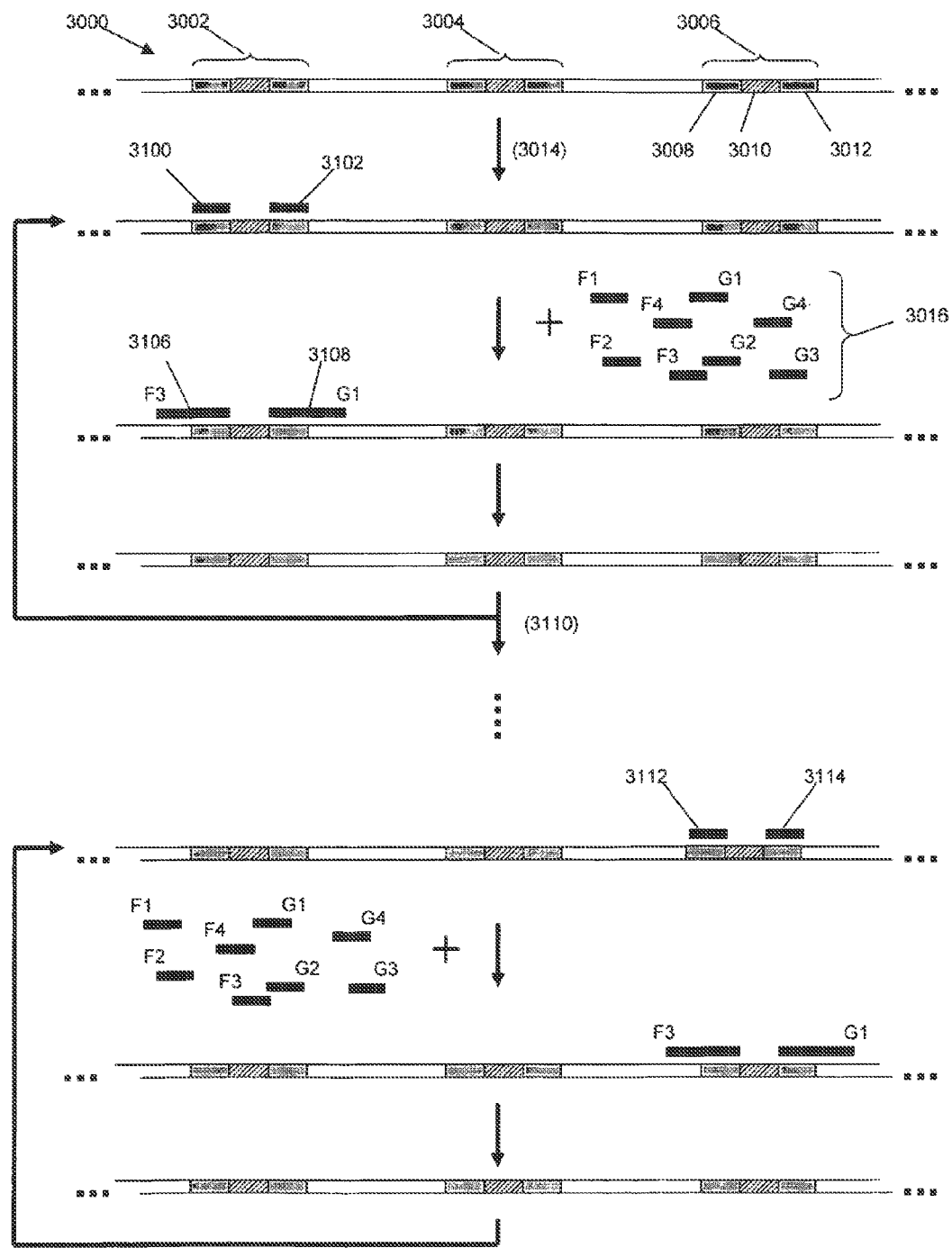

FIG. 3B illustrates a variant of the method of FIG. 3A in which anchor probes are hybridized to their respective binding sites two-at-a-time. Any pair of anchor probes may be employed as long as one member of the pair binds to a 3' binding site of an interspersed adaptor and the other member of the pair binds to a 5' binding site of an interspersed adaptor. For directly labeled sequencing probes, as shown, this embodiment requires the use of eight distinguishable labels; that is, each of the labels F1-F4 and G1-G4 must be distinguishable from one another. In FIG. 3B, anchor probes (3100 and 3102) are hybridized to their respective binding sites in interspersed adaptor (3002), after which a set of sequencing probes (3104) is added under stringent hybridization conditions. Probes that form perfectly matched duplexes are ligated, unligated probes are washed away, after which the ligated probes are identified. Cycles of such hybridization, ligation and washing are repeated (3110) with sets of sequencing probes designed to identify bases at different sites adjacent to interspersed adaptor (3002). The process is then repeated for each interspersed adaptor.

Figure 3C:
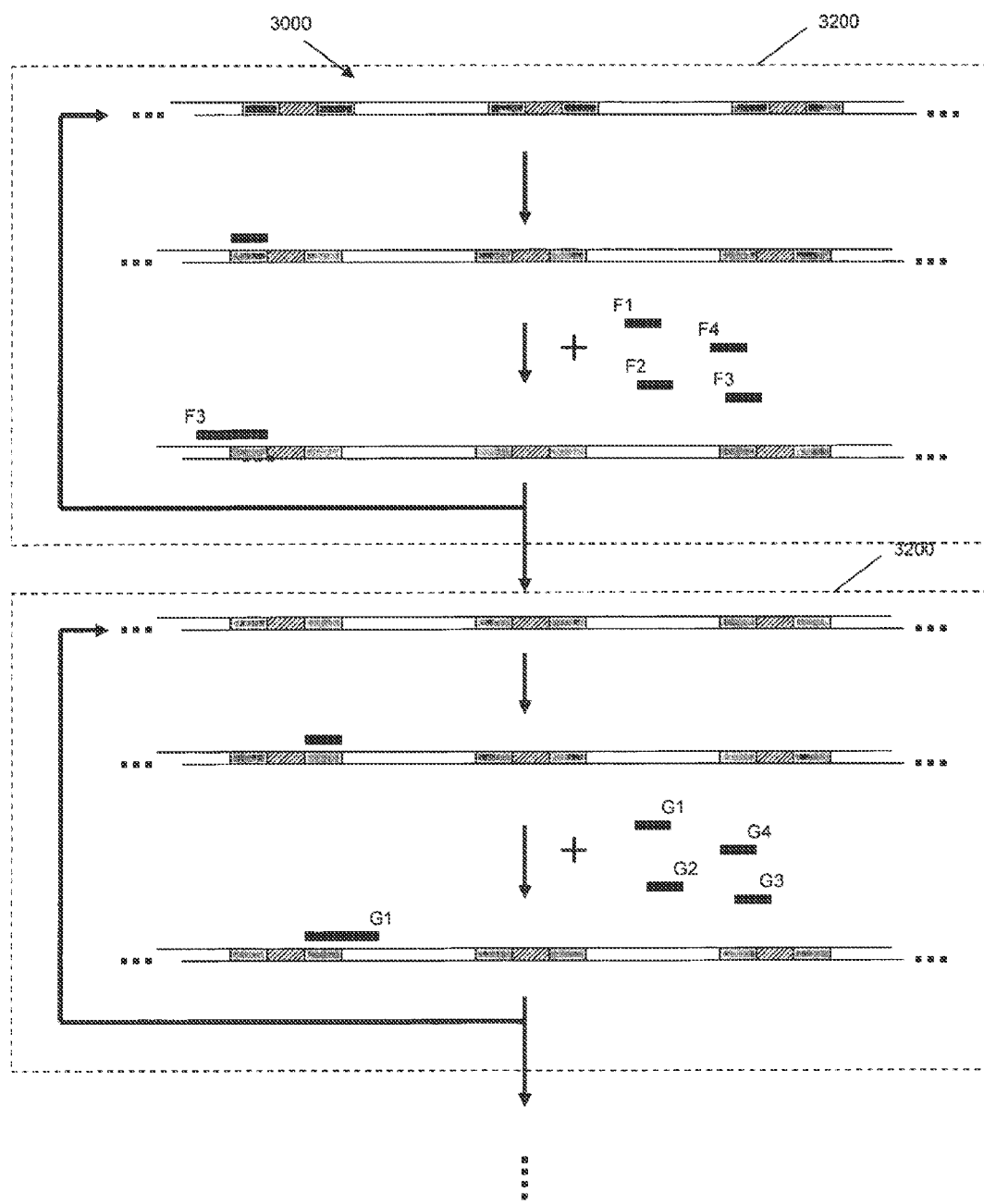

FIG. 3C is another variant of the embodiment of FIG. 3A, in which sequencing probes for identify bases at every site adjacent to an anchor probe are carried out to completion before an anchor probe for any other interspersed adaptor is used. Briefly, the steps within each dashed box (3200) are carried out for each anchor probe binding site, one at a time; thus, each dashed box corresponds to a different anchor probe binding site. Within each box, successive cycles are carried out comprising the steps of hybridizing an anchor probe, ligating sequencing probes, identifying ligated sequencing probes.

Figure 3D:
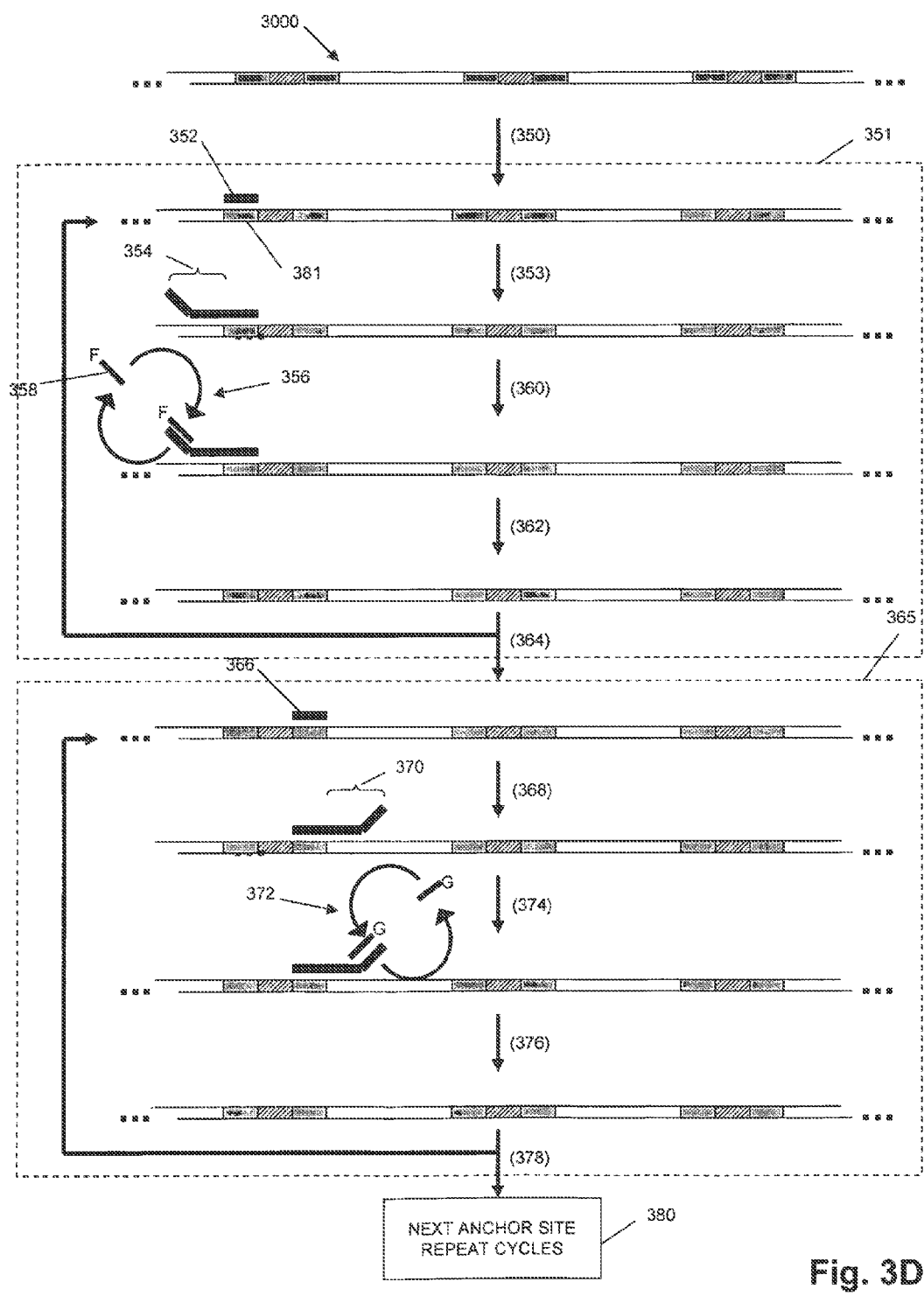
Figure 3E:
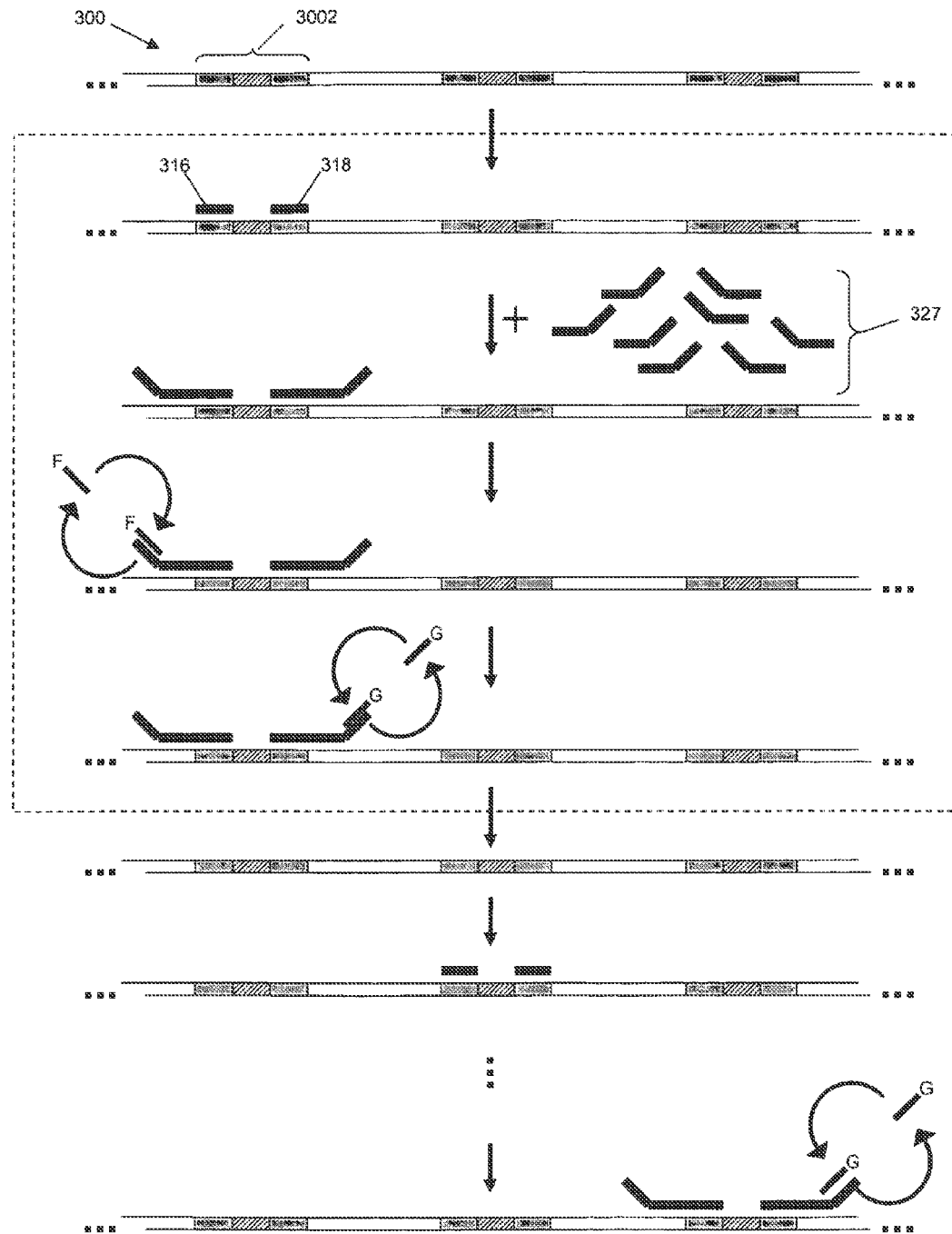

FIG. 3D illustrates an embodiment that employs encoded label, similar to those used with the encoded adaptors disclosed by Albrecht et al, U.S. Pat. No. 6,013,445, which is incorporated herein by reference. The process is similar to that described in FIG. 3C, except that instead of directly labeled sequencing probes, such probes are indirectly labeled with oligonucleotide tags. By using such tags, the number of ligation steps can be reduced, since each sequencing probe mixture may contain sequences to identify many more than four bases. For example, non-cross-hybridizing oligonucleotide tags may be selected that correspond to each of sixteen pairs of bases, so that after ligation, ligated sequencing probes may be interrogated with sets of labeled anti-tags until each two-base sequence is identified. Thus, the sequence of a target polynucleotide adjacent to an anchor probe may be identified two-at-a-time, or three-at-a-time, or more, using encoded sequencing probes. Going to FIG. 3D, anchor probe (352) is hybridized to anchor binding site (381), after which encoded sequencing probes are added under conditions that permit only perfectly complementary sequencing probes (354) to be ligated to anchor probes (352). After such ligation and washing away of un-ligated sequencing probes, labeled anti-tags (358) are successively hybridized to the oligonucleotide tags of the sequencing probes under stringent conditions so that only labeled anti-tags forming perfectly matched duplexes are detected. A variety of different labeling schemes may be used with the anti-tags. A single label may be used for all anti-tags and each anti-tag may be separately hybridized to the encoded sequencing tags. Alternatively, sets of anti-tags may be employed to reduce the number of hybridizations and washings that must be carried out. For example, where each sequencing probe identifies two bases, two sets of four anti-tags each may be applied, wherein each tag in a given set carries a distinct label according to the identity of one of the two bases identified by the sequencing probe. Likewise, if a sequencing probe identifies three bases, then three sets of four anti-tags each may be used for decoding. Such cycles of decoding may be carried out for each interspersed adaptor, after which additional cycles may be carried out using sequencing probes that identify bases at different sites. FIG. 3E illustrates an embodiment similar to that described in FIG. 3B, except that here encoded sequencing probes are employed. Thus, two anchor probes are hybridized to a target polynucleotide at a time and the corresponding sequencing probes are identified by decoding with labeled anti-tags. As shown, anchor probes (316 and 318) are hybridized to their respective binding sites on interspersed adaptor (3002), after which two sets of encoded sequencing probes (327) are added under conditions that permit only such probes forming perfectly matched duplexes to be ligated. After removal of unligated probes, the oligonucleotide tags of the ligated probes are decoded with labeled anti-tags. As above, a variety of schemes are available for decoding the ligated sequencing probes.

In another aspect, a sequencing method for use with the invention for determining sequences in a plurality of DNA or RNA fragments comprises the following steps: (a) generating a plurality of polynucleotide molecules each comprising a concatemer of a DNA or RNA fragment; (b) forming a random array of polynucleotide molecules fixed to a surface at a density such that at least a majority of the target concatemers are optically resolvable; and (c) identifying a sequence of at least a portion of each DNA or RNA fragment in resolvable polynucleotides using at least one chemical reaction of an optically detectable reactant. In one embodiment, such optically detectable reactant is an oligonucleotide. In another embodiment, such optically detectable reactant is a nucleoside triphosphate, e.g. a fluorescently labeled nucleoside triphosphate that may be used to extend an oligonucleotide hybridized to a concatemer. In another embodiment, such optically detectable reagent is an oligonucleotide formed by ligating first and second oligonucleotides that form adjacent duplexes on a concatemer. In another embodiment, such chemical reaction is synthesis of DNA or RNA, e.g. by extending a primer hybridized to a concatemer.

Labels and Signal Generation by Probes and/or Target Sequences Hybridized to Polynucleotides on Random Arrays Nucleic acid fragments used as target sequences, or sequencing probes, used in the invention can be labeled in a variety of ways, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka, Ann. Clin. Biochem., 39: 114-129 (2002); Schaferling et al, Anal. Bioanal. Chem., (Apr. 12, 2006); Matthews et al, *Anal. Biochem.*, Vol 169, pgs. 1-25 (1988); Haugland, Handbook of Fluorescent Probes and Research Chemicals, Tenth Edition (Invitrogen/Molecular Probes, Inc., Eugene, 2006); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227-259 (1991); Hermanson, Bioconjugate Techniques (Academic Press, New York, 1996); and the like. Many more particular methodologies applicable to the invention are disclosed in the following sample of references: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115-6128 (1986)(enzyme-oligonucleotide conjugates); Ju et al, Nature Medicine, 2: 246-249 (1996); Bawendi et al, U.S. Pat. No. 6,326,144 (derivatized fluorescent nanocrystals); Bruchez et al, U.S. Pat. No. 6,274,323 (derivatized fluorescent nanocrystals); and the like.

In one aspect, one or more fluorescent dyes are used as labels for target sequences, e.g. as disclosed by Menchen et al, U.S. Pat. No. 5,188,934 (4,7-dichlorofluorescein dyes); Begot et al, U.S. Pat. No. 5,366,860 (spectrally resolvable rhodamine dyes); Lee et al, U.S. Pat. No. 5,847,162 (4,7-dichlororhodamine dyes); Khanna et al, U.S. Pat. No. 4,318,846 (ether-substituted fluorescein dyes); Lee et al, U.S. Pat. No. 5,800,996 (energy transfer dyes); Lee et al, U.S. Pat. No. 5,066,580 (xanthene dyes): Mathies et al, U.S. Pat. No. 5,688,648 (energy transfer dyes); and the like. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, energy transfer, and the like. Biotin, or a derivative thereof, may also be used as a label on target sequences, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into a detection oligonucleotide and subsequently coupled to an N-hydroxy succinimide (NHS) derivitized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as an Fab. Other suitable labels for target sequences may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr), or any other suitable label. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM. As described in schemes below, target sequences may also be indirectly labeled, especially with a hapten that is then bound by a capture agent, e.g. as disclosed in Holtke et al, U.S. Pat. Nos. 5,344,757; 5,702,888; and 5,354,657; Huber et al, U.S. Pat. No. 5,198,537; Miyoshi, U.S. Pat. No. 4,849,336; Misiura and Gait, PCT publication WO 91/17160; and the like. Many different hapten-capture agent pairs are available for use with the invention. Exemplary, haptens include, biotin, des-biotin and other derivatives, dinitrophenol, dansyl, fluorescein, CY5, and other dyes, digoxigenin, and the like. For biotin, a capture agent may be avidin, streptavidin, or antibodies. Antibodies may be used as capture agents for the other haptens (many dye-antibody pairs being commercially available, e.g. Molecular Probes).

Detection Instrumentation

As mentioned above, signals from single molecules on random arrays are generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, $2^{nd}$ Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; Lehr et al (cited above); and Drmanac, International patent publication WO 2004/076683. In one aspect, instruments for use with arrays of the invention comprise three basic components: (i) a fluidics system for storing and transferring detection and processing reagents, e.g. probes, wash solutions, and the like, to an array; (ii) a reaction chamber, or flow cell, holding or comprising an array and having flow-through and temperature control capability; and (iii) an illumination and detection system. In one embodiment, a flow cell has a temperature control subsystem with ability to maintain temperature in the range from about 5-95° C., or more specifically 10-85° C., and can change temperature with a rate of about 0.5-2° C. per second.

In one aspect, a flow cell for 1" square 170 micrometer thick cover slips can be used that has been derivatized to bind macromolecular structures of the invention. The cell encloses the "array" by sandwiching the glass and a gasket between two planes. One plane has an opening of sufficient size to permit imaging, and an indexing pocket for the cover slip. The other plane has an indexing pocket for the gasket, fluid ports, and a temperature control system. One fluid port is connected to a syringe pump which "pulls" or "pushes" fluid from the flow cell the other port is connected to a funnel like mixing chamber. The chamber, in turn is equipped with a liquid level sensor. The solutions are dispensed into the funnel, mixed if needed, then drawn into the flow cell. When the level sensor reads air in the funnels connection to the flow cell the pump is reversed a known amount to back the fluid up to the funnel. This prevents air from entering the flow cell. The cover slip surface may be sectioned off and divided into strips to accommodate fluid flow/capillary effects caused by sandwiching. Such substrate may be housed in an "open air"/"open face" chamber to promote even flow of the buffers over the substrate by eliminating capillary flow effects. Imaging may be accomplished with a 100× objective using TIRF or epi illumination and a 1.3 mega pixel Hamamatsu orca-er-ag on a Zeiss axiovert 200, or like system. This configuration images RCR concatemers bound randomly to a substrate (non-ordered array). Imaging speed may be improved by decreasing the objective magnification power, using grid patterned arrays and increasing the number of pixels of data collected in each image. For example, up to four or more cameras may be used, preferably in the 10-16 megapixel range. Multiple band pass filters and dichroic mirrors may also be used to collect pixel data across up to four or more emission spectra. To compensate for the lower light collecting power of the decreased magnification objective, the power of the excitation light source can be increased. Throughput can be increased by using one or more flow chambers with each camera, so that the imaging system is not idle while the samples are being hybridized/reacted. Because the probing of arrays can be non-sequential, more than one imaging system can be used to collect data from a set of arrays, further decreasing assay time.

During the imaging process, the substrate must remain in focus. Some key factors in maintaining focus are the flatness of the substrate, orthogonality of the substrate to the focus plane, and mechanical forces on the substrate that may deform it. Substrate flatness can be well controlled, glass plates which have better than ¼ wave flatness are readily obtained. Uneven mechanical forces on the substrate can be minimized through proper design of the hybridization chamber. Orthogonality to the focus plane can be achieved by a well adjusted, high precision stage. Auto focus routines generally take additional time to run, so it is desirable to run them only if necessary. After each image is acquired, it will be analyzed using a fast algorithm to determine if the image is in focus. If the image is out of focus, the auto focus routine will run. It will then store the objectives Z position information to be used upon return to that section of that array during the next imaging cycle. By mapping the objectives Z position at various locations on the substrate, we will reduce the time required for substrate image acquisition.

A suitable illumination and detection system for fluorescence-based signal is a Zeiss Axiovert 200 equipped with a TIRF slider coupled to a 80 milliwatt 532 nm solid state laser. The slider illuminates the substrate through the objective at the correct TIRF illumination angle. TIRF can also be accomplished without the use of the objective by illuminating the substrate though a prism optically coupled to the substrate. Planar wave guides can also be used to implement TIRF on the substrate Epi illumination can also be employed. The light source can be rastered, spread beam, coherent, incoherent, and originate from a single or multi-spectrum source.

One embodiment for the imaging system contains a 20× lens with a 1.25 mm field of view, with detection being accomplished with a 10 megapixel camera. Such a system images approx 1.5 million concatemers attached to the patterned array at 1 micron pitch. Under this configuration there are approximately 6.4 pixels per concatemer. The number of pixels per concatemer can be adjusted by increasing or decreasing the field of view of the objective. For example a 1 mm field of view would yield a value of 10 pixels per concatemer and a 2 mm field of view would yield a value of 2.5 pixels per concatemer. The field of view may be adjusted relative to the magnification and NA of the objective to yield the lowest pixel count per concatemer that is still capable of being resolved by the optics, and image analysis software.

Both TIRF and EPI illumination allow for almost any light source to be used. One illumination schema is to share a common set of monochromatic illumination sources (about 4 lasers for 6-8 colors) amongst imagers. Each imager collects data at a different wavelength at any given time and the light sources would be switched to the imagers via an optical switching system. In such an embodiment, the illumination source preferably produces at least 6, but more preferably 8 different wavelengths. Such sources include gas lasers, multiple diode pumped solid state lasers combined through a fiber coupler, filtered Xenon Arc lamps, tunable lasers, or the more novel Spectralum Light Engine, soon to be offered by Tidal Photonics. The Spectralum Light Engine uses prism to spectrally separate light. The spectrum is projected onto a Texas Instruments Digital Light Processor, which can selectively reflect any portion of the spectrum into a fiber or optical connector. This system is capable of monitoring and calibrating the power output across individual wavelengths to keep them constant so as to automatically compensate for intensity differences as bulbs age or between bulb changes.

Successfully scoring 6 billion concatemers through ~350 (~60 per color) images per region over 24 hours may require a combination of parallel image acquisition, increased image acquisition speed, and increased field of view for each imager. Additionally, the imager may support between six to eight colors. Commercially available microscopes commonly image a ~1 mm field of view at 20× magnification with an NA of 0.8. At the proposed concatemer pitch of 0.5 micron, this translates into roughly 4 million concatemers per image. This yields approximately 1,500 images for 6 billion spots per hybridization cycle, or 0.5 million images for 350 imaging cycles. In a large scale sequencing operation, each imager preferably acquires ~200,000 images per day, based on a 300 millisecond exposure time to a 16 mega pixel CCD. Thus, a preferred instrument design is 4 imager modules each serving 4 flow cells (16 flow cells total). The above described imaging schema assumes that each imager has a CCD detector with 10 million pixels and be used with an exposure time of roughly 300 milliseconds. This should be an acceptable method for collecting data for 6 fluorophor labels. One possible drawback to this imaging technique is that certain fluorophors may be unintentionally photo bleached by the light source while other fluorophores are being imaged. Keeping the illumination power low and exposure times to a minimum would greatly reduce photo bleaching. By using intensified CCDs (ICCDs) data could be collected of roughly the same quality with illumination intensities and exposure times that are orders of magnitude lower than standard CCDs. ICCDs are generally available in the 1-1.4 megapixel range. Because they require much shorter exposure times, a one megapixel ICCD can acquire ten or more images in the time a standard CCD acquires a single image. Used in conjunction with fast filter wheels, and a high speed flow cell stage, a one mega pixel ICCD should be able to collect the same amount of data as a 10 megapixel standard CCD.

Optics capable of imaging larger fields of view with high numerical apertures can be manufactured as custom lens assemblies. Indications are that 20× optics capable of imaging a 3 mm field of view with a NA>0.9 can be fabricated. Two such imaging systems, in combination with high pixel count CCD's or CCD mosaic arrays should be able to image the complete eight flow cell assay in roughly 14 hours. As described, further gains can be realized by using 16 flow cells. Doubling the number of flow cells would reduce imaging time to 9 hours by reducing the number of images per each field of view.

The reaction efficiency on the concatemer and other random DNA arrays may depend on the efficient use of probes, anchors or primers and enzymes. This may be achieved by mixing liquids (such as pooling liquid back and forth in the flow through chamber), applying agitations or using horizontal or vertical electric fields to bring DNA from different parts of the reaction volume in the proximity of the surface. One approach for efficient low cost assay reaction is to apply reaction mixes in a thin layer such as droplets or layers of about one to a few microns, but preferably less than 10 microns, in size/thickness. In a 1×1×1 micron volume designated for a 1×1 micron spot area, in 1 pmol/1 ul (1 uM concentration) there would be about 1000 molecules of probe in close proximity to 1-1000 copies of DNA. Using up to 100-300 molecules of probes would not significantly reduce the probe concentration and it would provide enough reacted probes to get significant signal. This approach may be used in an open reaction chamber that may stay open or closed for removal and washing of the probes and enzyme.

As mentioned above, higher throughput can be achieved by using multiple cameras and multiple flow cells. A single robotic liquid handling gantry may service, for example, 16 flow cells. In addition, all components of the system may share a common temperature control system, and set of reagents. For combinatorial SBH sequencing operations, the robot may prepare probe pools and ligation buffers to be dispensed into the flow cell funnels. Dedicated syringe pumps may dispense wash and hybridization buffers directly into the funnel ports for each flow cell. Each imager may service a group of 2-4 flow cells. Each group of flow cells may be positioned on an XY motion platform, similar to the automated plate stages commonly found on research microscopes. System control and coordination between all system components may be performed via software running on a master computer. The control software may run assay cycles asynchronously, allowing each imager to run continuously throughout the assay. Flow cells are connected to a temperature control system with one heater and one chiller allowing for heating or cooling on demand of each flow cell or 2-4 blocks of cells independently. Each flow cell temperature may be monitored, and if a flow cell temperature drops below a set threshold, a valve may open to a hot water recirculation. Likewise, if a flow cell temperature is above the set threshold a valve may open to a cold water recirculation. If a flow cell is within a set temperature range neither valve may open. The hot and cold recirculation water runs through the aluminum flow cell body, but remains separate and isolated from the assay buffers and reagents.

Kits of the Invention

In the commercialization of the methods described herein, certain kits for construction of random arrays and for using the same for various applications are particularly useful. Kits for applications of random arrays include, but are not limited to, kits for analyzing gene expression of a particular organism, kits for large-scale identification of differences between reference DNA sequences and test DNA sequences, kits for profiling exons, kits for assessing genome-wide genome sequence copy number variance, and the like. A kit typically comprises at least one support having a surface and one or more reagents necessary or useful for constructing a random array of the invention or for carrying out an application therewith. Such reagents include, without limitation, nucleic acid primers, probes, adaptors, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In one aspect, the invention provides a kit for making a random array of concatemers of DNA fragments from a source nucleic acid comprising the following components: (i) a support having a surface; and (ii) at least one adaptor oligonucleotide for ligating to each DNA fragment and forming a DNA circle therewith, each DNA circle capable of being replicated by a rolling circle replication reaction to form a concatemer that is capable of being randomly disposed on the surface. In such kits, the surface may be a planar surface having an array of discrete spaced apart regions, wherein each discrete spaced apart region has a size equivalent to that of said concatemers. The discrete spaced apart regions may form a regular array with a nearest neighbor distance in the range of from 0.1 to 20 μm. The concatemers on the discrete spaced apart regions may have a nearest neighbor distance such that they are optically resolvable. The discrete spaced apart regions may have capture oligonucleotides attached and the adaptor oligonucleotides may each have a region complementary to the capture oligonucleotides such that the concatemers are capable of being attached to the discrete spaced apart regions by formation of complexes between the capture oligonucleotides and the complementary regions of the adaptor oligonucleotides. In some embodiments, the concatemers are randomly distributed on said discrete spaced apart regions and the nearest neighbor distance is in the range of from 0.3 to 3 μm. Such kits may further comprise (a) a terminal transferase for attaching a homopolymer tail to said DNA fragments to provide a binding site for a first end of said adaptor oligonucleotide, (b) a ligase for ligating a strand of said adaptor oligonucleotide to ends of said DNA fragment to form said DNA circle, (c) a primer for annealing to a region of the strand of said adaptor oligonucleotide, and (d) a DNA polymerase for extending the primer annealed to the strand in a rolling circle replication reaction. The above adaptor oligonucleotide may have a second end having a number of degenerate bases in the range of from 4 to 12. Such kits may further comprise reagents and buffers for identifying the sequences of DNA fragments of the concatemers.

In another aspect the invention provides kits for sequencing probe sequences comprising the following components: (i) a first set of probes for hybridizing to a plurality of concatemers randomly disposed on discrete spaced apart regions of a support surface, the concatemers each containing multiple copies of a probe sequence; and (iii) a second set of probes for hybridizing to the plurality of concatemers such that whenever a probe from the first set hybridizes contiguously to a probe from the second set, the probes are ligated. Such kits may further include a ligase, a ligase buffer, and a hybridization buffer. In some embodiments, the discrete spaced apart regions may have capture oligonucleotides attached and the concatemers may each have a region complementary to the capture oligonucleotides such that said concatemers are capable of being attached to the discrete spaced apart regions by formation of complexes between the capture oligonucleotides and the complementary regions of said concatemers.

Applications of Self-Assembled Single Molecule Arrays

Random arrays of the invention may be used for a wide variety of large-scale genetic measurements, including, but not limited to, gene expression, exon profiling, sequence comparisons, protein binding analysis, genome-wide copy number assessments, methylation analysis, and the like. Several exemplary applications are described below.

A. Gene Expression Analysis

After probe sequence identification, random arrays of the invention may be used as conventional high-density expression arrays. In one aspect, such random arrays may be constructed from sets of gene sequences assembled from pre-existing samples selected from commercial, non-profit, or government depositories, e.g. ATCC, or the like. Alternatively, random arrays may be constructed from a reference cDNA library, e.g. that may be from a single individual or from multiple individuals (so that consensus amounts of expression products are present). Protocols for using such arrays are similar to those of conventional high-density arrays, e.g. Lockhart et al, Nature Biotechnology, 14: 1675-1680 (1996); Mahadevappa et al, Nature Biotechnology, 17: 1134-1136 (1999); Kuhn et al, Genome Research, 14: 2347-2356 (2004); Eberwine et al, Proc. Natl. Acad. Sci., 89: 3010-3014 (1992); Phillips et al, Methods, 10: 283-288 (1996); Hacia et al, U.S. Pat. No. 6,013,449; Naderi et al, BMC Genomics, 5: 9 (2004); Expression Analysis Technical Manual (Affymetrix, Santa Clara, Calif.), and the like, which references are incorporated by reference for their disclosure of extraction, processing and labeling of RNA from biological samples for hybridization to high-density arrays. For total RNA preparation, several commercial kits may be used, such as QIAGEN's RNeasy Total RNA Isolation kit; Invitrogen Life Technologies' TRIzol reagent; and QIAGEN's Oligotex mRNA kit. In one aspect, a minimum of 5 ug total RNA at 0.5-1.0 ug/ul concentration, or 0.2 ug poly(A) mRNA at >0.02 ug/ul concentration is used to obtain sufficient quantity of labeled cRNA for hybridization to the random arrays. Briefly, cRNA, an exemplary pool of nucleic acid fragments, is formed by reverse transcribing with a oligo(dT) primer containing a promoter sequence, first strand cDNA synthesis, followed by RNase-H-mediated second strand synthesis, after which the resulting double stranded cDNA is purified and treated with RNA polymerase in the presence of appropriate monomers. Conventional labeling may be used, e.g. a portion of the monomers in cRNA synthesis may be biotinylated, so that after fragmentation and hybridization, various streptavidinated labels may be applied to the random array.

B. Sequence Comparisons by Mismatch Detection.

Figure 4:
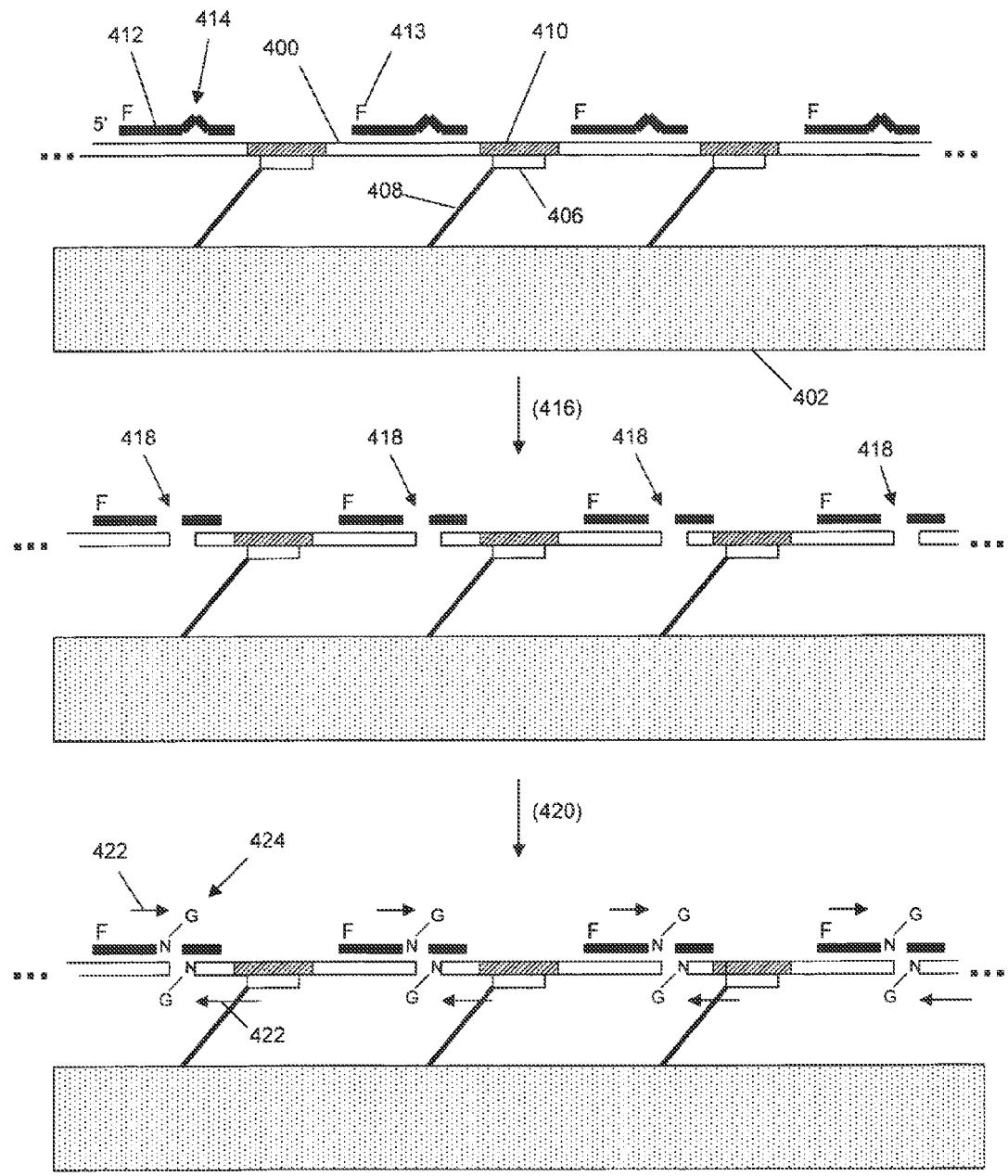
FIG. 4 illustrates diagrammatically an application of the invention for detecting target sequences whose sequences vary from those of corresponding probe sequences.

The ability of longer probes of 70-100 bases in length to discriminate single base mismatch mutations is diminished compared with short probes of <25 bases in length. However, a mismatch detection assay may be used to identify single base changes. This approach is based on the ability of a group of enzymes with the ability to detect single base mismatches in a heteroduplex structure. If there is a mismatch between the target and the nano-ball probe then these sites will be cleaved by the mis-match detection enzyme, e.g. Youil, R., Kemper, B. W., and Cotton, R. G. (1995), *Proc Nad Acad Sci USA* 92:87-91; Mashal, R. D., Koontz, J., and Sklar, J. (1995), *Nat Genet.* 9:177-183; Babon, J. J., McKenzie, M., and Cotton, R. G. (2003), *Mol Biotechnol* 23:73-81, which references are incorporated by reference. The enzyme will cleave both strands of the hybrid effectively creating a new 3-prime end since target molecules will be 3-prime blocked with a label or with a dideoxy nucleotide prior to the action of the enzyme. The new 3' ends released are then labeled with a distinguishable fluorescent label to that used for the hybrid detection, e.g. by terminal transferase. Although this does not provide the nature of mutation or polymorphism it does allow the assignment of mutations to a 10-100 base interval of the genome, which can optionally be directly sequenced or otherwise determined. One embodiment of such scheme is illustrated in FIG. 4. Concatemer (401) comprising adaptor oligonucleotides (410) and probe sequences (400) is fixed to solid support (402) via capture oligonucleotides (406) that are linked to solid support (402) by linker (408). Target sequences (412) labeled with a first fluorescent label "F" (413) hybridize to probe sequences (400) possibly forming single-base mismatches (414) when probe and target sequences differ. After hybridization of target sequences (412), the random array is treated with a mismatch cleavage endonuclease, which cleaves at the mismatch sites leaving double stranded breaks (418) in which there are free 3' ends. The broken strands are then treated (420) with a terminal transferase or polymerase that adds labeled nucleotides (424). The label for labeled nucleotide (424), usually a second fluorescent label "G," is selected so that it is distinguishable from first fluorescent label "F." Thus, target sequences varying from their corresponding probe sequences are detected by the generation of two signals from a single site on the random array. Alternatively, a mismatch recognition enzyme may be used that generates a single nick in the test-strand/probe strand duplex (e.g. instead of the double stranded cleavage as shown at (418) in FIG. 4), after which a free 3' end may be extended in the presence of labeled dNTPs.

C. Genome-Wide Deletion Detection.

Figure 5A:
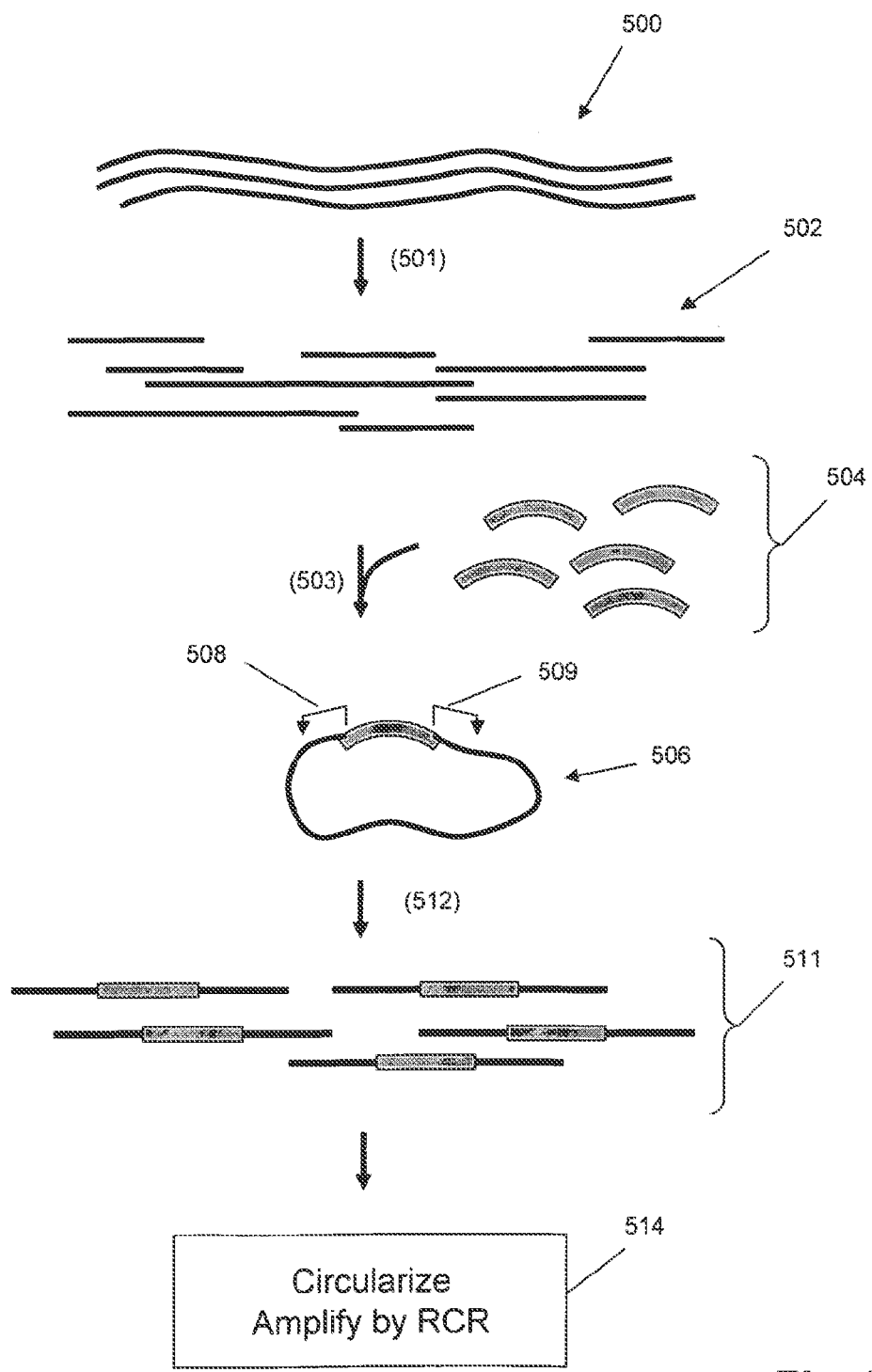
FIG. 5A-5C illustrate diagrammatically an application of the invention for detecting deletions and/or restriction site polymorphisms in a genome.
Figure 5B:
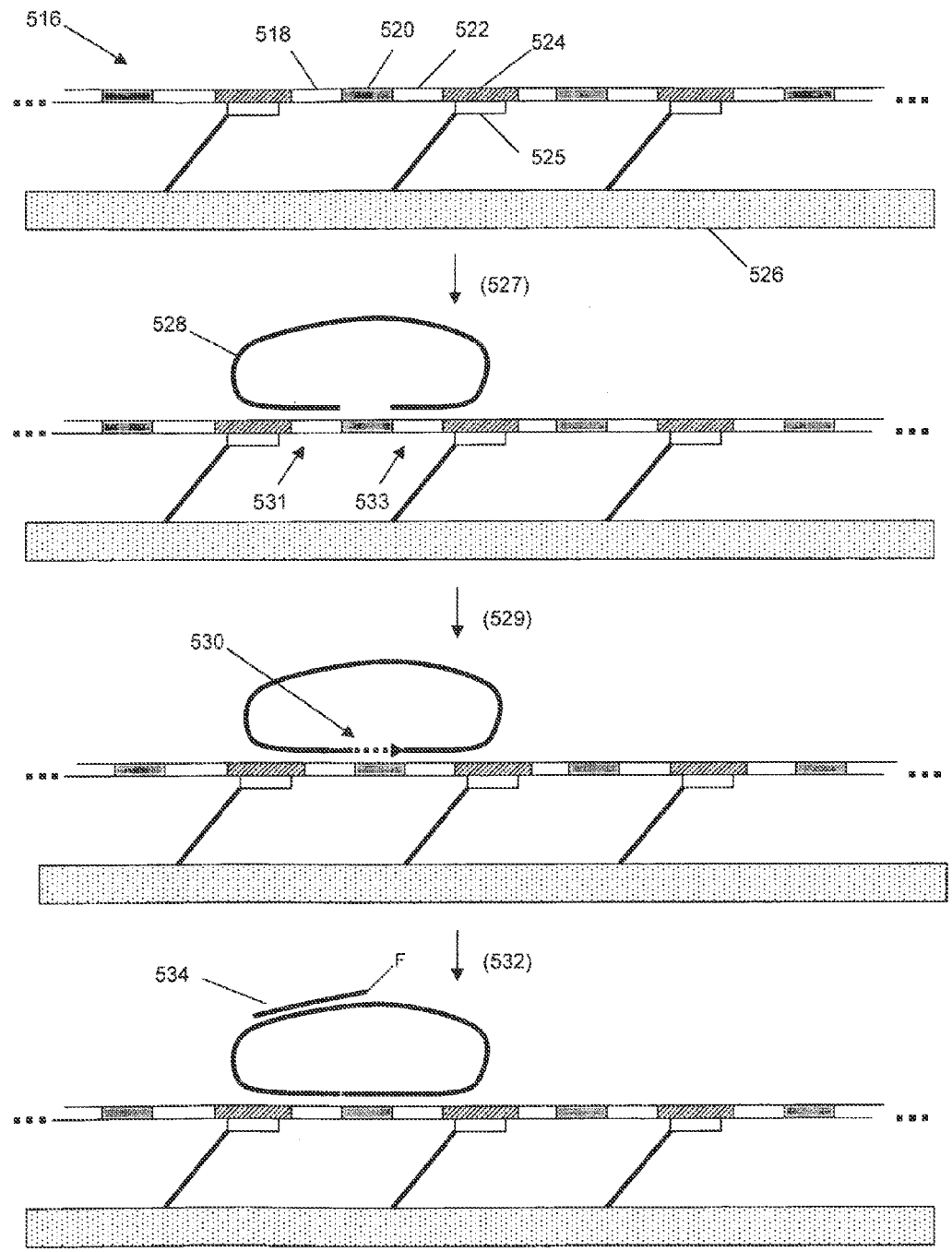
Figure 5C:
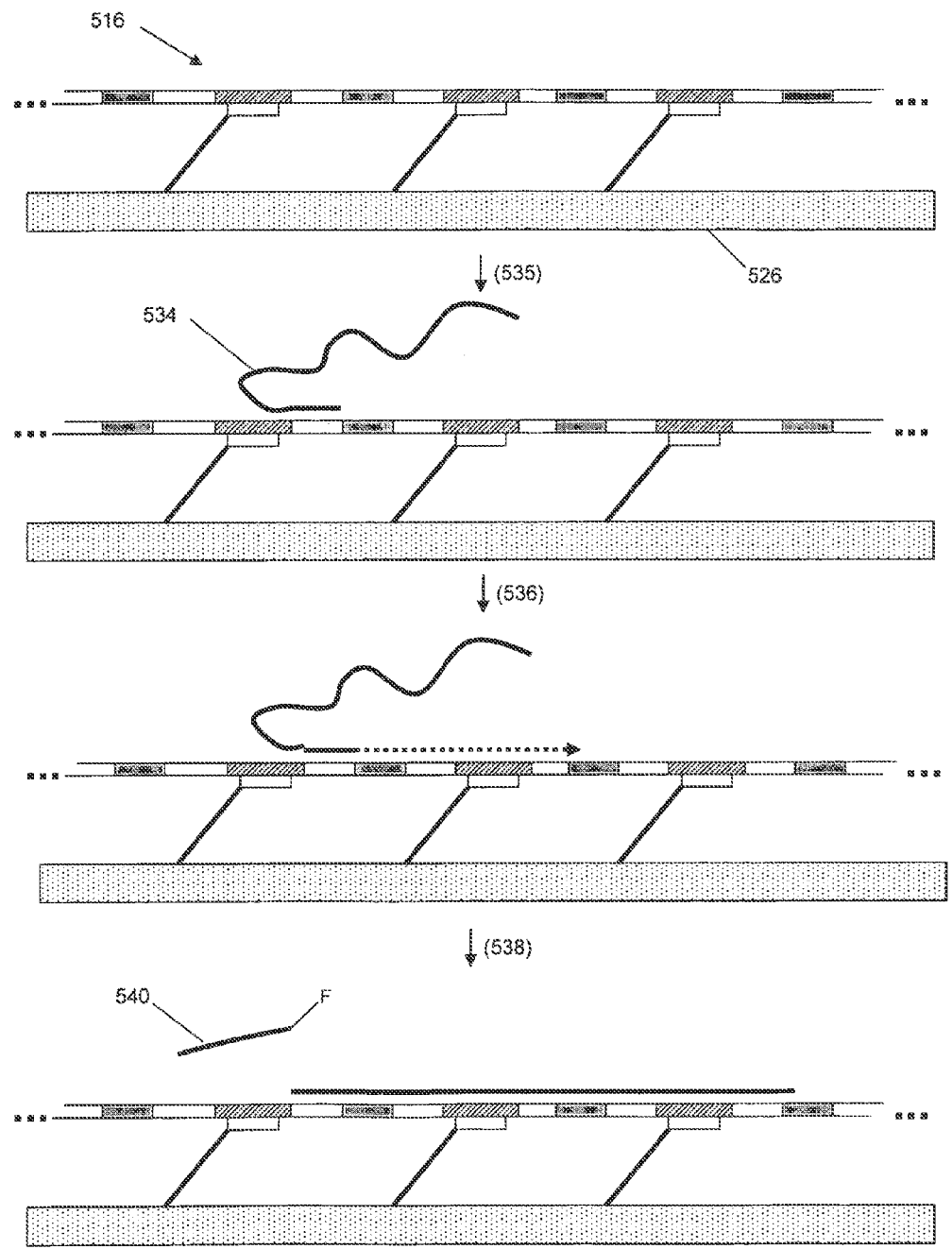

Random arrays of the invention may be used to detect deletions, inversions, duplications, translocations, and/or other sequence differences between a test population of target sequences and a reference population of probe sequences. A reference population may comprise, for example, probe sequences on a random array that are derived from normal cells or tissue of a cancer patient, whereas a test population of target sequences are derived from tumor cells or tissue. In one aspect, probe sequences are constructed from mate-paired ends of fragments. That is, after digestion of a source nucleic acid, e.g. normal tissue genomic DNA, with a restriction endonuclease, the resulting fragments are circularized with an adaptor that contains type IIs restriction endonuclease sites oriented so that they cleave to the interior of the fragment, preferably at a maximum distance into the fragment, e.g. as disclosed by Shendure et al, Science, 309: 1728-1732 (2005); Smith et al, U.S. patent publication 2006/0024681; and the like, which references are incorporated by reference. A useful type IIs enzyme for such cleavage is Mme I, or like enzyme with a large distance between its recognition site and cleavage site, e.g. greater than 10 basepairs, and preferably greater than 20 basepairs. Fragments for generating mate-paired ends may be size-selected so that mate-paired ends of a random array contain such subsets of mate-paired ends from fragments of defined lengths. In one aspect, such subsets of mate-paired ends are derived from fragments that are at least 50 nucleotides in length, or at least 100 nucleotides in length, or at least 300 nucleotides in length, or at least 1000 nucleotides in length, or at least 3000 nucleotides in length, or at least 10,000 nucleotides in length. One embodiment of this application is illustrated in FIG. 5A-5C. Nucleic acids (500) from a reference source are digested (501) with a restriction endonuclease to produce fragment population (502), which is then combined (503) with adaptors (504) that contain type IIs restriction endonuclease sites at each end. After ligation, resulting circles (506) are treated with restriction endonuclease recognizing the sites in the adaptors (504) so that they cleave into the fragment capturing regions (508) and (510) that are adjacent to the restriction site of the enzyme use to generate fragments (502), i.e. mate-paired ends of fragments (502). Fragments (511) may then be circularized and used to generate concatemers for random arrays. Target sequences for applying to the random array are generated by digesting a test source nucleic acid with the same restriction endonuclease (i.e. in treatment (501)) as that used to produce mate-paired ends for making the random array. FIGS. 5B and 5C illustrate one manner in which signals may be generated, or not generated, depending on whether a deletion exists (or restriction site mutation exists) that alters the sequences of the mate-pair ends of target sequences. Exemplary concatemer (516) generated from a fragment (511) is illustrated in FIG. 5B. Mate-paired ends, e.g. (518) and (522), sandwich adaptor (504) (which contains the two type IIs sites). Concatemer (516) is fixed to solid support (526) by duplexes formed between adaptors (524) and capture oligonucleotides (525). Target sequences (528) are prepared as single stranded complements of their corresponding probe sequences and are hybridized (527) to the random array containing concatemer (516). Where there are no restriction site mutations or no deletions in the source nucleic acids, then duplexes (531) and (533) form between the mate-paired ends of target sequence (528) and a probe sequence in concatemer (516). In one aspect, the ends of target sequence (516) may be joined (529), e.g. by polymerase extension and ligation (530), to form a closed circle, after which the random array is treated with exonuclease to digest target sequences having free ends. After such treatment, closed circles may be detected with probes (534) constructed from the same restriction fragments as the probe sequences and target sequences, i.e. such probes are the complements of target sequences (528). As illustrated in FIG. 5C, whenever a deletion or restriction site mutation is present in test sequence (528), either one or both of the mate-paired ends of target sequence (534) failed to form duplexes with concatemer (516) when hybridized (535) thereto. Thus, extension and ligation fails to result in a closed circle (536), so that exonuclease digestions removes the portion of target sequence (534) that can hybridize to probe (540), which is then washed of the array so that no signal is generated.

Further Applications of the Invention

Concatemers of synthetic or natural DNA fragments of about 30-3000 bases initiated with a primer that has RNA polymerase promoter extension may be used to produce long RNA that, in turn, may be in vitro translated into a peptide or polypeptide. Likewise, multiple copies of the same polypeptide may be produced with an adapter (used for forming DNA circles) along with a coded spacer peptide. The resulting protein with 100 to 10000 amino acids may be folded maybe initiated by the spacer protein to form several to hundreds of almost independently folded unit peptides. Each peptide may form several domains for binding different molecules like antibodies, oligo peptides, single or double-stranded oligonucleotides or other chemical compounds that can be used to identify given peptide.

These proteins may be attached to binding sites of a support having a peptide or other molecule that binds to spacer peptide or by using other general protein binding chemistry. Small size of active binding sites surrounded by non-binding support allow to attach only one (first to bind) protein by binding saturation of all available binding molecules in the binding site or by physical prevention of other proteins to interact with the same binding site. To minimize double or multiple occupancy proteins smaller than give size may be removed by size separation or saturation of spacer protein.

DNA concatemers prepared in accordance with the invention may be used as detection and quantification arrays having the following features: (i) having a mixture of DNA fragments 10, 20, 50, 100 or more bases and shorter than 25, or 50, or 100, or 500, or 1000, or 2000 or 5000 or 10,000 bases from a source DNA; (ii) production by attaching concatemers of the same fragment or by in-situ amplification of a single DNA molecule; (iii) identification of the DNA in each spot by hybridization signature or partial or complete sequence determination; (iv) probe sequences are all sequence variants of given length 8 to 20 base; (v) a support with DNA/RNA with natural or analog bases spots in a grid or random spot array with informative single stranded DNA longer than 15, or 25, or 50, or 75 or 100 or 125, or 150, or 200, or 250, or 300, or 400, or 500, or 750, or 1000 bases and more than 10,000 or 100,000 or 1 million spots per $mm^2$ containing multiple copies of the same DNA per spot, wherein more than 1000 or 10,000 or 100,000 different DNA is present in the array and which DNA is at which spot is determined after DNA attachment; (vi) more than 50, 60, 70, 80, 90 or 95% of spots in a grid have single informative DNA species excluding errors produced by amplification; (vii) a plate with 2, 4, 6, 8, 10, 12, 16, 24, 32, 48, 64, 96, 192, 384 or more such DNA arrays, where in most cases the same DNA is in different spots in the individual arrays; (viii) probe DNA fragments from multiple (2-2000, 10-2000, 20-2000, 50-2000, 100-2000, 100-10,000, 500-10,000 species; (ix) probe DNA fragments that have SNP or other differences between individuals or species; (xi) identity or sequence of DNA/RNA or other detector molecule in usable spots is inferred by matching hybridization or other binding signature or partial or complete polymer sequence to reference data base of signatures or sequences.

A support with protein, peptide or other polymer detector molecules spots in a grid or random spot array with informative peptide or other polymer longer than 15, or 25, or 50, or 75 or 100 or 125, or 150, or 200, or 250, or 300, or 400, or 500, or 750, or 1000 and more amino acids or other monomers, and more than 10,000 or 100,000 or 1 million spots per $mm^2$ containing multiple copies of the same peptide or other polymer per spot, wherein more than 1000 or 10,000 or 100,000 different peptides or other polymers is present in the array and which peptide or other polymer is at which spot is determined after peptides or other polymer attachment to the support. Peptide or other polymer is present in a spot are identified by generating binding signature using antibodies, oligo peptides, oligonucleotides, sets of compounds. Binding signatures are developed by experimental testing of known peptides or other polymers in tubes, wells or spotted arrays with predefined spot for each tested peptide or other polymer. Expected binding signatures are developed by computing binding properties of each expected peptide (or other polymer) with each binder molecule.

EXAMPLE 1

Glass Cover Slip as Random Array Support

Derivatization Protocol

In this example, a glass cover slip is prepared for use as a support for disposing DNA concatemers. The following materials are used:
Millipore DI water
2.5 ml of 3-Aminopropyldimethylethoxysilane (Gelest)
1.6 grams p-phenylenediisothiocyanate (Acros Organics/ fisher)
210 grams KOH (VWR)
Ethanol (VWR)
Methanol (VWR)
Pyridine (VWR)
N,N-dimethylformamide (VWR)
Acetone (VWR)
Equipment
100 c oven
magnetic stir plate
1 2"×0.5" magnetic stir bar
2 4 liter Nunc beaker
7 4"×8"×4" glass containers 1 liter graduated cylinder
1 100 ml graduated cylinder
1 lab scale
1 Metzler scale
1 large weigh boat
1 small weigh boat
1 pair thick nitrile gloves
1 large funnel
1 ml pipettman with filter tips
1 nalgene stir bar
1 airtight container (tupperware)

Using the large graduated cylinder measure 950 ml of ethanol, add to the 4 liter Nunc beaker. Measure 50 ml of DI water in the small graduated cylinder and add to the same nunc beaker. Measure out 210 grams of KOH pellets in a weigh boat on the lab scale. Add stir bar and KOH pellets to the beaker. Place beaker on stir plate and stir at low speed until KOH is completely dissolved. While KOH is dissolving, lay out 6 pre-washed glass containers. fill containers 2-5 with DI water until ½ inch from top (~800 ml). Fill container 6 with acetone ½" to top. Carefully pour dissolved KOH solution into container 1 until ½" to top. Add racked cover slips to container 1 wait 3 minutes, remove racks from container 1 and wash in containers 2-5 leaving racks in each container a minimum of 15 seconds. Submerse racks briefly in container 6. Set aside racks, dispose the solutions from containers 1 and 2 in the basic waste container using the large funnel and thick nitrile gloves, clean and dry labware. Lay out 7 clean and dry glass containers. Add 775 ml of acetone to container 1 add 2.5 ml of DI water to container 1. stir container 1 with pipette tip for 20 seconds. With a new pipette tip add 2.5 ml of 3-aminopropyldimethylethoxysilane to container 1. Stir with pipette tip for 10 seconds. Immerse all 5 racks of cover slips into container 1. Cover container 1 with polypropylene box top. Wait 45 minutes. 15 minutes prior to the completion of the reaction, fill containers 2-4 until ½" to top with acetone, fill container 5 with water ½" to top. Fill container 6 until ½" to top with acetone. Upon reaction completion (45 minutes) transfer cover slip racks 1-5 from container 1 to container 2, wait 15 seconds. Repeat this though container 6. Place racks into empty container 7 and put in 100 c oven. Wait one hour. Lay out 7 glass containers. After racks come out of oven, use the Meltzer scale to weigh out 1.6 grams of p-phenylenediisothiocyanate (PDC) in the small weigh boat. Pour 720 ml dimethylformamide into the cleaned 1 liter graduated cylinder, fill to 800 ml with pyridine. Pour 50% this solution into a clean class container then pour it back into the cylinder to mix (repeat once). Fill container 1 until ½" to top with this solution. Add the PDC from the weigh boat to container 1. Use stir bar to mix solution. Crush PDC clumps that refuse to dissolve, then stir again. Cover slip racks should be cool by now. Place all 5 racks into container one. Cover with polypropylene box top. Wait 2 hours. 10 minutes prior to reaction completion fill containers 2 and 3 with methanol until ½" from top. Fill containers 4 and 5 with acetone until ½" from top. Fill container 6 with 65% acetone 35% water until ½" from top. Fill container 7 with acetone. Successively transfer racks through all containers, waiting 15 seconds between each transfer. Remove racks from container 7 dump contents of containers 1-7 into organic waste drum. Replace racks to container 7 and dry in oven for 15 minutes. Place dry racks into airtight container, they are now ready for attachment.

EXAMPLE 2

Preparation of RCR Products form E. coli Genomic DNA and Disposition onto a Glass Cover Slip E. coli genomic DNA (32 ug) (Sigma Chemical Co) was fragmented with 0.16 U of DnaseI (Epicentre) at 37° C. for 10 min and then heat inactivated at 95° C. for 10 min. Reaction products were distributed with an average size of 200 bp as determined by agarose gel electrophoresis. If reaction products did not meet the required size distribution they were further digested with the addition of fresh enzyme. The final concentration was 200 ng/ul of genomic DNA.

The Dnase digested DNA (26 ng/ul) was reacted with Terminal deoxynucleotide transferase (0.66 U/ul) from New England Biolabs (NEB) in reaction buffer supplied by NEB. The reaction contained dATP (2 mM) and was performed at 37 C for 30 min and then heat inactivated at 70 C for 10 min. The DNA sample was then heated to 95 C for 5 min before rapid cooling on ice.

A synthetic DNA adapter was then ligated to the 5' end of the genomic DNA by first forming a hybrid of a 65-base oligonucleotide (TATCATCTACTGCACTGACCGGATGT-TAGGAAGACAAAAGGAAGCTGAGGGTCACAT TAACGGAC) (SEQ ID NO: 8) with a second oligonucleotide (NNNNNNNGTCCGTTAATGTGAC 3' 2'3'ddC) (SEQ ID NO: 9) at the 3' end of the 65mer in which the 7 "Ns" form an overhang. The shorter oligo will act as a splint for ligation of the 65mer to the 5' end of the genomic fragments. The splint molecule consists of 7 degenerate bases at its 5' end to hybridize to variable bases at the 5' end of the genomic DNA. The adapter hybrid was formed by slowly hybridizing 1200 pmol of adapter with 1200 pmol of splint in 52 ul from 95 C to room temperature over 1 hr.

T4 DNA Ligase (0.3 U/ul) was combined with genomic DNA (17 ng/ul) and adapter-splint (0.5 uM) in 1× ligase reaction buffer supplied by NEB. The ligation proceeded at 15 C for 30 min, 20 C for 30 min and then inactivated at 70 C for 10 min. A second splint molecule (AGAT-GATATTTTTTTT 3' 2'3'ddC) (SEQ ID NO: 10) (0.6 uM) was then added to the reaction and the mix was supplemented with more ligase buffer and T4 DNA ligase (0.3 U/ul). The reaction proceeded at 15 C for 30 min and then at 20 C for 30 min before inactivation for 10 min at 70 C.

The ligation mix was then treated with exonuclease I (NEB) (1 U/ul) at 37 C for 60 min, followed by inactivation at 80 C for 20 min Rolling circle replication was performed in reaction buffer supplied by NEB with BSA (0.1 ug/ul), 0.2 mM each dNTP, an initiating primer (TCAGCTTCCTTTTGTCTTCCTAAC) (SEQ ID NO: 11) at 2 fmol/ul, exonuclease treated ligation of genomic DNA at 24 pg/ul, and Phi 29 polymerase (0.2 U/ul). The reaction was performed for 1 hr at 30 C and then heat inactivated at 70 C for 10 min.

RCR reaction products were attached to the surface of cover slips by first attaching amine modified oligonucleotides to the surface of the cover slips. A capture probe ([AMI-NOC6][SP-C18][SP-C18]GGATGTTAGGAAGA-CAAAAGGAAGCTGAGG) (SEQ ID NO: 12) (50 uM) was added to the DITC derivatized cover slips in 0.1 uM NaHCO3 and allowed to dry at 40 C for about 30 min. The cover slips were rinsed in DDI water for 15 min and dried. RCR reaction products (4.5 ul) were then combined with 0.5 ul of 20×SSPE and added to the center of the slide. The sample was allowed to air dry and non-attached material was washed off for 10 min in 3×SSPE and then briefly in DDI water. The slide was then dried before assembly on the microscope. Attached RCR products were visualized by hybridizing an 11mer TAMRA labeled probe that is complementary to a region of the adapter RCR reaction products were formed from a single stranded 80mer synthetic DNA target (NNNNNNNGCATANCAC-GANGTCATNATCGTNCAAACGTCAGTC-CANGAATCNAGA TCCACTTAGAN-TAAAAAAAAAAAA) (SEQ ID NO: 13) as above but without poly A addition with TDT. The RCR reaction contained target molecules at an estimated 12.6 fmol/ul. Reaction products (5 ul) were combined with SSPE (2×) and SDS (0.3%) in a total reaction volume of 20 ul. The sample was applied to a cover-slip in which lines of capture probe ([AMINOC6][SP-C18][SP-C18]GGATGTTAGGAAGA-CAAAAGGAAGCTGAGG), deposited in a solution of 50 uM with 0.1 uM NaHCO3, were dried onto the surface and left in a humid chamber for 30 min. The solution was then washed off in 3×SSPE for 10 min and then briefly in water.

Various reaction components were tested for their effect upon RCR product formation. The addition of Phi 29 to the RCR reaction at a final concentration of 0.1 U/ul rather than 0.2 U/ul was found to create a greater proportion of RCR products that were of larger intensity after detection probe hybridization. The addition of initiating primer at 10 to 100 fold molar ratio relative to estimated target concentration was also found to be optimal. Increased extension times produced more intense fluorescent signals but tended to produce more diffuse concatemers. With the current attachment protocols a 2 hr extension time produced enhanced signals relative to a 1 hr incubation with minimal detrimental impact upon RCR product morphology.

Figure 6:
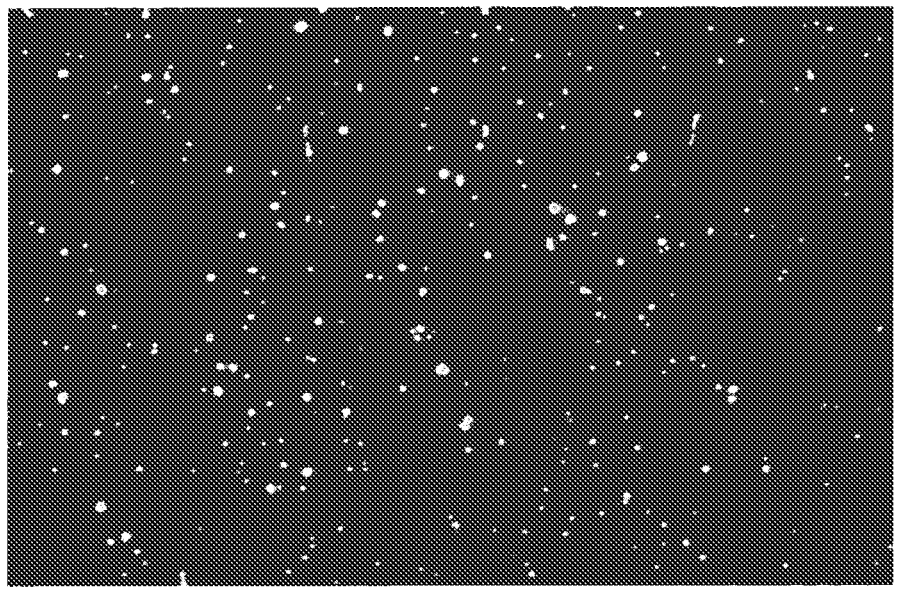
FIG. 6 is an image of a glass surface containing a disposition of concatemers of E. coli fragments.

Further optimization of RCR products have been achieved by reducing the estimated concentration of synthetic and genomic targets to 0.1 to 0.25 fmol/ul in the RCR reaction. This typically results in distinct and unique RCR products on the surface of the microscope slide using method 1 for attachment. For synthetic targets in which a higher concentration of targets in the RCR reaction may be present (e.g. >5 fmol/ul), RCR products may be attached by method 2. Attachment method 1. RCR reaction products (4.5 ul) were combined with 0.5 ul of 20×SSPE and added to the center of the slide. The sample was allowed to air dry and non-attached material was washed off for 10 min in 3×SSPE and then briefly in DDI water. The slide was then dried before assembly on the microscope. Attached RCR products were visualized by hybridizing an 11mer TAMRA labeled probe that is complementary to a region of the adapter. Attachment method 2. RCR reaction products (1 ul) were combined with 50 ul of 3×SSPE and added to the center of the cover slip with capture probe attached. Addition of SDS (0.3%) was found to promote specific attachment to the capture probes and not to the derivatized surface. The sample was incubated at room temperature for 30 min and non-attached material was washed off for 10 min in 3×SSPE and then briefly in DDI water. The slide was then dried before assembly on the microscope. Attached RCR products were visualized by hybridizing an 11mer TAMRA labeled probe that is complementary to a region of the adapter. The above protocols provide RCR product densities of about 1 RCR product per 2-4 micron square. Exemplary image of a resulting cover slip is shown in FIG. 6.

EXAMPLE 3

Distinguish RCR Products on Random Arrays Using Fluorescently Labeled Probes

Figure 7:
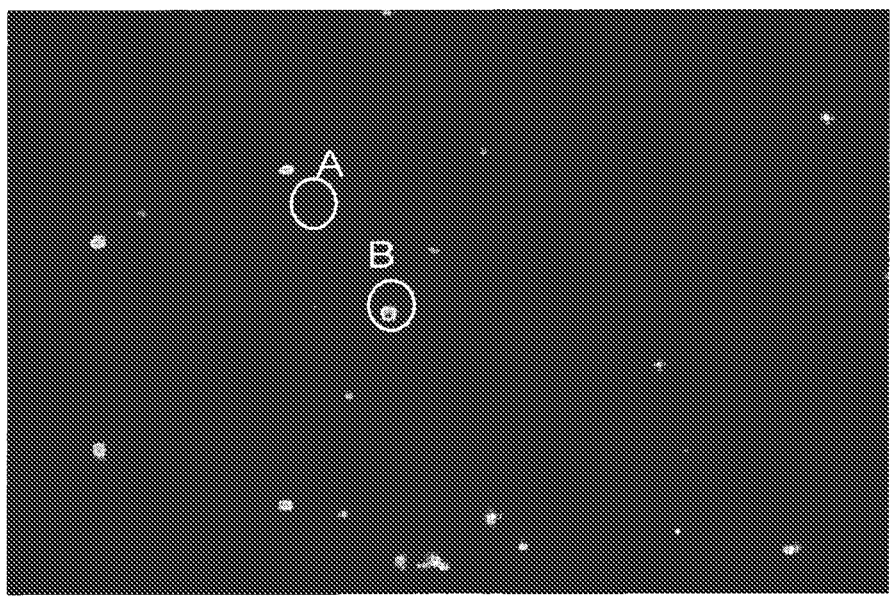
FIG. 7 is an image of concatemers derived from two different organisms that are selectively labeled using oligonucleotide probes.
Figure 8:
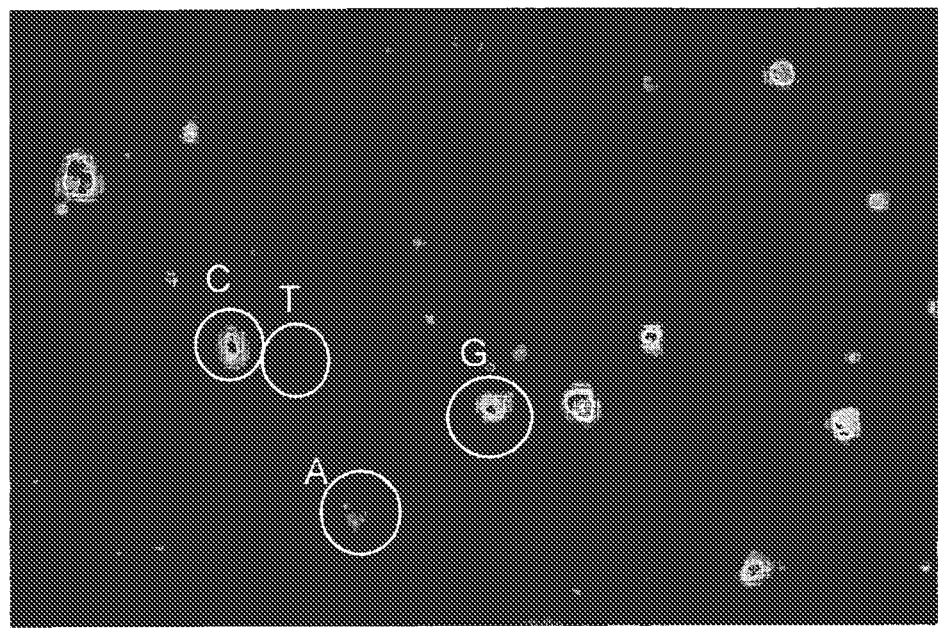
FIG. 8 is an image of concatemers of DNA fragments that contain a degenerated base, each of which is identified by a specific ligation probe.
Figure 9:
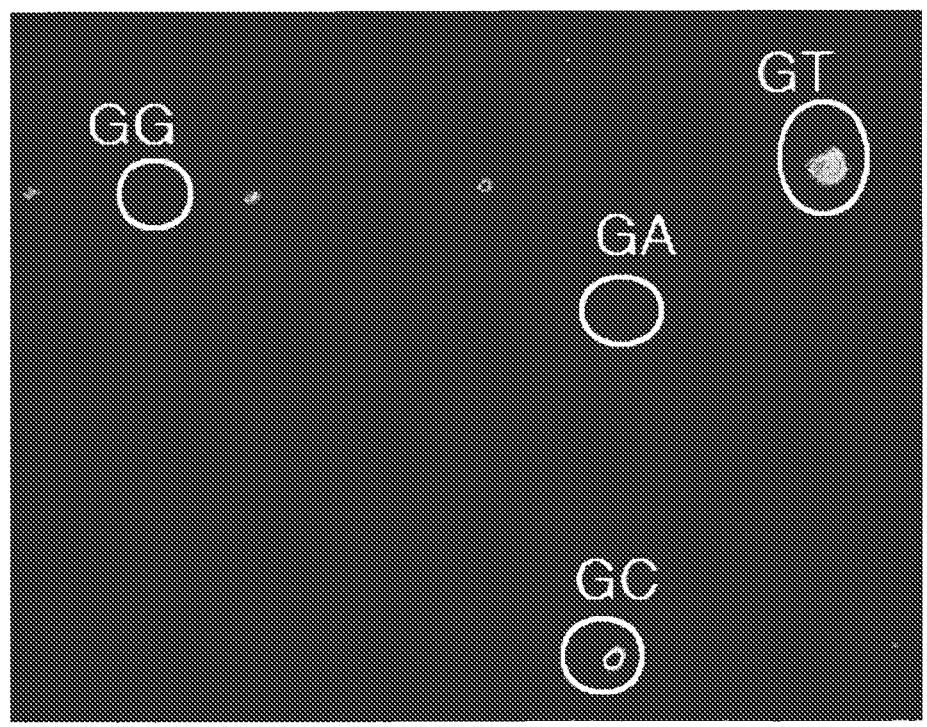
FIG. 9 is an image of concatemers of DNA fragments that contain a segment of degenerate bases, pairs of which are identified by specific probes.

PCR products from diagnostic regions of Bacillus anthracis and Yersinia pestis were converted into single stranded DNA and attached to a universal adaptor. These two samples were then mixed and replicated together using RCR and deposited onto a glass surface as a random array. Successive hybridization with amplicon specific probes showed that each spot on the array corresponded uniquely to either one of the two sequences and that they can be identified specifically with the probes, as illustrated in FIG. 7. This result demonstrates sensitivity and specificity of identifying DNA present in submicron sized DNA concatemers having about 100-1000 copies of a DNA fragment generated by the RCR reaction. A 155 bp amplicon sequence from B. anthracis and a 275 bp amplicon sequence from Y. pestis were amplified using standard PCR techniques with PCR primers in which one primer of the pair was phosphorylated. A single stranded form of the PCR products was generated by degradation of the phosphorylated strand using lambda exonuclease. The 5' end of the remaining strand was then phosphorylated using T4 DNA polynucleotide kinase to allow ligation of the single stranded product to the universal adaptor. The universal adaptor was ligated using T4 DNA ligase to the 5' end of the target molecule, assisted by a template oligonucleotide complementary to the 5' end of the targets and 3' end of the universal adaptor. The adaptor ligated targets were then circularized using bridging oligonucleotides with bases complementary to the adaptor and to the 3' end of the targets. Linear DNA molecules were removed by treating with exonuclease I. RCR products (DNA concatemers) were generated by mixing the single-stranded samples and using Phi29 polymerase to replicate around the circularized adaptor-target molecules with the bridging oligonucleotides as the initiating primers.

To prepare the cover slips for attaching amine-modified oligonucleotides, the cover slips were first cleaned in a potassium/ethanol solution followed by rinsing and drying. They were then treated with a solution of 3-aminopropyldimethylethoxysilane, acetone, and water for 45 minutes and cured in an oven at 100° C. for 1 hour. As a final step, the cover slips were treated with a solution of p-phenylenediisothiocyanate (PDC), pyridine, and dimethylformamide for 2 hours. The capture oligonucleotide (sequence 5'-GGATGTTAGGAA-GACAAAAGGAAGCTGAGG-3') (SEQ ID NO: 14) is complementary to the universal adaptor sequence. and is modified at the 5' end with an amine group and 2 C-18 linkers. For attachment, 10 µl of the capture oligo at 10 µM in 0.1M NaHCO$_3$ was spotted onto the center of the derivatized cover slip, dried for 10 minutes in a 70° C. oven and rinsed with water. To create an array of DNA concatemers, the RCR reaction containing the DNA concatemers was diluted 10-folds with 3×SSPE, 20 µl of which was then deposited over the immobilized capture oligonucleotides on the cover slip surface for 30 minutes in a moisture saturated chamber. The cover slip with the DNA concatemers was then assembled into a reaction chamber and was rinsed by 2 ml of 3×SSPE. Arrayed target concatemer molecules derived from B. anthracis and Y. pestis PCR amplicons were probed sequentially with TAMRA-labeled oligomer: probe BrPrb3 (sequence: 5'-CATTAACGGAC-3' (SEQ ID NO: 15), specifically complementary to the universal adaptor sequence), probe Ba3 (sequence: 5'-TGAGCGATTCG-3' (SEQ ID NO: 16), specifically complementary to the Ba3 amplicon sequence), probe Yp3 (sequence: 5'-GGTGTCATGGA-3', specifically complementary to the Yp3 amplicon sequence). The probes were hybridized to the array at a concentration of 0.1 µM for 20 min in 3×SSPE at room temperature. Excess probes were washed off with 2 ml of 3×SSPE. Images were taken with the TIRF microscope. The probes were then stripped off with 1 ml of 3×SSPE at 80° C. for 5 minutes to prepare the arrayed target molecules for the next round of hybridization.

By overlaying the images obtained from successive hybridization of 3 probes, as shown in FIG. 7, it can be seen that most of the arrayed molecules that hybridized with the adaptor probe would only hybridize to either the amplicon 1 probe (e.g. "A" in FIG. 7) or the amplicon 2 probe (e.g. "B" in FIG. 7), with very few that would hybridize to both. This specific hybridization pattern demonstrates that each spot on the array contains only one type of sequence, either the *B anthracis* amplicon or the *Y. pestis* amplicon.

EXAMPLE 4

Decoding a Base Position in Arrayed Concatemers Created from a Synthetic 80-Mer Oligonucleotide Containing a Degenerated Base Individual molecules of a synthetic oligonucleotide containing a degenerate base can be divided into 4 sub-populations, each may have either an A, C, G or T base at that particular position. An array of concatemers created from this synthetic DNA may have about 25% of spots with each of the bases. Successful identification of these sub-populations of concatemers was demonstrated by four successive hybridization and ligation of pairs of probes, specific to each of the 4 bases, as shown in FIG. 8. A 5' phosphorylated, 3' TAMRA-labeled pentamer oligonucleotide was paired with one of the four hexamer oligonucleotides. Each of these 4 ligation probe pairs should hybridize to either an A, C, G or T containing version of the target. Discrimination scores of greater than 3 were obtained for most targets, demonstrating the ability to identify single base differences between the concatemer targets. The discrimination score is the highest spot score divided by the average of the other 3 base-specific signals of the same spot. By adjusting the assay conditions (buffer composition, concentrations of all components, time and temperature of each step in the cycle) higher signal to background and full match to mismatch ratios are expected. This was demonstrated with a similar ligation assay performed on the spotted arrays of 6-mer probes. In this case full-match/background ratio was about 50 and the average full match/mismatch ratio was 30. The results further demonstrate the ability to determine partial or complete sequences of DNA present in concatemers by increasing the number of consecutive probe cycles or by using 4 or more probes labeled with different dyes per each cycle. Synthetic oligonucleotide (T1A: 5'-NNNNNNNNGCATANCACGANGTCAT-NATCGTNCAAACGTCAGTCCANGAATCNAGAT CCACTTAGANTAAAAAAAAAAAA-3') (SEQ ID NO: 13) contains at position 32 a degenerate base. Universal adaptor was ligated to this oligonucleotide and the adaptor-T1A DNA was circularized as described before. DNA concatemers made using the rolling circle replication (RCR) reaction on this target were arrayed onto the random array. Because each spot on this random array corresponded to tandemly replicated copies originated from a single molecule of T1A, therefore DNA in a particular arrayed spot would contain either an A, or a C, or a G, or a T at positions corresponding to position 32 of T1A. To identify these sub-populations, a set of 4 ligation probes specific to each of the 4 bases was used. A 5' phosphorylated, 3' TAMRA-labeled pentamer oligonucleotide corresponding to position 33-37 of T1A with sequence CAAAC (probe T1A9b) was paired with one of the following hexamer oligonucleotides corresponding to position 27-32: ACTGTA (probe T1A9a), ACTGTC (probe T1A10a), ACTGTG (probe T1A11a), ACTGTT (probe T1A12a). Each of these 4 ligation probe pairs should hybridize to either an A, C, G or T containing version of T1A. For each hybridization cycle, the probes were incubated with the array in a ligation/hybridization buffer containing T4 DNA ligase at 20° C. for 5 minutes. Excess probes were washed off at 20° C. and images were taken with a TIRF microscope. Bound probes were stripped to prepare for the next round of hybridization.

An adaptor specific probe (BrPrb3) was hybridized to the array to establish the positions of all the spots. The 4 ligation probe pairs, at 0.4 μM, were then hybridized successively to the array with the base identifications as illustrated for four spots in FIG. 8. It is clear that most of the spots are associated with only one of the 4 ligation probe pairs, and thus the nature of the base at position 32 of T1A can be determined specifically.

EXAMPLE 5

Decoding Two Degenerate Bases at the End of a Synthetic 80-Mer Oligonucleotide

The same synthetic oligonucleotide described above contains 8 degenerate bases at the 5' end to simulate random genomic DNA ends. The concatemers created from this oligonucleotide may have these 8 degenerate bases placed directly next to the adaptor sequence. To demonstrate the feasibility of sequencing the two unknown bases adjacent to the known adaptor sequence, a 12-mer oligonucleotide (UK0-12 sequence 5'-ACATTAACGGAC-3') (SEQ ID NO: 17) with a specific sequence to hybridize to the 3' end of the adaptor sequence was used as the anchor, and a set of 16 TAMRA-labeled oligonucleotides in the form of BBNNNNNN were used as the sequence-reading probes. For each hybridization cycle, 0.2 uM of UK0-12 anchor probe and 0.4 uM of the BBNNNNNN probe were incubated with the array in a ligation/hybridization buffer containing T4 DNA ligase at 20° C. for 10 minutes. Excess probes were washed off at 20° C. and images were taken with a TIRF microscope. Bound probes were stripped to prepare for the next round of hybridization.

Using a subset of the BBNNNNNN probe set (namely GA, GC, GG and GT in the place of BB), spots were able to be identified spots on the concatemer array created from targets that specifically bind to one of these 4 probes, with an average full match/mismatch ratio of over 20, as shown in FIG. 9.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. A "hybridization buffer" is a buffered salt solution such as 5×SSPE, or the like. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476, 930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Enzymatic ligation usually takes place in a ligase buffer, which is a buffered salt solution containing any required divalent cations, cofactors, and the like, for the particular ligase employed.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 mL, to a few hundred μL, e.g. 200 μL.

"Polynucleotide" or "oligonucleotide" are used interchangeably and each mean a linear polymer of nucleotide monomers. As used herein, the terms may also refer to double stranded forms. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions, when such analogs are incompatible with enzymatic reactions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Sequence determination" in reference to a target polynucleotide means determination of information relating to the sequence of nucleotides in such target polynucleotide. Such information may include the identification or determination of partial as well as full sequence information of the target polynucleotide. The sequence information may be determined with varying degrees of statistical reliability or confidence. In one aspect, the term includes the determination of the identity, ordering, and locations of one, two, three, or four types of nucleotides within a target polynucleotide. For example, in some embodiments sequence determination may be effected by identifying the ordering and locations of a single type of nucleotide, e.g. cytosines, within a target polynucleotide. For example, in the sequence "CATCGC . . . " sequence information may be obtained that is represented as a binary code, e.g. "100101 . . . " for "C-(not C)-(not C)-C-(not C)-C . . . " and the like. In another aspect, sequence information means the identity and ordering of a plurality of contiguous nucleotides in a target polynucleotide. In still another aspect, sequence information includes the identity and ordering of a plurality of nucleotides within a target polynucleotide that are not contiguous. In another aspect, the identities and ordering of a plurality of nucleotides may be known, but spacing between adjacent nucleotides may not be known, or only known to within a range of possible values.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" usually means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method of determining sequence information for a target polynucleotide, comprising:
   (a) providing a plurality of concatemers, each concatemer having been obtained by:
      (i) forming a first circular DNA comprising a fragment of said target polynucleotide and a first adaptor, wherein the first adaptor comprises a binding site for a restriction enzyme that cleaves DNA at a cleavage site separated from said binding site by at least six nucleotides;
      (ii) forming a linearized DNA by a process that comprises cleaving the first circular DNA at a site that is internal to the target polynucleotide using a restriction endonuclease that binds to said binding site, whereby the linearized DNA comprises the first adaptor flanked on each side by a portion of said fragment;
      (iii) forming a second circular DNA comprising said linearized DNA and a second adaptor;
      (iv) amplifying the second circular DNA to form said concatemer;
   (b) forming an array of said concatemers bound to a surface; and
   (c) determining target sequences both upstream and downstream from the second adaptor by a process that comprises hybridizing oligonucleotides to the second adaptor in a plurality of the concatemers in the array.

2. The method of claim 1, wherein step (c) comprises:
   (i) hybridizing an anchor probe to a probe hybridization site in said second adaptor;
   (ii) hybridizing a sequencing probe to a target sequence of the target polynucleotide adjacent to the hybridized anchor probe; then
   (iii) ligating the sequencing probe and the anchor probe; and
   (iv) detecting the probe ligated in step (iii) to identify said nucleotide(s) in the target sequence.

3. The method of claim 2, wherein steps (i) through (iv) of step (c) are repeated to identify a nucleotide sequence of the target polynucleotide.

4. The method of claim 1 comprising sequentially hybridizing anchor probes to hybridization sites on both ends of the second adaptor.

5. The method of claim 1, wherein the target polynucleotide is genomic DNA.

6. The method of claim 1, wherein the surface comprises more than 100,000 concatemers per square millimeter.

7. The method of claim 6, wherein at least 70% of said concatemers are optically resolvable.

8. The method of claim 1, wherein the concatemers are bound to discrete spaced-apart regions on the surface.

9. The method of claim 8, wherein the concatemers are randomly disposed amongst said discrete spaced apart regions.

10. The method of claim 8, wherein each discrete spaced apart region has an area of less than 1 µm$^2$.

11. The method of claim 8, wherein the concatemers are bound to the discrete spaced-apart regions non-covalently.

12. The method of claim 8, wherein at least 80% of the discrete spaced apart regions have one concatemer attached.

13. The method of claim 1, wherein step (ii) comprises cleaving the first circular DNA on two sites outside of the first adaptor.

14. The method of claim 1, wherein step (c) comprises hybridizing oligonucleotides to the second adaptor at both ends of the adaptor so as to determine sequence of the target fragment beside or near both the first and the second adaptor in both directions.

15. The method of claim 1, wherein step (c) comprises hybridizing anchor probes to the second adaptor at or near both ends of the adaptor, hybridizing labeled sequencing probes to the target polynucleotide at positions adjacent to the anchor probes, and ligating sequencing probes to adjacent anchor probes.

* * * * *